(12) United States Patent
Griffith et al.

(10) Patent No.: US 12,196,737 B2
(45) Date of Patent: Jan. 14, 2025

(54) PROCESS TO GEOGRAPHICALLY ASSOCIATE POTENTIAL WATER QUALITY STRESSORS TO MONITORING STATIONS

(71) Applicant: SAS Institute Inc., Cary, NC (US)

(72) Inventors: Philip David Griffith, Tallahassee, FL (US); Andie Hodge, Adelphi, MD (US); Amir Naveed Lyall, Raleigh, NC (US); Kirby Ann Thomas, Tallahassee, FL (US); Srinivas Reddy Valisekkagari, Cary, NC (US); Ryan Todd Wendt, Cary, NC (US)

(73) Assignee: SAS INSTITUTE INC., Cary, NC (US)

( * ) Notice: Subject to any disclaimer, the term of this patent is extended or adjusted under 35 U.S.C. 154(b) by 0 days.

(21) Appl. No.: 17/945,428

(22) Filed: Sep. 15, 2022

(65) Prior Publication Data

US 2023/0089011 A1 Mar. 23, 2023

Related U.S. Application Data

(60) Provisional application No. 63/319,161, filed on Mar. 11, 2022, provisional application No. 63/246,231, filed on Sep. 20, 2021.

(51) Int. Cl.
*G01N 33/18* (2006.01)
(52) U.S. Cl.
CPC .................................... *G01N 33/18* (2013.01)
(58) Field of Classification Search
CPC ....................................................... G01N 33/18
See application file for complete search history.

(56) References Cited

U.S. PATENT DOCUMENTS

| 9,556,048 B1* | 1/2017 | Owings | C02F 3/06 |
| 2006/0020427 A1* | 1/2006 | Kahn | G01N 33/1886 |
| | | | 436/55 |

(Continued)

FOREIGN PATENT DOCUMENTS

| CN | 113449960 A | * | 9/2021 | |
| KR | 20060092420 A | * | 8/2006 | G06Q 50/26 |

OTHER PUBLICATIONS

Chen, "Method, system and device for water resources operation and scheduling of lake reservoirs and island river network in estuary area", May 19, 2021, CN113449960A, English Translation, downloaded from Espacenet on Nov. 19, 2022 (Year: 2021).*

(Continued)

*Primary Examiner* — Lina Cordero
*Assistant Examiner* — Lyudmila Zaykova-Feldman
(74) *Attorney, Agent, or Firm* — COATS & BENNETT, PLLC

(57) ABSTRACT

A computing device obtains data indicating a topography for an area comprising water and receives an indication of an identified data object representing a stressor to the area or a first monitoring station configurable to monitor the stressor. The computing device also determines a location for the identified data object in the topography and selects one or more related data objects to be related to the identified data object by determining a classification indicating whether the identified data object operates in water and selecting the one or more related data objects based on the location and the classification. The computing device also generates one or more controls for monitoring the area based on the selected one or more related data objects.

30 Claims, 39 Drawing Sheets

(56) References Cited

U.S. PATENT DOCUMENTS

| | | | | |
|---|---|---|---|---|
| 2006/0122794 | A1* | 6/2006 | Sprague | G06Q 50/26 702/32 |
| 2008/0195362 | A1* | 8/2008 | Belcher | G06F 30/00 703/2 |
| 2009/0118871 | A1* | 5/2009 | Debourke | E03C 1/041 340/5.1 |
| 2012/0048813 | A1* | 3/2012 | Irvin, Sr. | F04D 5/001 210/512.3 |
| 2012/0330549 | A1* | 12/2012 | Dannevik | G01W 1/10 702/3 |
| 2013/0021167 | A1* | 1/2013 | Harper, Jr. | G05B 9/02 340/870.01 |
| 2013/0118239 | A1* | 5/2013 | Forstmeier | H04Q 9/00 73/61.43 |
| 2015/0227655 | A1* | 8/2015 | Sun | G01V 20/00 703/2 |
| 2019/0297397 | A1* | 9/2019 | Fleishman | H04L 67/12 |
| 2022/0343194 | A1* | 10/2022 | Louisell, III | G16Y 10/35 |
| 2023/0022508 | A1* | 1/2023 | Howell | G06T 17/05 |

OTHER PUBLICATIONS

Kim et al. System and method for coastal water quality management, 2006, KR200608-23, English translation downloaded from Espacenet on Apr. 20, 2024 (Year: 2006).*

Water Science School, "Phosphorus and Water", Jun. 5, 2018, pp. 1-6, retrieved on Jun. 22, 2022, retrieved from Internet: https://www.usgs.gov/special-topics/water-science-school/science/phosphorus-and-water.

Water Encyclopedia, "Attenuation of Pollutants", Jan. 1, 2022, pp. 1-4, retrieved on Jun. 22, 2022, retrieved from Internet: https://www.waterencyclopedia.com/A-Bi/Attenuation-of-Pollutants.html.

Oklahoma-Texas Water Science Center, "Water-quality monitoring station on Lake Houston", Apr. 30, 2013, pp. 1-3, retrieved on Jun. 16, 2022, retrieved from internet: https://usgs.gov/media/images/water-quality-monitoring-station-lake-houston.

United States Enviromental Protection Agency, "Basic Information about the Lower Merrimack River Monitoring Station", Jul. 14, 2021, pp. 1-6, retrieved on Jun. 16, 2022, retrieved from internet: https://www.epa.gov/merrimackriver/basic-information-about-lower-merrimack-river-monitoring-station.

Glenn, N., "What is a data object? Definition, Types, & Examples", Understand Data Analysis, Jan. 1, 2022, pp. 1-9, retrieved on Jun. 16, 2022, retrieved from internet: https://analystanswers.com/what-is-a-data-object-definition-types-examples/.

Metadata, "National Watershed Boundary Dataset (WBD)", Jul. 20, 2017, pp. 1-25, retrieved on Apr. 1, 2022, retrieved from internet: https://gis.arkansas.gov/Metadata/HTML/asdi.Water.WBD_HU12_USGS_export.html.

NHD Plus, "NHDPlus Verision 2: User Guide (Data Model Version 2.1)", Mar. 13, 2019, pp. 1-183, EPA.

ESRI, "Watershed (Spatial Analyst) ArcGIS Pro 3.1", pp. 1-4, retrieved on Sep. 7, 2022, retrieved from internet: https://pro.arcgis.com/en/pro-app/latest/tool-reference/spatial-analyst/watershed.htm.

ESRI, "How To: Create a watershed model using the Hydrology toolset", Aug. 2, 2022, pp. 1-5, retrieved on Sep. 7, 2022, retrieved from internet: https://support.esri.com/en/technical-article/000012346.

National Hydrography, "Tools for National Hydrography Datasets", pp. 1-9, retrieved on Sep. 7, 2022, retrieved from internet: https://www.usgs.gov/national-hydrography/tools.

ESRI, "Trace Downstream", pp. 1-3, retrieved on Sep. 7, 2022, retrieved from internet: https://doc.arcgis.com/en/arcgis-online/analyze/trace-downstream.htm.

* cited by examiner

| Variable Name 2002 | Flowlines 2004 | Flowline VAA 2006 | Water Bodies 2008 | Flow Table 2010 | Catchments 2012 | Stations 2014 | Stressors 2016 |
|---|---|---|---|---|---|---|---|
| HUC8 | X | X | X | | | | |
| NHDPlusID | X | | X | X | X | X | X |
| REACH CODE | X | | X | | | | |
| X COORDINATE | X | | X | | X | X | X |
| Y COORDINATE | X | | X | | X | X | X |

FIG. 20A

| Variable Name 2022 | Flowlines 2024 | FlowlineVAA 2026 | Waterbodies 2028 | Flow Table 2030 | Stations 2032 | Stressors 2034 |
|---|---|---|---|---|---|---|
| FCODE | X | | X | | | |
| FLOW DIRECTION (FROM/TO) | | | | X | | |
| FTYPE | X | | X | | | |
| HUC8 | | | | | X | X |
| LENGTHKM | X | | | | X | |
| MONITORING LOC ID | | | | | X | |
| PARENT FEATURE | X | | | | | X |
| STRESSOR ID | | | | | | |
| MAIN PATH (DIVERGENCE) | | X | | | | |

FIG. 20B

| Analyte Description 2062 | Analyte Measure 2064 |
|---|---|
| Temperature (C), Water | Maximum |
| Temperature (F), Water | Maximum |
| Turbidity | Maximum |
| Turbidity, Transmissometer | Maximum |
| Turbidity, Hch Turbidimiter | Maximum |
| Color | Maximum |
| Color, Apparent | Maximum |
| Specific Conductance | Maximum |
| Oxygen, Dissolved (DO) | Minimum |
| Oxygen, Dissolved Percent Saturation | Minimum |
| Biochemical Oxygen Demand-5 | Maximum |
| pH | Maximum & Minimum |
| Alkalinity, Total (as CaCO3) | Maximum |
| Alkalinity, Bicarbonate (as CaCO3) | Maximum |
| Flow | Average[1] |
| Chlorine, Total Residual | Maximum and Minimum |
| Chlorine, Free Available | Maximum |
| Solids, Total Dissolved (TDS) | Maximum |
| Solids, Total Dissolved (TDS) | Maximum |
| Nitrogen, Ammonia, Total (as NH4) | Maximum |
| Nitrogen, Nitrate, Total (as NO3) | Maximum |
| Mercury, Total Recoverable | Maximum |
| Iron, Total (As Fe) | Maximum |

*FIG. 20C*

| DESCRIPTION 2072 | Grouping 2074 |
|---|---|
| Temperature (C), Water | Convert Fahrenheit to Celsius and group |
| Temperature (F), Water | |
| Turbidity | These should be grouped. |
| Turbidity, Transmissometer | |
| Turbidity, Hch Turbidimiter | |
| Turbidity, Field - Nepholometric | |
| Turbidity, Lab, Ntu | |
| Nitrogen, Total | "Total Nitrogen" is the sum of "Nitrate-Nitrite (N)" and "Nitrogen - Total Kjeldahl". Calculated results at the DMR Header level can be grouped with 00600- Nitrogen, Total and 00603- Nitrogen, Total (as N). |
| Nitrogen, Total (as N) | |
| Nitrogen, Kjeldahl, Total (as N) | |
| Nitrite plus Nitrate, Total 1 det. (as N) | |
| Iron, Total (As Fe) | These should be grouped. |
| Iron, Total_(As Fe) | |

| FCode | FEATURE_TYPE | FCODE_DESC |
|---|---|---|
| 33400 | CONNECTOR | feature type only, no attributes |
| 33600 | CANAL/DITCH | feature type only, no attributes |
| 33601 | CANAL/DITCH | Canal/Ditch Type\|aqueduct |
| 33603 | CANAL/DITCH | Canal/Ditch Type\|stormwater |
| 42000 | UNDERGROUND CONDUIT | feature type only, no attributes |
| 42002 | UNDERGROUND CONDUIT | Positional Accuracy\|indefinite |
| 42800 | PIPELINE | feature type only, no attributes |
| 42801 | PIPELINE | Product\|water, Pipeline Type\|aqueduct, Relationship to Surface\|at or near |
| 42803 | PIPELINE | Product\|water, Pipeline Type\|aqueduct, Relationship to Surface\|underground |
| 42804 | PIPELINE | Product\|water, Pipeline Type\|aqueduct, Relationship to Surface\|underwater |
| 42805 | PIPELINE | Product\|water, Pipeline Type\|general case, Relationship to Surface\|at or near |
| 42807 | PIPELINE | Product\|water, Pipeline Type\|general case, Relationship to Surface\|underground |
| 42808 | PIPELINE | Product\|water, Pipeline Type\|general case, Relationship to Surface\|underwater |
| 42809 | PIPELINE | Product\|water, Pipeline Type\|penstock, Relationship to Surface\|at or near |
| 42813 | PIPELINE | Product\|water, Pipeline Type\|siphon, Relationship to Surface\|unspecified |
| 46000 | STREAM/RIVER | feature type only, no attributes |
| 46003 | STREAM/RIVER | Hydrographic Category\|intermittent |
| 46006 | STREAM/RIVER | Hydrographic Category\|perennial |
| 46007 | STREAM/RIVER | Hydrographic Category\|ephemeral |
| 55800 | ARTIFICIAL PATH | feature type only, no attributes |
| 56600 | COASTLINE | feature type only, no attributes |

*FIG. 28A*

| Event Type | Event ID | Event Flowline | Event Estuary | Type | Station/Stressor ID | Station /Stressor Flowline | Station /Stressor Estuary |
|---|---|---|---|---|---|---|---|
| BGA | 63542 | | ENR-2 | Monitoring Station | 35987 | | ENR-1 |
| BGA | 63542 | | ENR-2 | Monitoring Station | 51248 | 001245 | |
| BGA | 63542 | | ENR-2 | Monitoring Station | 63542 | | ENR-2 |
| BGA | 63542 | | ENR-2 | Monitoring Station | 63295 | 034556 | |
| BGA | 63542 | | ENR-2 | WAFR Facility | 789525 | 034559 | |
| BGA | 63542 | | ENR-2 | Water Reuse | 2512775 | | ENR-3 |
| RT | 2566888 | 065893 | | Monitoring Station | 69999 | 098332 | |
| RT | 2566888 | 065893 | | Tidal | 356998 | 084957 | |
| FK | 777569 | | ENR-5 | Weather | 465972 | | ENR-4 |

*FIG. 30B*

PROCESS TO GEOGRAPHICALLY ASSOCIATE POTENTIAL WATER QUALITY STRESSORS TO MONITORING STATIONS

CROSS-REFERENCE TO RELATED APPLICATIONS

This application claims the benefit of, and priority based on, 35 U.S.C. § 119 to U.S. Provisional Application No. 63/246,231, filed Sep. 20, 2021, and U.S. Provisional Application No. 63/319,161, filed Mar. 11, 2022, the disclosures of each of which are incorporated herein by reference in their entirety.

BACKGROUND

A land area can be of varying elevation. For instance, a land area can contain one or more catchments that are elevation-identified regions capable of collecting and/or draining water (e.g., it is a basin of lower elevation than surrounding areas). Land areas can also have water bodies within the land areas or on the edge of land areas where there is a defined area of accumulated water.

Waste facilities, farms, and other entities that produce natural or human pollutants can act as a stressor on water quality in the land area in which they are located. For instance, a farm may release a pollutant or a fertilizer chemical that threatens or causes damage to water quality. Monitoring stations may be useful to measure factors relevant to water quality to protect the water in a land area.

SUMMARY

In an example embodiment, the present disclosure provides a computer-program product tangibly embodied in a non-transitory machine-readable storage medium. The computer-program product includes instructions operable to cause a computing system to obtain data indicating a topography for an area comprising water and receive an indication of an identified data object. The identified data object may represent, for example, a stressor to the area or a first monitoring station configurable to monitor the stressor. The computer-program product instructions are further operable to cause the computing system to determine a location for the identified data object in the topography and to select, from a plurality of data objects, one or more related data objects to be related to the identified data object. To select the one or more related data objects, the computer-program product instructions in this embodiment are operable to cause the computing system to determine a classification indicating whether the identified data object operates in water. In this embodiment, when a given stressor is a candidate to stress a water ecosystem in the area, it is classified as operating in water. When a given monitoring station is configurable to monitor a given stressor by monitoring water in the area it is classified as operating in water. The computer-program product instructions in this embodiment are then operable to cause the computing system to select, based on the location and the classification, the one or more related data objects. In this embodiment, the one or more related data objects comprise one or more of a second monitoring station configurable to monitor the stressor, a cause for the stressor to the area, and an effect of the stressor on the area. The computer-program product instructions are further operable to cause the computing system to generate one or more controls for monitoring the area based on the one or more related data objects that were selected.

Embodiments disclosed herein also include corresponding computer-program product, apparatus, and methods. For example, in another example embodiment, the present disclosure provides a computer-implemented method. The method comprises obtaining data indicating a topography for an area comprising water and receiving an indication of an identified data object. In this embodiment of the present disclosure, the identified data object represents a stressor to the area or a first monitoring station configurable to monitor the stressor. The method further comprises determining a location for the identified data object in the topography and selecting, from a plurality of data objects, one or more related data objects to be related to the identified data object. In this embodiment, selecting the one or more related data objects to be related to the identified data object comprises determining a classification indicating whether the identified data object operates in water. In this embodiment, when a given stressor is a candidate to stress a water ecosystem in the area, it is classified as operating in water. When a given monitoring station is configurable to monitor a given stressor by monitoring water in the area it is classified as operating in water. Then, based on the location and the classification, the one or more related data objects are selected. In this embodiment, the one or more related data objects comprise one or more of a second monitoring station configurable to monitor the stressor, a cause for the stressor to the area, and an effect of the stressor on the area. The method further comprises generating one or more controls for monitoring the area based on the one or more related data objects selected.

In another example embodiment, the present disclosure provides a computing device comprising a processor and memory. The memory contains instructions that when executed by the processor, control the computing device to obtain data indicating a topography for an area comprising water and receive an indication of an identified data object. The identified data object may represent, for example, a stressor to the area or a first monitoring station configurable to monitor the stressor. Additionally, when executed by the processor, the instructions control the computing device to determine a location for the identified data object in the topography and to select, from a plurality of data objects, one or more related data objects to be related to the identified data object. To select the one or more related data objects, the instructions, when executed by the processor, control the computing device to determine a classification indicating whether the identified data object operates in water. In this embodiment, when a given stressor is a candidate to stress a water ecosystem in the area, it is classified as operating in water. When a given monitoring station is configurable to monitor a given stressor by monitoring water in the area it is classified as operating in water. The instructions, when executed by the processor, further control the computing device to select, based on the location and the classification, the one or more related data objects. In this embodiment, the one or more related data objects comprise one or more of a second monitoring station configurable to monitor the stressor, a cause for the stressor to the area, and an effect of the stressor on the area. Additionally, the instructions, when executed by the processor, further control the computing device to generate one or more controls for monitoring the area based on the one or more related data objects that were selected.

Other features and aspects of example embodiments are presented below in the Detailed Description when read in connection with the drawings presented with this application.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 20A-20D illustrate example data tables for mapping in at least one embodiment of the present technology.

FIG. 23 illustrates an example graphical user interface for displaying graphical representations pertaining to multiple facilities in at least one embodiment of the present technology.

FIGS. 28A-28B illustrate an example for determining a flow network near a coastline in at least one embodiment of the present technology.

FIGS. 30A-30B illustrates an example of generating a data table for associating effects of stressors with monitoring stations and the causes of stressors in at least one embodiment of the present technology.

DETAILED DESCRIPTION

In the following description, for the purposes of explanation, specific details are set forth in order to provide a thorough understanding of embodiments of the technology. However, it will be apparent that various embodiments may be practiced without these specific details. The figures and description are not intended to be restrictive.

The ensuing description provides example embodiments only, and is not intended to limit the scope, applicability, or configuration of the disclosure. Rather, the ensuing description of the example embodiments will provide those skilled in the art with an enabling description for implementing an example embodiment. It should be understood that various changes may be made in the function and arrangement of elements without departing from the spirit and scope of the technology as set forth in the appended claims.

Specific details are given in the following description to provide a thorough understanding of the embodiments. However, it will be understood by one of ordinary skill in the art that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional operations not included in a figure. A process may correspond to a method, a function, a procedure, a subroutine, a subprogram, etc. When a process corresponds to a function, its termination can correspond to a return of the function to the calling function or the main function.

Systems depicted in some of the figures may be provided in various configurations. In some embodiments, the systems may be configured as a distributed system where one or more components of the system are distributed across one or more networks in a cloud computing system.

Figure 1:
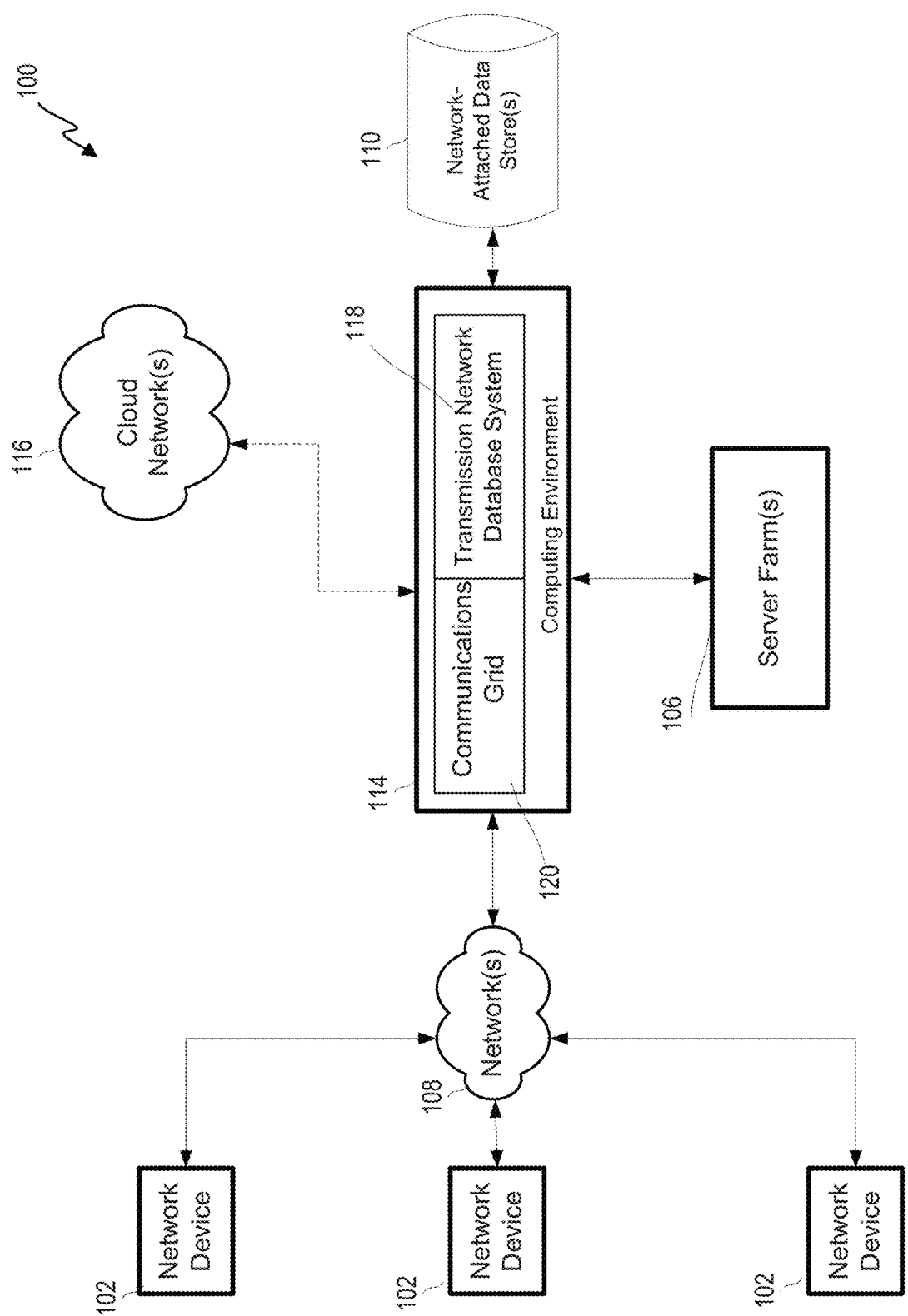
FIG. 1 illustrates a block diagram that provides an illustration of the hardware components of a computing system, according to at least one embodiment of the present technology.

FIG. 1 is a block diagram that provides an illustration of the hardware components of a data transmission network 100, according to embodiments of the present technology. Data transmission network 100 is a specialized computer system that may be used for processing large amounts of data where a large number of computer processing cycles are required.

Data transmission network 100 may also include computing environment 114. Computing environment 114 may be a specialized computer or other machine that processes the data received within the data transmission network 100. Data transmission network 100 also includes one or more network devices 102. Network devices 102 may include client devices that attempt to communicate with computing environment 114. For example, network devices 102 may send data to the computing environment 114 to be processed, may send signals to the computing environment 114 to control different aspects of the computing environment or the data it is processing, among other reasons. Network devices 102 may interact with the computing environment 114 through a number of ways, such as, for example, over one or more networks 108. As shown in FIG. 1, computing environment 114 may include one or more other systems. For example, computing environment 114 may include a database system 118 and/or a communications grid 120.

Figure 8:
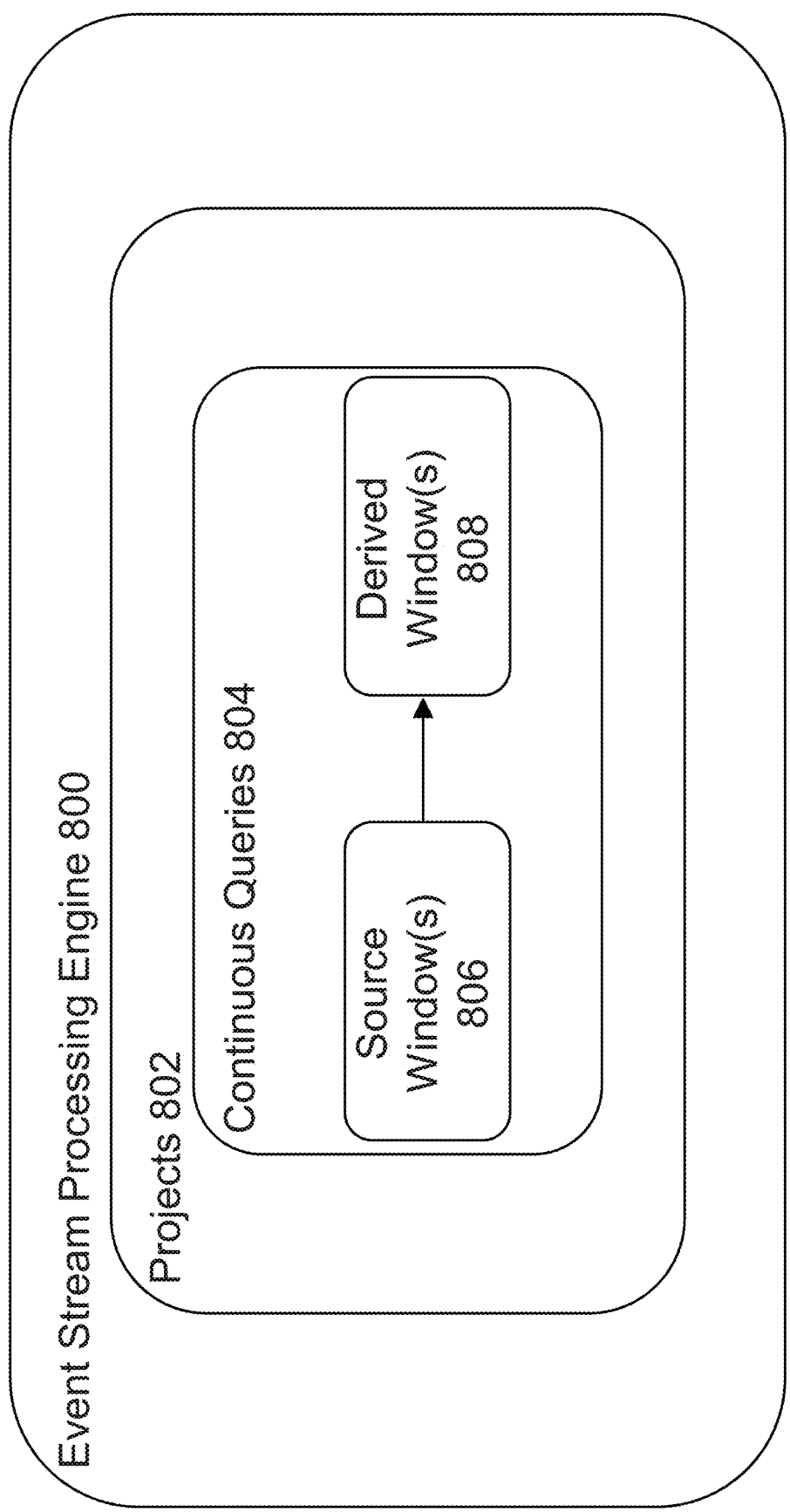
FIG. 8 illustrates a block diagram including components of an Event Stream Processing Engine (ESPE), according to at least one embodiment of the present technology.
Figure 9:
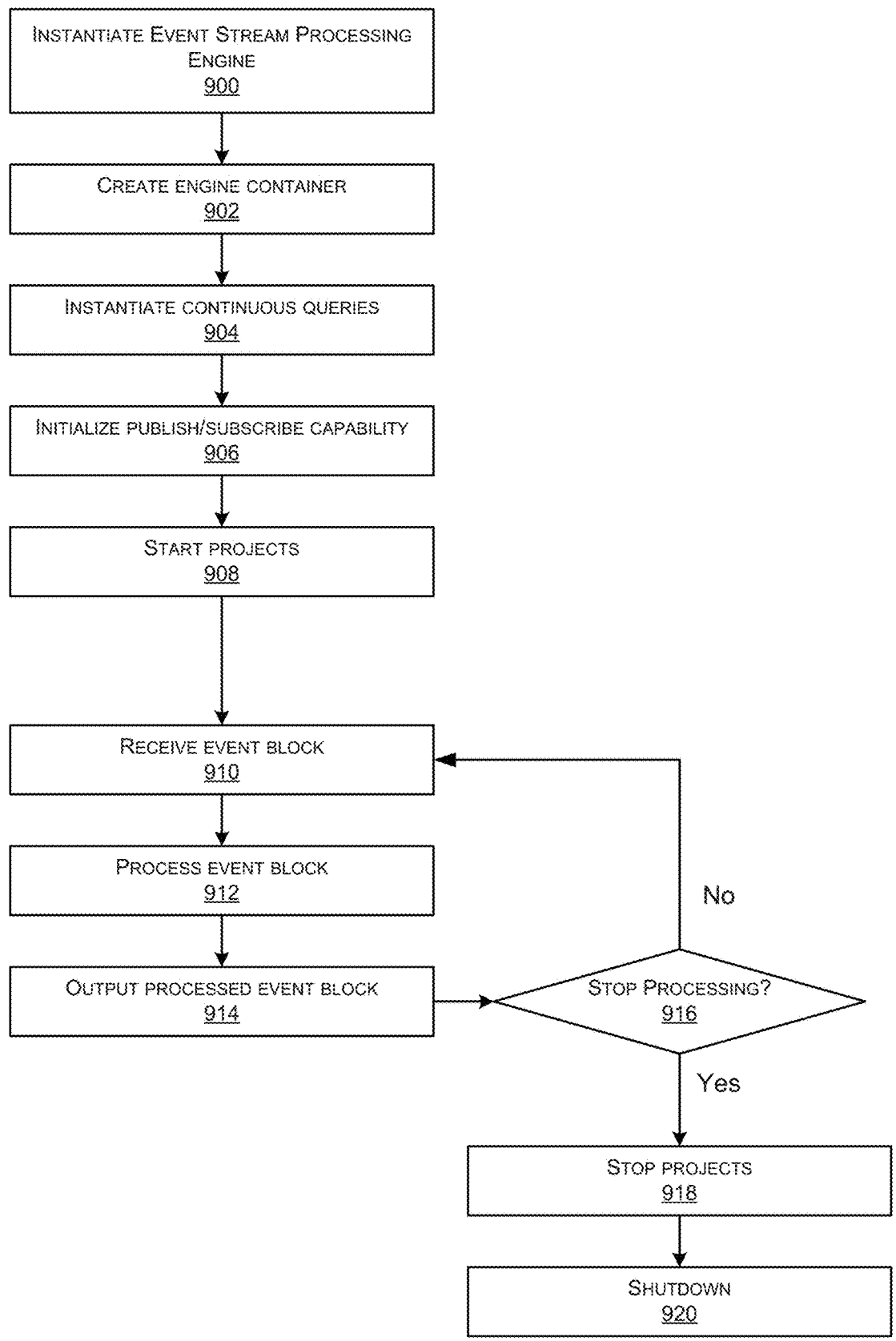
FIG. 9 illustrates a flow chart showing an example process including operations performed by an event stream processing engine, according to at least one embodiment of the present technology.
Figure 10:
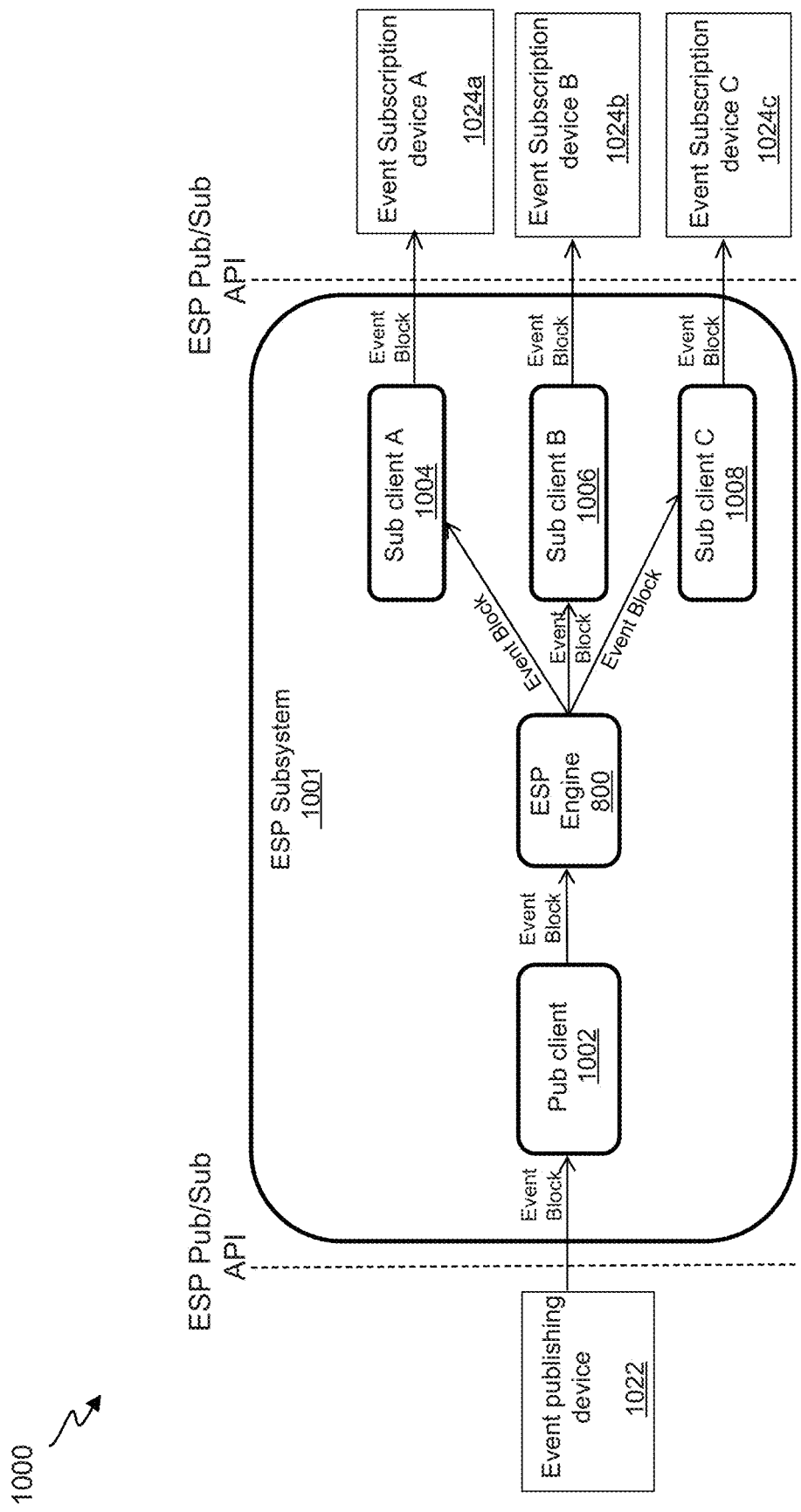
FIG. 10 illustrates an ESP system interfacing between a publishing device and multiple event subscribing devices, according to at least one embodiment of the present technology.

In other embodiments, network devices may provide a large amount of data, either all at once or streaming over a period of time (e.g., using event stream processing (ESP), described further with respect to FIGS. 8-10), to the computing environment 114 via networks 108. For example, network devices 102 may include network computers, sensors, databases, or other devices that may transmit or otherwise provide data to computing environment 114. For example, network devices may include local area network devices, such as routers, hubs, switches, or other computer networking devices. These devices may provide a variety of stored or generated data, such as network data or data specific to the network devices themselves. Network devices may also include sensors that monitor their environment or other devices to collect data regarding that environment or those devices, and such network devices may provide data they collect over time. Network devices may also include devices within the internet of things, such as devices within a home automation network. Some of these devices may be referred to as edge devices, and may involve edge computing circuitry. Data may be transmitted by network devices directly to computing environment 114 or to network-attached data stores, such as network-attached data stores 110 for storage so that the data may be retrieved later by the computing environment 114 or other portions of data transmission network 100.

Data transmission network 100 may also include one or more network-attached data stores 110. Network-attached data stores 110 are used to store data to be processed by the computing environment 114 as well as any intermediate or final data generated by the computing system in non-volatile memory. However in certain embodiments, the configuration of the computing environment 114 allows its operations to be performed such that intermediate and final data results can be stored solely in volatile memory (e.g., RAM), without a requirement that intermediate or final data results be stored to non-volatile types of memory (e.g., disk). This can be useful in certain situations, such as when the computing environment 114 receives ad hoc queries from a user and when responses, which are generated by processing large amounts of data, need to be generated on-the-fly. In this non-limiting situation, the computing environment 114 may be configured to retain the processed information within memory so that responses can be generated for the user at different levels of detail as well as allow a user to interactively query against this information.

Network-attached data stores may store a variety of different types of data organized in a variety of different ways and from a variety of different sources. For example, network-attached data storage may include storage other than primary storage located within computing environment 114 that is directly accessible by processors located therein. Network-attached data storage may include secondary, tertiary or auxiliary storage, such as large hard drives, servers, virtual memory, among other types. Storage devices may include portable or non-portable storage devices, optical storage devices, and various other mediums capable of storing, containing data. A machine-readable storage medium or computer-readable storage medium may include a non-transitory medium in which data can be stored and that does not include carrier waves and/or transitory electronic signals. Examples of a non-transitory medium may include, for example, a magnetic disk or tape, optical storage media such as compact disk or digital versatile disk, flash memory, memory or memory devices. A computer-program product may include code and/or machine-executable instructions that may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, among others. Furthermore, the data stores may hold a variety of different types of data. For example, network-attached data stores 110 may hold unstructured (e.g., raw) data, such as manufacturing data (e.g., a database containing records identifying products being manufactured with parameter data for each product, such as colors and models) or product sales databases (e.g., a database containing individual data records identifying details of individual product sales).

The unstructured data may be presented to the computing environment 114 in different forms such as a flat file or a conglomerate of data records, and may have data values and accompanying time stamps. The computing environment 114 may be used to analyze the unstructured data in a variety of ways to determine the best way to structure (e.g., hierarchically) that data, such that the structured data is tailored to a type of further analysis that a user wishes to perform on the data. For example, after being processed, the unstructured time stamped data may be aggregated by time (e.g., into daily time period units) to generate time series data and/or structured hierarchically according to one or more dimensions (e.g., parameters, attributes, and/or variables). For example, data may be stored in a hierarchical data structure, such as a ROLAP OR MOLAP database, or may be stored in another tabular form, such as in a flat-hierarchy form.

Data transmission network 100 may also include one or more server farms 106. Computing environment 114 may route select communications or data to the one or more sever farms 106 or one or more servers within the server farms. Server farms 106 can be configured to provide information in a predetermined manner. For example, server farms 106 may access data to transmit in response to a communication. Server farms 106 may be separately housed from each other device within data transmission network 100, such as computing environment 114, and/or may be part of a device or system.

Server farms 106 may host a variety of different types of data processing as part of data transmission network 100. Server farms 106 may receive a variety of different data from network devices, from computing environment 114, from cloud network 116, or from other sources. The data may have been obtained or collected from one or more sensors, as inputs from a control database, or may have been received as inputs from an external system or device. Server farms 106 may assist in processing the data by turning raw data into processed data based on one or more rules implemented by the server farms. For example, sensor data may be analyzed to determine changes in an environment over time or in real-time.

Data transmission network 100 may also include one or more cloud networks 116. Cloud network 116 may include a cloud infrastructure system that provides cloud services. In certain embodiments, services provided by the cloud network 116 may include a host of services that are made available to users of the cloud infrastructure system on demand. Cloud network 116 is shown in FIG. 1 as being connected to computing environment 114 (and therefore having computing environment 114 as its client or user), but cloud network 116 may be connected to or utilized by any of the devices in FIG. 1. Services provided by the cloud network can dynamically scale to meet the needs of its users. The cloud network 116 may include one or more computers, servers, and/or systems. In some embodiments, the computers, servers, and/or systems that make up the cloud network 116 are different from the user's own on-premises computers, servers, and/or systems. For example, the cloud network 116 may host an application, and a user may, via a communication network such as the Internet, on demand, order and use the application.

While each device, server and system in FIG. 1 is shown as a single device, it will be appreciated that multiple devices may instead be used. For example, a set of network devices can be used to transmit various communications from a single user, or remote server 140 may include a server stack. As another example, data may be processed as part of computing environment 114.

Each communication within data transmission network 100 (e.g., between client devices, between a device and connection management system 150, between servers 106 and computing environment 114 or between a server and a device) may occur over one or more networks 108. Networks 108 may include one or more of a variety of different types of networks, including a wireless network, a wired network, or a combination of a wired and wireless network. Examples of suitable networks include the Internet, a personal area network, a local area network (LAN), a wide area network (WAN), or a wireless local area network (WLAN). A wireless network may include a wireless interface or combination of wireless interfaces. As an example, a network in the one or more networks 108 may include a short-range communication channel, such as a Bluetooth or a Bluetooth Low Energy channel. A wired network may include a wired interface. The wired and/or wireless networks may be implemented using routers, access points, bridges, gateways, or the like, to connect devices in the network 108, as will be further described with respect to FIG. 2. The one or more networks 108 can be incorporated entirely within or can include an intranet, an extranet, or a combination thereof. In one embodiment, communications between two or more systems and/or devices can be achieved by a secure communications protocol, such as secure sockets layer (SSL) or transport layer security (TLS). In addition, data and/or transactional details may be encrypted.

Some aspects may utilize the Internet of Things (IoT), where things (e.g., machines, devices, phones, sensors) can be connected to networks and the data from these things can be collected and processed within the things and/or external to the things. For example, the IoT can include sensors in many different devices, and high value analytics can be applied to identify hidden relationships and drive increased efficiencies. This can apply to both big data analytics and real-time (e.g., ESP) analytics. IoT may be implemented in various areas, such as for access (technologies that get data and move it), embed-ability (devices with embedded sensors), and services. Industries in the IoT space may include automotive (connected car), manufacturing (connected factory), smart cities, energy and retail. This will be described further below with respect to FIG. 2.

As noted, computing environment 114 may include a communications grid 120 and a transmission network database system 118. Communications grid 120 may be a grid-based computing system for processing large amounts of data. The transmission network database system 118 may be for managing, storing, and retrieving large amounts of data that are distributed to and stored in the one or more network-attached data stores 110 or other data stores that reside at different locations within the transmission network database system 118. The compute nodes in the grid-based computing system 120 and the transmission network database system 118 may share the same processor hardware, such as processors that are located within computing environment 114.

Figure 2:
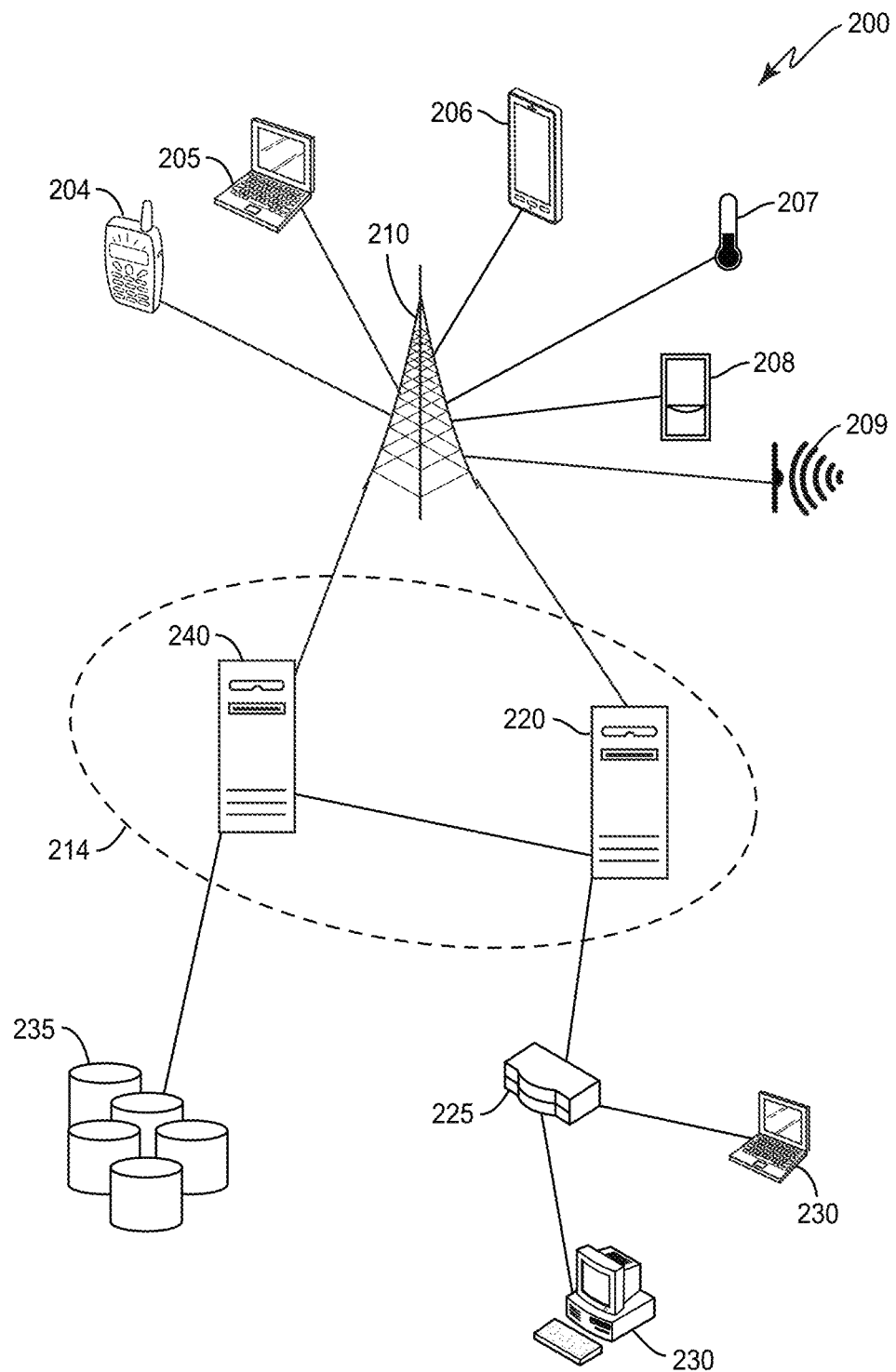
FIG. 2 illustrates an example network including an example set of devices communicating with each other over an exchange system and via a network, according to at least one embodiment of the present technology.

FIG. 2 illustrates an example network including an example set of devices communicating with each other over an exchange system and via a network, according to embodiments of the present technology. As noted, each communication within data transmission network 100 may occur over one or more networks. System 200 includes a network device 204 configured to communicate with a variety of types of client devices, for example client devices 230, over a variety of types of communication channels.

As shown in FIG. 2, network device 204 can transmit a communication over a network (e.g., a cellular network via a base station 210). The communication can be routed to another network device, such as network devices 205-209, via base station 210. The communication can also be routed to computing environment 214 via base station 210. For example, network device 204 may collect data either from its surrounding environment or from other network devices (such as network devices 205-209) and transmit that data to computing environment 214.

Although network devices 204-209 are shown in FIG. 2 as a mobile phone, laptop computer, tablet computer, temperature sensor, motion sensor, and audio sensor respectively, the network devices may be or include sensors that are sensitive to detecting aspects of their environment. For example, the network devices may include sensors such as water sensors, power sensors, electrical current sensors, chemical sensors, optical sensors, pressure sensors, geographic or position sensors (e.g., GPS), velocity sensors, acceleration sensors, flow rate sensors, among others. Examples of characteristics that may be sensed include force, torque, load, strain, position, temperature, air pressure, fluid flow, chemical properties, resistance, electromagnetic fields, radiation, irradiance, proximity, acoustics, moisture, distance, speed, vibrations, acceleration, electrical potential, electrical current, among others. The sensors may be mounted to various components used as part of a variety of different types of systems (e.g., an oil drilling operation). The network devices may detect and record data related to the environment that it monitors, and transmit that data to computing environment 214.

As noted, one type of system that may include various sensors that collect data to be processed and/or transmitted to a computing environment according to certain embodiments includes an oil drilling system. For example, the one or more drilling operation sensors may include surface sensors that measure a hook load, a fluid rate, a temperature and a density in and out of the wellbore, a standpipe pressure, a surface torque, a rotation speed of a drill pipe, a rate of penetration, a mechanical specific energy, etc. and downhole sensors that measure a rotation speed of a bit, fluid densities, downhole torque, downhole vibration (axial, tangential, lateral), a weight applied at a drill bit, an annular pressure, a differential pressure, an azimuth, an inclination, a dog leg severity, a measured depth, a vertical depth, a downhole temperature, etc. Besides the raw data collected directly by the sensors, other data may include parameters either developed by the sensors or assigned to the system by a client or other controlling device. For example, one or more drilling operation control parameters may control settings such as a mud motor speed to flow ratio, a bit diameter, a predicted formation top, seismic data, weather data, etc. Other data may be generated using physical models such as an earth model, a weather model, a seismic model, a bottom hole assembly model, a well plan model, an annular friction model, etc. In addition to sensor and control settings, predicted outputs, of for example, the rate of penetration, mechanical specific energy, hook load, flow in fluid rate, flow out fluid rate, pump pressure, surface torque, rotation speed of the drill pipe, annular pressure, annular friction pressure, annular temperature, equivalent circulating density, etc. may also be stored in the data warehouse.

In another example, another type of system that may include various sensors that collect data to be processed and/or transmitted to a computing environment according to certain embodiments includes a home automation or similar automated network in a different environment, such as an office space, school, public space, sports venue, or a variety of other locations. Network devices in such an automated network may include network devices that allow a user to access, control, and/or configure various home appliances located within the user's home (e.g., a television, radio, light, fan, humidifier, sensor, microwave, iron, and/or the like), or outside of the user's home (e.g., exterior motion sensors, exterior lighting, garage door openers, sprinkler systems, or the like). For example, network device 102 may include a home automation switch that may be coupled with a home appliance. In another embodiment, a network device can allow a user to access, control, and/or configure devices, such as office-related devices (e.g., copy machine, printer, or fax machine), audio and/or video related devices (e.g., a receiver, a speaker, a projector, a DVD player, or a television), media-playback devices (e.g., a compact disc player, a CD player, or the like), computing devices (e.g., a home computer, a laptop computer, a tablet, a personal digital assistant (PDA), a computing device, or a wearable device), lighting devices (e.g., a lamp or recessed lighting), devices associated with a security system, devices associated with an alarm system, devices that can be operated in an automobile (e.g., radio devices, navigation devices), and/or the like. Data may be collected from such various sensors in raw form, or data may be processed by the sensors to create parameters or other data either developed by the sensors based on the raw data or assigned to the system by a client or other controlling device.

In another example, another type of system that may include various sensors that collect data to be processed and/or transmitted to a computing environment according to certain embodiments includes a power or energy grid. A variety of different network devices may be included in an energy grid, such as various devices within one or more power plants, energy farms (e.g., wind farm, solar farm, among others) energy storage facilities, factories, homes and businesses of consumers, among others. One or more of such devices may include one or more sensors that detect energy gain or loss, electrical input or output or loss, and a variety of other efficiencies. These sensors may collect data to inform users of how the energy grid, and individual devices within the grid, may be functioning and how they may be made more efficient.

Network device sensors may also perform processing on data it collects before transmitting the data to the computing environment 114, or before deciding whether to transmit data to the computing environment 114. For example, network devices may determine whether data collected meets certain rules, for example by comparing data or values calculated from the data and comparing that data to one or more thresholds. The network device may use this data and/or comparisons to determine if the data should be transmitted to the computing environment 214 for further use or processing.

Computing environment 214 may include machines 220 and 240. Although computing environment 214 is shown in FIG. 2 as having two machines, 220 and 240, computing environment 214 may have only one machine or may have more than two machines. The machines that make up computing environment 214 may include specialized computers, servers, or other machines that are configured to individually and/or collectively process large amounts of data. The computing environment 214 may also include storage devices that include one or more databases of structured data, such as data organized in one or more hierarchies, or unstructured data. The databases may communicate with the processing devices within computing environment 214 to distribute data to them. Since network devices may transmit data to computing environment 214, that data may be received by the computing environment 214 and subsequently stored within those storage devices. Data used by computing environment 214 may also be stored in data stores 235, which may also be a part of or connected to computing environment 214.

Computing environment 214 can communicate with various devices via one or more routers 225 or other inter-network or intra-network connection components. For example, computing environment 214 may communicate with devices 230 via one or more routers 225. Computing environment 214 may collect, analyze and/or store data from or pertaining to communications, client device operations, client rules, and/or user-associated actions stored at one or more data stores 235. Such data may influence communication routing to the devices within computing environment 214, how data is stored or processed within computing environment 214, among other actions.

Notably, various other devices can further be used to influence communication routing and/or processing between devices within computing environment 214 and with devices outside of computing environment 214. For example, as shown in FIG. 2, computing environment 214 may include a web server 240. Thus, computing environment 214 can retrieve data of interest, such as client information (e.g., product information, client rules, etc.), technical product details, news, current or predicted weather, and so on.

In addition to computing environment 214 collecting data (e.g., as received from network devices, such as sensors, and client devices or other sources) to be processed as part of a big data analytics project, it may also receive data in real time as part of a streaming analytics environment. As noted, data may be collected using a variety of sources as communicated via different kinds of networks or locally. Such data may be received on a real-time streaming basis. For example, network devices may receive data periodically from network device sensors as the sensors continuously sense, monitor and track changes in their environments. Devices within computing environment 214 may also perform pre-analysis on data it receives to determine if the data received should be processed as part of an ongoing project. The data received and collected by computing environment 214, no matter what the source or method or timing of receipt, may be processed over a period of time for a client to determine results data based on the client's needs and rules.

Figure 3:
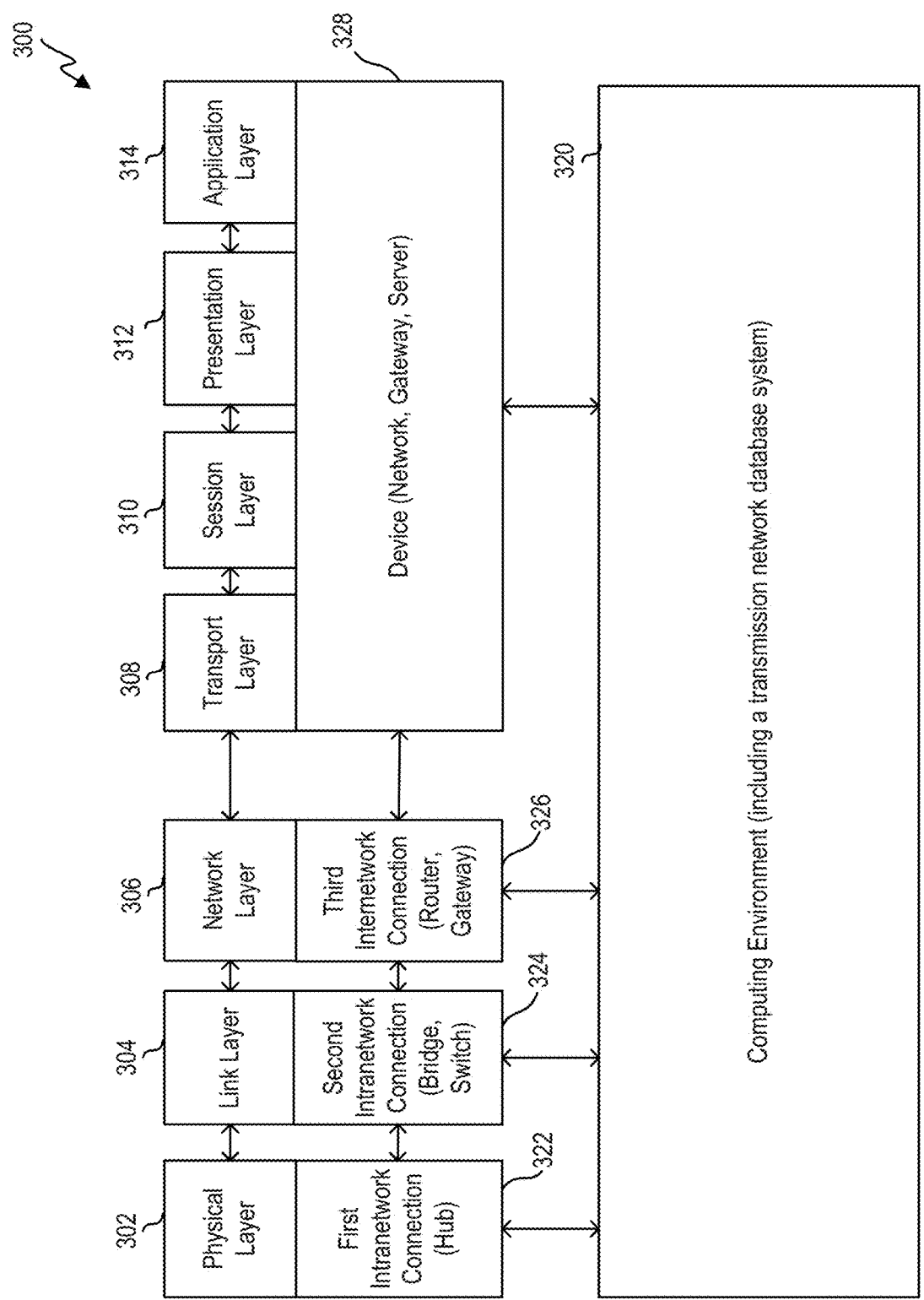
FIG. 3 illustrates a representation of a conceptual model of a communications protocol system, according to at least one embodiment of the present technology.

FIG. 3 illustrates a representation of a conceptual model of a communications protocol system, according to embodiments of the present technology. More specifically, FIG. 3 identifies operation of a computing environment in an Open Systems Interaction model that corresponds to various connection components. The model 300 shows, for example, how a computing environment, such as computing environment 320 (or computing environment 214 in FIG. 2) may communicate with other devices in its network, and control how communications between the computing environment and other devices are executed and under what conditions.

The model can include layers 302-314. The layers are arranged in a stack. Each layer in the stack serves the layer one level higher than it (except for the application layer, which is the highest layer), and is served by the layer one level below it (except for the physical layer, which is the lowest layer). The physical layer is the lowest layer because it receives and transmits raw bytes of data and is the farthest layer from the user in a communications system. On the other hand, the application layer is the highest layer because it interacts directly with a software application.

As noted, the model includes a physical layer 302. Physical layer 302 represents physical communication and can define parameters of that physical communication. For example, such physical communication may come in the form of electrical, optical, or electromagnetic signals. Physical layer 302 also defines protocols that may control communications within a data transmission network.

Link layer 304 defines links and mechanisms used to transmit (i.e., move) data across a network. The link layer manages node-to-node communications, such as within a grid computing environment. Link layer 304 can detect and correct errors (e.g., transmission errors in the physical layer 302). Link layer 304 can also include a media access control (MAC) layer and logical link control (LLC) layer.

Network layer 306 defines the protocol for routing within a network. In other words, the network layer coordinates transferring data across nodes in a same network (e.g., such as a grid computing environment). Network layer 306 can also define the processes used to structure local addressing within the network.

Transport layer 308 can manage the transmission of data and the quality of the transmission and/or receipt of that data. Transport layer 308 can provide a protocol for transferring data, such as, for example, a Transmission Control Protocol (TCP). Transport layer 308 can assemble and disassemble data frames for transmission. The transport layer can also detect transmission errors occurring in the layers below it.

Session layer 310 can establish, maintain, and manage communication connections between devices on a network. In other words, the session layer controls the dialogues or nature of communications between network devices on the network. The session layer may also establish checkpointing, adjournment, termination, and restart procedures.

Presentation layer 312 can provide translation for communications between the application and network layers. In other words, this layer may encrypt, decrypt and/or format data based on data types known to be accepted by an application or network layer.

Application layer 314 interacts directly with software applications and end users, and manages communications between them. Application layer 314 can identify destinations, local resource states or availability and/or communication content or formatting using the applications.

Intra-network connection components 322 and 324 are shown to operate in lower levels, such as physical layer 302 and link layer 304, respectively. For example, a hub can operate in the physical layer and a switch can operate in the link layer. Inter-network connection components 326 and 328 are shown to operate on higher levels, such as layers 306-314. For example, routers can operate in the network layer and network devices can operate in the transport, session, presentation, and application layers.

As noted, a computing environment 320 can interact with and/or operate on, in various embodiments, one, more, all or any of the various layers. For example, computing environment 320 can interact with a hub (e.g., via the link layer) so as to adjust which devices the hub communicates with. The physical layer may be served by the link layer, so it may implement such data from the link layer. For example, the computing environment 320 may control which devices it will receive data from. For example, if the computing environment 320 knows that a certain network device has turned off, broken, or otherwise become unavailable or unreliable, the computing environment 320 may instruct the hub to prevent any data from being transmitted to the computing environment 320 from that network device. Such a process may be beneficial to avoid receiving data that is inaccurate or that has been influenced by an uncontrolled environment. As another example, computing environment 320 can communicate with a bridge, switch, router or gateway and influence which device within the system (e.g., system 200) the component selects as a destination. In some embodiments, computing environment 320 can interact with various layers by exchanging communications with equipment operating on a particular layer by routing or modifying existing communications. In another embodiment, such as in a grid computing environment, a node may determine how data within the environment should be routed (e.g., which node should receive certain data) based on certain parameters or information provided by other layers within the model.

As noted, the computing environment 320 may be a part of a communications grid environment, the communications of which may be implemented as shown in the protocol of FIG. 3. For example, referring back to FIG. 2, one or more of machines 220 and 240 may be part of a communications grid computing environment. A gridded computing environment may be employed in a distributed system with non-interactive workloads where data resides in memory on the machines, or compute nodes. In such an environment, analytic code, instead of a database management system, controls the processing performed by the nodes. Data is co-located by pre-distributing it to the grid nodes, and the analytic code on each node loads the local data into memory. Each node may be assigned a particular task such as a portion of a processing project, or to organize or control other nodes within the grid.

Figure 4:
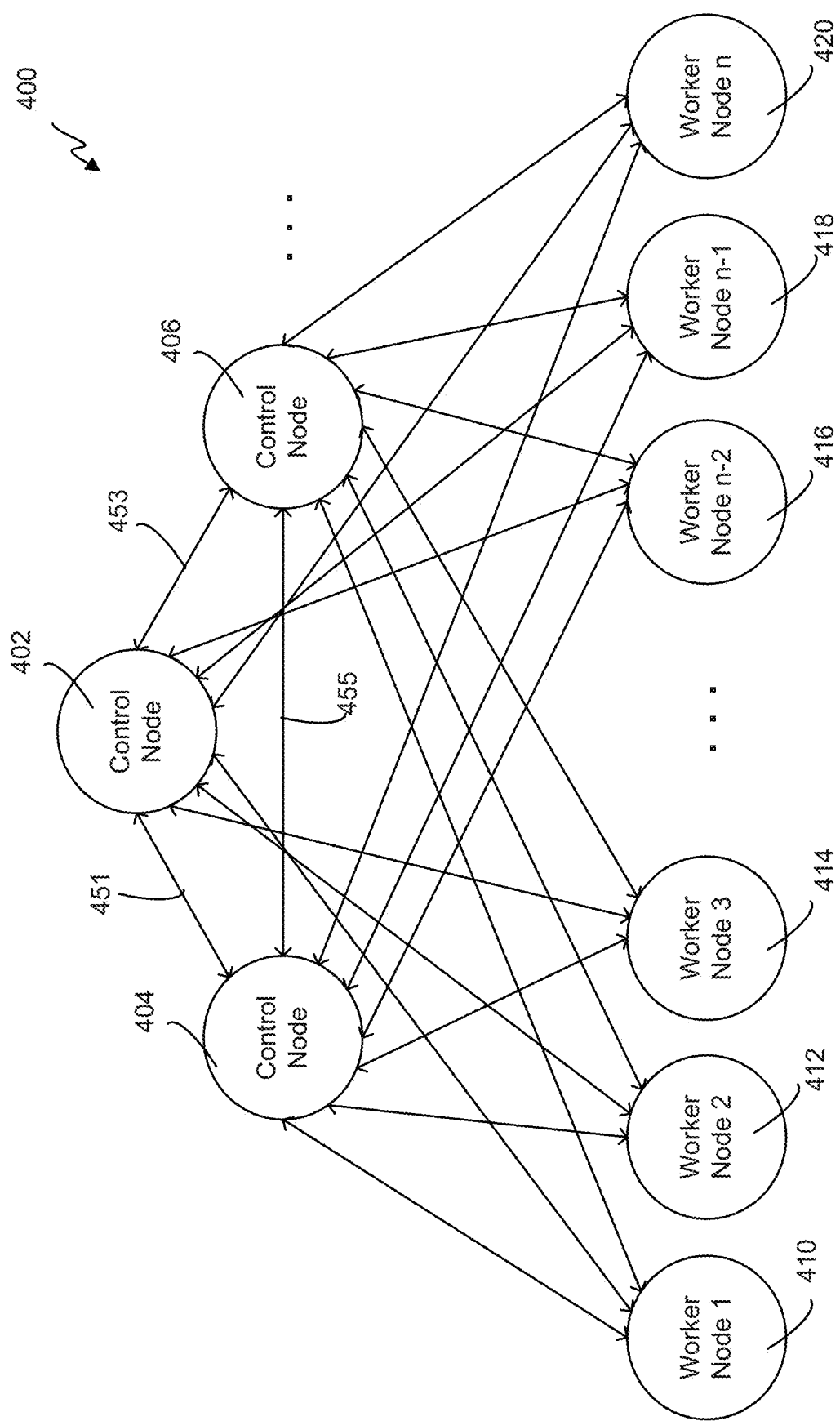
FIG. 4 illustrates a communications grid computing system including a variety of control and worker nodes, according to at least one embodiment of the present technology.

FIG. 4 illustrates a communications grid computing system 400 including a variety of control and worker nodes, according to embodiments of the present technology. Communications grid computing system 400 includes three control nodes and one or more worker nodes. Communications grid computing system 400 includes control nodes 402, 404, and 406. The control nodes are communicatively connected via communication paths 451, 453, and 455. Therefore, the control nodes may transmit information (e.g., related to the communications grid or notifications), to and receive information from each other. Although communications grid computing system 400 is shown in FIG. 4 as including three control nodes, the communications grid may include more or less than three control nodes.

Communications grid computing system (or just "communications grid") 400 also includes one or more worker nodes. Shown in FIG. 4 are six worker nodes 410-420. Although FIG. 4 shows six worker nodes, a communications grid according to embodiments of the present technology may include more or less than six worker nodes. The number of worker nodes included in a communications grid may be dependent upon how large the project or data set is being processed by the communications grid, the capacity of each worker node, the time designated for the communications grid to complete the project, among others. Each worker node within the communications grid 400 may be connected (wired or wirelessly, and directly or indirectly) to control nodes 402-406. Therefore, each worker node may receive information from the control nodes (e.g., an instruction to perform work on a project) and may transmit information to the control nodes (e.g., a result from work performed on a project). Furthermore, worker nodes may communicate with each other (either directly or indirectly). For example, worker nodes may transmit data between each other related to a job being performed or an individual task within a job being performed by that worker node. However, in certain embodiments, worker nodes may not, for example, be connected (communicatively or otherwise) to certain other worker nodes. In an embodiment, worker nodes may only be able to communicate with the control node that controls it, and may not be able to communicate with other worker nodes in the communications grid, whether they are other worker nodes controlled by the control node that controls the worker node, or worker nodes that are controlled by other control nodes in the communications grid.

A control node may connect with an external device with which the control node may communicate (e.g., a grid user, such as a server or computer, may connect to a controller of the grid). For example, a server or computer may connect to control nodes and may transmit a project or job to the node. The project may include a data set. The data set may be of any size. Once the control node receives such a project including a large data set, the control node may distribute the data set or projects related to the data set to be performed by worker nodes. Alternatively, for a project including a large data set, the data set may be received or stored by a machine other than a control node (e.g., a Hadoop data node).

Control nodes may maintain knowledge of the status of the nodes in the grid (i.e., grid status information), accept work requests from clients, subdivide the work across worker nodes, coordinate the worker nodes, among other responsibilities. Worker nodes may accept work requests from a control node and provide the control node with results of the work performed by the worker node. A grid may be started from a single node (e.g., a machine, computer, server, etc.). This first node may be assigned or may start as the primary control node that will control any additional nodes that enter the grid.

When a project is submitted for execution (e.g., by a client or a controller of the grid) it may be assigned to a set of nodes. After the nodes are assigned to a project, a data structure (i.e., a communicator) may be created. The communicator may be used by the project for information to be shared between the project code running on each node. A communication handle may be created on each node. A handle, for example, is a reference to the communicator that is valid within a single process on a single node, and the handle may be used when requesting communications between nodes.

A control node, such as control node 402, may be designated as the primary control node. A server, computer or other external device may connect to the primary control node. Once the control node receives a project, the primary control node may distribute portions of the project to its worker nodes for execution. For example, when a project is initiated on communications grid 400, primary control node 402 controls the work to be performed for the project in order to complete the project as requested or instructed. The primary control node may distribute work to the worker nodes based on various factors, such as which subsets or portions of projects may be completed most efficiently and in the correct amount of time. For example, a worker node may perform analysis on a portion of data that is already local (e.g., stored on) the worker node. The primary control node also coordinates and processes the results of the work performed by each worker node after each worker node executes and completes its job. For example, the primary control node may receive a result from one or more worker nodes, and the control node may organize (e.g., collect and assemble) the results received and compile them to produce a complete result for the project received from the end user.

Any remaining control nodes, such as control nodes 404 and 406, may be assigned as backup control nodes for the project. In an embodiment, backup control nodes may not control any portion of the project. Instead, backup control nodes may serve as a backup for the primary control node and take over as primary control node if the primary control node were to fail. If a communications grid were to include only a single control node, and the control node were to fail (e.g., the control node is shut off or breaks) then the communications grid as a whole may fail and any project or job being run on the communications grid may fail and may not complete. While the project may be run again, such a failure may cause a delay (severe delay in some cases, such as overnight delay) in completion of the project. Therefore, a grid with multiple control nodes, including a backup control node, may be beneficial.

To add another node or machine to the grid, the primary control node may open a pair of listening sockets, for example. A socket may be used to accept work requests from clients, and the second socket may be used to accept connections from other grid nodes. The primary control node may be provided with a list of other nodes (e.g., other machines, computers, servers) that will participate in the grid, and the role that each node will fill in the grid. Upon startup of the primary control node (e.g., the first node on the grid), the primary control node may use a network protocol to start the server process on every other node in the grid. Command line parameters, for example, may inform each node of one or more pieces of information, such as: the role that the node will have in the grid, the host name of the primary control node, the port number on which the primary control node is accepting connections from peer nodes, among others. The information may also be provided in a configuration file, transmitted over a secure shell tunnel, recovered from a configuration server, among others. While the other machines in the grid may not initially know about the configuration of the grid, that information may also be sent to each other node by the primary control node. Updates of the grid information may also be subsequently sent to those nodes.

For any control node other than the primary control node added to the grid, the control node may open three sockets. The first socket may accept work requests from clients, the second socket may accept connections from other grid members, and the third socket may connect (e.g., permanently) to the primary control node. When a control node (e.g., primary control node) receives a connection from another control node, it first checks to see if the peer node is in the list of configured nodes in the grid. If it is not on the list, the control node may clear the connection. If it is on the list, it may then attempt to authenticate the connection. If authentication is successful, the authenticating node may transmit information to its peer, such as the port number on which a node is listening for connections, the host name of the node, information about how to authenticate the node, among other information. When a node, such as the new control node, receives information about another active node, it will check to see if it already has a connection to that other node. If it does not have a connection to that node, it may then establish a connection to that control node.

Any worker node added to the grid may establish a connection to the primary control node and any other control nodes on the grid. After establishing the connection, it may authenticate itself to the grid (e.g., any control nodes, including both primary and backup, or a server or user controlling the grid). After successful authentication, the worker node may accept configuration information from the control node.

When a node joins a communications grid (e.g., when the node is powered on or connected to an existing node on the grid or both), the node is assigned (e.g., by an operating system of the grid) a universally unique identifier (UUID). This unique identifier may help other nodes and external entities (devices, users, etc.) to identify the node and distinguish it from other nodes. When a node is connected to the grid, the node may share its unique identifier with the other nodes in the grid. Since each node may share its unique identifier, each node may know the unique identifier of every other node on the grid. Unique identifiers may also designate a hierarchy of each of the nodes (e.g., backup control nodes) within the grid. For example, the unique identifiers of each of the backup control nodes may be stored in a list of backup control nodes to indicate an order in which the backup control nodes will take over for a failed primary control node to become a new primary control node. However, a hierarchy of nodes may also be determined using methods other than using the unique identifiers of the nodes. For example, the hierarchy may be predetermined, or may be assigned based on other predetermined factors.

The grid may add new machines at any time (e.g., initiated from any control node). Upon adding a new node to the grid, the control node may first add the new node to its table of grid nodes. The control node may also then notify every other control node about the new node. The nodes receiving the notification may acknowledge that they have updated their configuration information.

Primary control node 402 may, for example, transmit one or more communications to backup control nodes 404 and 406 (and, for example, to other control or worker nodes within the communications grid). Such communications may sent periodically, at fixed time intervals, between known fixed stages of the project's execution, among other protocols. The communications transmitted by primary control node 402 may be of varied types and may include a variety of types of information. For example, primary control node 402 may transmit snapshots (e.g., status information) of the communications grid so that backup control node 404 always has a recent snapshot of the communications grid. The snapshot or grid status may include, for example, the structure of the grid (including, for example, the worker nodes in the grid, unique identifiers of the nodes, or their relationships with the primary control node) and the status of a project (including, for example, the status of each worker node's portion of the project). The snapshot may also include analysis or results received from worker nodes in the communications grid. The backup control nodes may receive and store the backup data received from the primary control node. The backup control nodes may transmit a request for such a snapshot (or other information) from the primary control node, or the primary control node may send such information periodically to the backup control nodes.

As noted, the backup data may allow the backup control node to take over as primary control node if the primary control node fails without requiring the grid to start the project over from scratch. If the primary control node fails, the backup control node that will take over as primary control node may retrieve the most recent version of the snapshot received from the primary control node and use the snapshot to continue the project from the stage of the project indicated by the backup data. This may prevent failure of the project as a whole.

A backup control node may use various methods to determine that the primary control node has failed. In one example of such a method, the primary control node may transmit (e.g., periodically) a communication to the backup control node that indicates that the primary control node is working and has not failed, such as a heartbeat communication. The backup control node may determine that the primary control node has failed if the backup control node has not received a heartbeat communication for a certain predetermined period of time. Alternatively, a backup control node may also receive a communication from the primary control node itself (before it failed) or from a worker node that the primary control node has failed, for example because the primary control node has failed to communicate with the worker node.

Different methods may be performed to determine which backup control node of a set of backup control nodes (e.g., backup control nodes 404 and 406) will take over for failed primary control node 402 and become the new primary control node. For example, the new primary control node may be chosen based on a ranking or "hierarchy" of backup control nodes based on their unique identifiers. In an alternative embodiment, a backup control node may be assigned to be the new primary control node by another device in the communications grid or from an external device (e.g., a system infrastructure or an end user, such as a server or computer, controlling the communications grid). In another alternative embodiment, the backup control node that takes over as the new primary control node may be designated based on bandwidth or other statistics about the communications grid.

A worker node within the communications grid may also fail. If a worker node fails, work being performed by the failed worker node may be redistributed amongst the operational worker nodes. In an alternative embodiment, the primary control node may transmit a communication to each of the operable worker nodes still on the communications grid that each of the worker nodes should purposefully fail also. After each of the worker nodes fail, they may each retrieve their most recent saved checkpoint of their status and re-start the project from that checkpoint to minimize lost progress on the project being executed.

Figure 5:
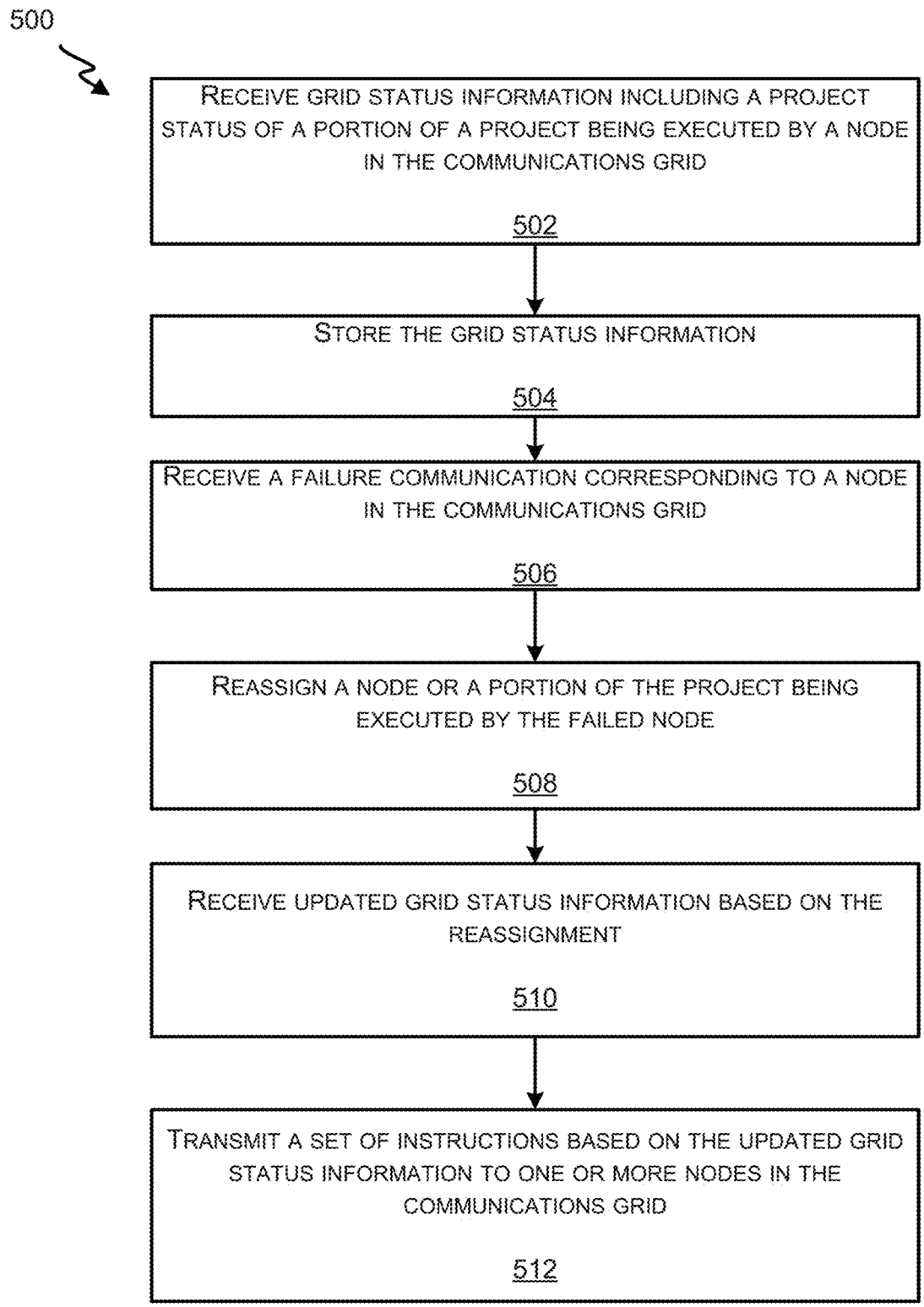
FIG. 5 illustrates a flow chart showing an example process for adjusting a communications grid or a work project in a communications grid after a failure of a node, according to at least one embodiment of the present technology.

FIG. 5 illustrates a flow chart showing an example process for adjusting a communications grid or a work project in a communications grid after a failure of a node, according to embodiments of the present technology. The process may include, for example, receiving grid status information including a project status of a portion of a project being executed by a node in the communications grid, as described in operation 502. For example, a control node (e.g., a backup control node connected to a primary control node and a worker node on a communications grid) may receive grid status information, where the grid status information includes a project status of the primary control node or a project status of the worker node. The project status of the primary control node and the project status of the worker node may include a status of one or more portions of a project being executed by the primary and worker nodes in the communications grid. The process may also include storing the grid status information, as described in operation 504. For example, a control node (e.g., a backup control node) may store the received grid status information locally within the control node. Alternatively, the grid status information may be sent to another device for storage where the control node may have access to the information.

The process may also include receiving a failure communication corresponding to a node in the communications grid in operation 506. For example, a node may receive a failure communication including an indication that the primary control node has failed, prompting a backup control node to take over for the primary control node. In an alternative embodiment, a node may receive a failure that a worker node has failed, prompting a control node to reassign the work being performed by the worker node. The process may also include reassigning a node or a portion of the project being executed by the failed node, as described in operation 508. For example, a control node may designate the backup control node as a new primary control node based on the failure communication upon receiving the failure communication. If the failed node is a worker node, a control node may identify a project status of the failed worker node using the snapshot of the communications grid, where the project status of the failed worker node includes a status of a portion of the project being executed by the failed worker node at the failure time.

The process may also include receiving updated grid status information based on the reassignment, as described in operation 510, and transmitting a set of instructions based on the updated grid status information to one or more nodes in the communications grid, as described in operation 512. The updated grid status information may include an updated project status of the primary control node or an updated project status of the worker node. The updated information may be transmitted to the other nodes in the grid to update their stale stored information.

Figure 6:
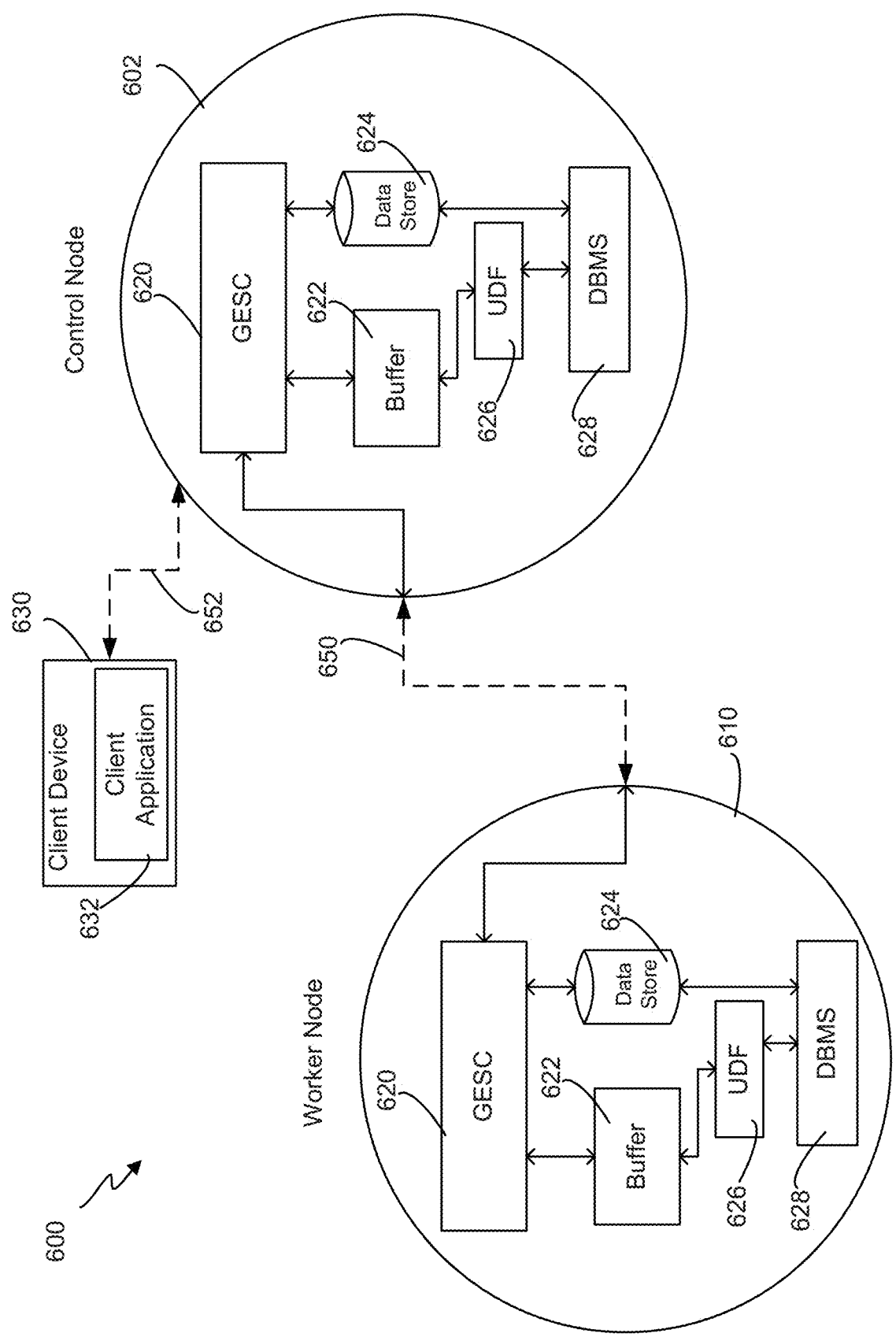
FIG. 6 illustrates a portion of a communications grid computing system including a control node and a worker node, according to at least one embodiment of the present technology.

FIG. 6 illustrates a portion of a communications grid computing system 600 including a control node and a worker node, according to embodiments of the present technology. Communications grid 600 computing system includes one control node (control node 602) and one worker node (worker node 610) for purposes of illustration, but may include more worker and/or control nodes. The control node 602 is communicatively connected to worker node 610 via communication path 650. Therefore, control node 602 may transmit information (e.g., related to the communications grid or notifications), to and receive information from worker node 610 via path 650.

Similar to in FIG. 4, communications grid computing system (or just "communications grid") 600 includes data processing nodes (control node 602 and worker node 610). Nodes 602 and 610 include multi-core data processors. Each node 602 and 610 includes a grid-enabled software component (GESC) 620 that executes on the data processor associated with that node and interfaces with buffer memory 622 also associated with that node. Each node 602 and 610 includes a database management software (DBMS) 628 that executes on a database server (not shown) at control node 602 and on a database server (not shown) at worker node 610.

Each node also includes a data store 624. Data stores 624, similar to network-attached data stores 110 in FIG. 1 and data stores 235 in FIG. 2, are used to store data to be processed by the nodes in the computing environment. Data stores 624 may also store any intermediate or final data generated by the computing system after being processed, for example in non-volatile memory. However in certain embodiments, the configuration of the grid computing environment allows its operations to be performed such that intermediate and final data results can be stored solely in volatile memory (e.g., RAM), without a requirement that intermediate or final data results be stored to non-volatile types of memory. Storing such data in volatile memory may be useful in certain situations, such as when the grid receives queries (e.g., ad hoc) from a client and when responses, which are generated by processing large amounts of data, need to be generated quickly or on-the-fly. In such a situation, the grid may be configured to retain the data within memory so that responses can be generated at different levels of detail and so that a client may interactively query against this information.

Each node also includes a user-defined function (UDF) 626. The UDF provides a mechanism for the DBMS 628 to transfer data to or receive data from the database stored in the data stores 624 that are managed by the DBMS. For example, UDF 626 can be invoked by the DBMS to provide data to the GESC for processing. The UDF 626 may establish a socket connection (not shown) with the GESC to transfer the data. Alternatively, the UDF 626 can transfer data to the GESC by writing data to shared memory accessible by both the UDF and the GESC.

The GESC 620 at the nodes 602 and 610 may be connected via a network, such as network 108 shown in FIG. 1. Therefore, nodes 602 and 610 can communicate with each other via the network using a predetermined communication protocol such as, for example, the Message Passing Interface (MPI). Each GESC 620 can engage in point-to-point communication with the GESC at another node or in collective communication with multiple GESCs via the network. The GESC 620 at each node may contain identical (or nearly identical) software instructions. Each node may be capable of operating as either a control node or a worker node. The GESC at the control node 602 can communicate, over a communication path 652, with a client device 630. More specifically, control node 602 may communicate with client application 632 hosted by the client device 630 to receive queries and to respond to those queries after processing large amounts of data.

DBMS 628 may control the creation, maintenance, and use of database or data structure (not shown) within a nodes 602 or 610. The database may organize data stored in data stores 624. The DBMS 628 at control node 602 may accept requests for data and transfer the appropriate data for the request. With such a process, collections of data may be distributed across multiple physical locations. In this example, each node 602 and 610 stores a portion of the total data managed by the management system in its associated data store 624.

Furthermore, the DBMS may be responsible for protecting against data loss using replication techniques. Replication includes providing a backup copy of data stored on one node on one or more other nodes. Therefore, if one node fails, the data from the failed node can be recovered from a replicated copy residing at another node. However, as described herein with respect to FIG. 4, data or status information for each node in the communications grid may also be shared with each node on the grid.

Figure 7:
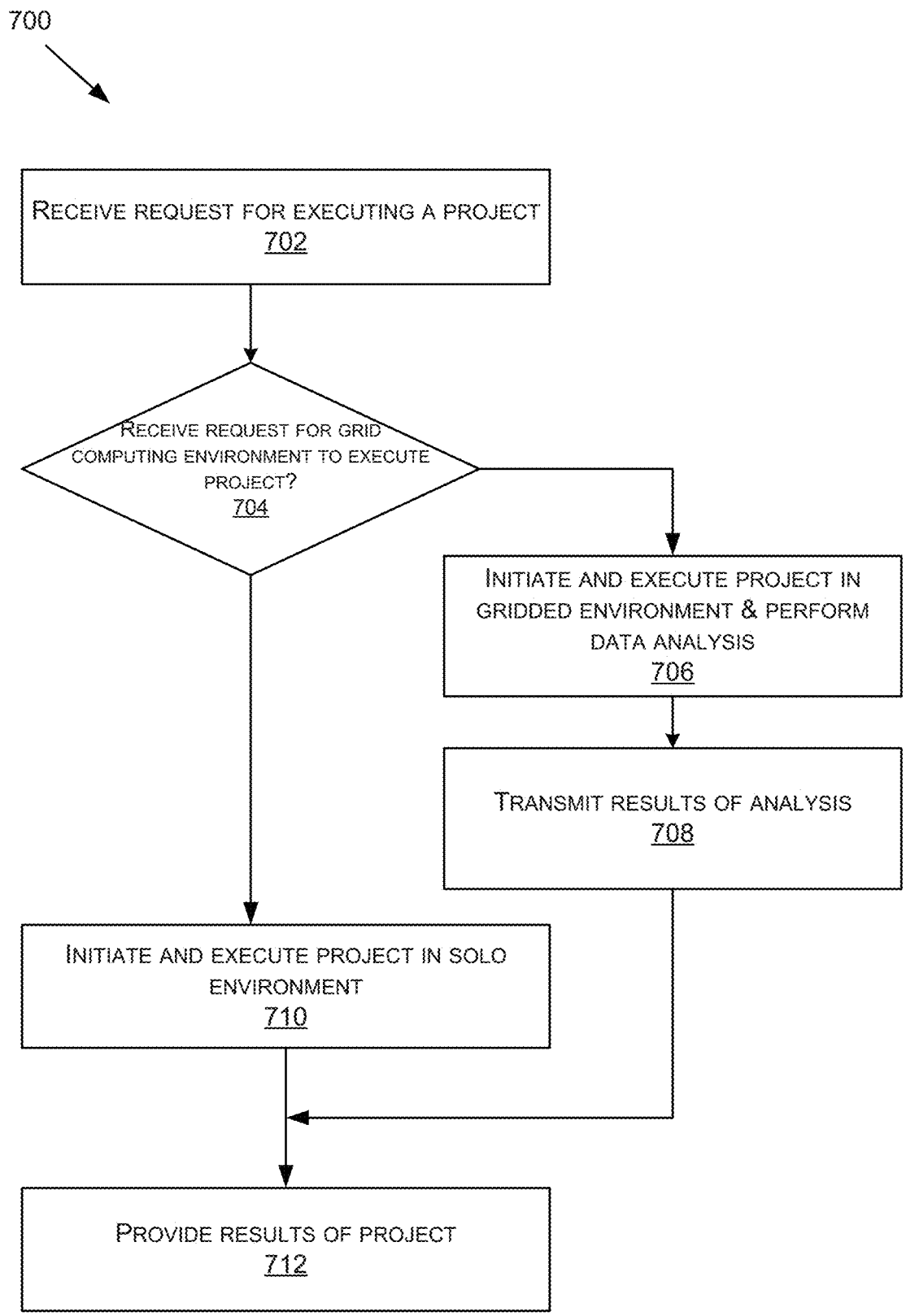
FIG. 7 illustrates a flow chart showing an example process for executing a data analysis or processing project, according to at least one embodiment of the present technology.

FIG. 7 illustrates a flow chart showing an example method for executing a project within a grid computing system, according to embodiments of the present technology. As described with respect to FIG. 6, the GESC at the control node may transmit data with a client device (e.g., client device 630) to receive queries for executing a project and to respond to those queries after large amounts of data have been processed. The query may be transmitted to the control node, where the query may include a request for executing a project, as described in operation 702. The query can contain instructions on the type of data analysis to be performed in the project and whether the project should be executed using the grid-based computing environment, as shown in operation 704.

To initiate the project, the control node may determine if the query requests use of the grid-based computing environment to execute the project. If the determination is no, then the control node initiates execution of the project in a solo environment (e.g., at the control node), as described in operation 710. If the determination is yes, the control node may initiate execution of the project in the grid-based computing environment, as described in operation 706. In such a situation, the request may include a requested configuration of the grid. For example, the request may include a number of control nodes and a number of worker nodes to be used in the grid when executing the project. After the project has been completed, the control node may transmit results of the analysis yielded by the grid, as described in operation 708. Whether the project is executed in a solo or grid-based environment, the control node provides the results of the project in operation 712.

As noted with respect to FIG. 2, the computing environments described herein may collect data (e.g., as received from network devices, such as sensors, such as network devices 204-209 in FIG. 2, and client devices or other sources) to be processed as part of a data analytics project, and data may be received in real time as part of a streaming analytics environment (e.g., ESP). Data may be collected using a variety of sources as communicated via different kinds of networks or locally, such as on a real-time streaming basis. For example, network devices may receive data periodically from network device sensors as the sensors continuously sense, monitor and track changes in their environments. More specifically, an increasing number of distributed applications develop or produce continuously flowing data from distributed sources by applying queries to the data before distributing the data to geographically distributed recipients. An event stream processing engine (ESPE) may continuously apply the queries to the data as it is received and determines which entities should receive the data. Client or other devices may also subscribe to the ESPE or other devices processing ESP data so that they can receive data after processing, based on for example the entities determined by the processing engine. For example, client devices 230 in FIG. 2 may subscribe to the ESPE in computing environment 214. In another example, event subscription devices 1024*a-c*, described further with respect to FIG. 10, may also subscribe to the ESPE. The ESPE may determine or define how input data or event streams from network devices or other publishers (e.g., network devices 204-209 in FIG. 2) are transformed into meaningful output data to be consumed by subscribers, such as for example client devices 230 in FIG. 2.

FIG. 8 illustrates a block diagram including components of an Event Stream Processing Engine (ESPE), according to embodiments of the present technology. ESPE 800 may include one or more projects 802. A project may be described as a second-level container in an engine model managed by ESPE 800 where a thread pool size for the project may be defined by a user. Each project of the one or more projects 802 may include one or more continuous queries 804 that contain data flows, which are data transformations of incoming event streams. The one or more continuous queries 804 may include one or more source windows 806 and one or more derived windows 808.

The ESPE may receive streaming data over a period of time related to certain events, such as events or other data sensed by one or more network devices. The ESPE may perform operations associated with processing data created by the one or more devices. For example, the ESPE may receive data from the one or more network devices 204-209 shown in FIG. 2. As noted, the network devices may include sensors that sense different aspects of their environments, and may collect data over time based on those sensed observations. For example, the ESPE may be implemented within one or more of machines 220 and 240 shown in FIG. 2. The ESPE may be implemented within such a machine by an ESP application. An ESP application may embed an ESPE with its own dedicated thread pool or pools into its application space where the main application thread can do application-specific work and the ESPE processes event streams at least by creating an instance of a model into processing objects.

The engine container is the top-level container in a model that manages the resources of the one or more projects 802. In an illustrative embodiment, for example, there may be only one ESPE 800 for each instance of the ESP application, and ESPE 800 may have a unique engine name. Additionally, the one or more projects 802 may each have unique project names, and each query may have a unique continuous query name and begin with a uniquely named source window of the one or more source windows 806. ESPE 800 may or may not be persistent.

Continuous query modeling involves defining directed graphs of windows for event stream manipulation and transformation. A window in the context of event stream manipulation and transformation is a processing node in an event stream processing model. A window in a continuous query can perform aggregations, computations, pattern-matching, and other operations on data flowing through the window. A continuous query may be described as a directed graph of source, relational, pattern matching, and procedural windows. The one or more source windows 806 and the one or more derived windows 808 represent continuously executing queries that generate updates to a query result set as new event blocks stream through ESPE 800. A directed graph, for example, is a set of nodes connected by edges, where the edges have a direction associated with them.

An event object may be described as a packet of data accessible as a collection of fields, with at least one of the fields defined as a key or unique identifier (ID). The event object may be created using a variety of formats including binary, alphanumeric, XML, etc. Each event object may include one or more fields designated as a primary identifier (ID) for the event so ESPE 800 can support operation codes (opcodes) for events including insert, update, upsert, and delete. Upsert opcodes update the event if the key field already exists; otherwise, the event is inserted. For illustration, an event object may be a packed binary representation of a set of field values and include both metadata and field data associated with an event. The metadata may include an opcode indicating if the event represents an insert, update, delete, or upsert, a set of flags indicating if the event is a normal, partial-update, or a retention generated event from retention policy management, and a set of microsecond timestamps that can be used for latency measurements.

An event block object may be described as a grouping or package of event objects. An event stream may be described as a flow of event block objects. A continuous query of the one or more continuous queries 804 transforms a source event stream made up of streaming event block objects published into ESPE 800 into one or more output event streams using the one or more source windows 806 and the one or more derived windows 808. A continuous query can also be thought of as data flow modeling.

The one or more source windows 806 are at the top of the directed graph and have no windows feeding into them. Event streams are published into the one or more source windows 806, and from there, the event streams may be directed to the next set of connected windows as defined by the directed graph. The one or more derived windows 808 are all instantiated windows that are not source windows and that have other windows streaming events into them. The one or more derived windows 808 may perform computations or transformations on the incoming event streams. The one or more derived windows 808 transform event streams based on the window type (that is operators such as join, filter, compute, aggregate, copy, pattern match, procedural, union, etc.) and window settings. As event streams are published into ESPE 800, they are continuously queried, and the resulting sets of derived windows in these queries are continuously updated.

FIG. 9 illustrates a flow chart showing an example process including operations performed by an event stream processing engine, according to some embodiments of the present technology. As noted, the ESPE 800 (or an associated ESP application) defines how input event streams are transformed into meaningful output event streams. More specifically, the ESP application may define how input event streams from publishers (e.g., network devices providing sensed data) are transformed into meaningful output event streams consumed by subscribers (e.g., a data analytics project being executed by a machine or set of machines).

Within the application, a user may interact with one or more user interface windows presented to the user in a display under control of the ESPE independently or through a browser application in an order selectable by the user. For example, a user may execute an ESP application, which causes presentation of a first user interface window, which may include a plurality of menus and selectors such as drop down menus, buttons, text boxes, hyperlinks, etc. associated with the ESP application as understood by a person of skill in the art. As further understood by a person of skill in the art, various operations may be performed in parallel, for example, using a plurality of threads.

At operation 900, an ESP application may define and start an ESPE, thereby instantiating an ESPE at a device, such as machine 220 and/or 240. In an operation 902, the engine container is created. For illustration, ESPE 800 may be instantiated using a function call that specifies the engine container as a manager for the model.

In an operation 904, the one or more continuous queries 804 are instantiated by ESPE 800 as a model. The one or more continuous queries 804 may be instantiated with a dedicated thread pool or pools that generate updates as new events stream through ESPE 800. For illustration, the one or more continuous queries 804 may be created to model business processing logic within ESPE 800, to predict events within ESPE 800, to model a physical system within ESPE 800, to predict the physical system state within ESPE 800, etc. For example, as noted, ESPE 800 may be used to support sensor data monitoring and management (e.g., sensing may include force, torque, load, strain, position, temperature, air pressure, fluid flow, chemical properties, resistance, electromagnetic fields, radiation, irradiance, proximity, acoustics, moisture, distance, speed, vibrations, acceleration, electrical potential, or electrical current, etc.).

ESPE 800 may analyze and process events in motion or "event streams." Instead of storing data and running queries against the stored data, ESPE 800 may store queries and stream data through them to allow continuous analysis of data as it is received. The one or more source windows 806 and the one or more derived windows 808 may be created based on the relational, pattern matching, and procedural algorithms that transform the input event streams into the output event streams to model, simulate, score, test, predict, etc. based on the continuous query model defined and application to the streamed data.

In an operation 906, a publish/subscribe (pub/sub) capability is initialized for ESPE 800. In an illustrative embodiment, a pub/sub capability is initialized for each project of the one or more projects 802. To initialize and enable pub/sub capability for ESPE 800, a port number may be provided. Pub/sub clients can use a host name of an ESP device running the ESPE and the port number to establish pub/sub connections to ESPE 800.

FIG. 10 illustrates an ESP system 1000 interfacing between publishing device 1022 and event subscribing devices 1024*a-c*, according to embodiments of the present technology. ESP system 1000 may include ESP device or subsystem 1001, event publishing device 1022, an event subscribing device A 1024*a*, an event subscribing device B 1024*b*, and an event subscribing device C 1024*c*. Input event streams are output to ESP device 1001 by publishing device 1022. In alternative embodiments, the input event streams may be created by a plurality of publishing devices. The plurality of publishing devices further may publish event streams to other ESP devices. The one or more continuous queries instantiated by ESPE 800 may analyze and process the input event streams to form output event streams output to event subscribing device A 1024*a*, event subscribing device B 1024*b*, and event subscribing device C 1024*c*. ESP system 1000 may include a greater or a fewer number of event subscribing devices of event subscribing devices.

Publish-subscribe is a message-oriented interaction paradigm based on indirect addressing. Processed data recipients specify their interest in receiving information from ESPE 800 by subscribing to specific classes of events, while information sources publish events to ESPE 800 without directly addressing the receiving parties. ESPE 800 coordinates the interactions and processes the data. In some cases, the data source receives confirmation that the published information has been received by a data recipient.

A publish/subscribe API may be described as a library that enables an event publisher, such as publishing device 1022, to publish event streams into ESPE 800 or an event subscriber, such as event subscribing device A 1024*a*, event subscribing device B 1024*b*, and event subscribing device C 1024*c*, to subscribe to event streams from ESPE 800. For illustration, one or more publish/subscribe APIs may be defined. Using the publish/subscribe API, an event publishing application may publish event streams into a running event stream processor project source window of ESPE 800, and the event subscription application may subscribe to an event stream processor project source window of ESPE 800.

The publish/subscribe API provides cross-platform connectivity and endianness compatibility between ESP application and other networked applications, such as event publishing applications instantiated at publishing device 1022, and event subscription applications instantiated at one or more of event subscribing device A 1024*a*, event subscribing device B 1024*b*, and event subscribing device C 1024*c*.

Referring back to FIG. 9, operation 906 initializes the publish/subscribe capability of ESPE 800. In an operation 908, the one or more projects 802 are started. The one or more started projects may run in the background on an ESP device. In an operation 910, an event block object is received from one or more computing device of the event publishing device 1022.

ESP subsystem 1001 may include a publishing client 1002, ESPE 800, a subscribing client A 1004, a subscribing client B 1006, and a subscribing client C 1008. Publishing client 1002 may be started by an event publishing application executing at publishing device 1022 using the publish/subscribe API. Subscribing client A 1004 may be started by an event subscription application A, executing at event subscribing device A 1024*a* using the publish/subscribe API. Subscribing client B 1006 may be started by an event subscription application B executing at event subscribing device B 1024*b* using the publish/subscribe API. Subscribing client C 1008 may be started by an event subscription application C executing at event subscribing device C 1024*c* using the publish/subscribe API.

An event block object containing one or more event objects is injected into a source window of the one or more source windows 806 from an instance of an event publishing application on event publishing device 1022. The event block object may be generated, for example, by the event publishing application and may be received by publishing client 1002. A unique ID may be maintained as the event block object is passed between the one or more source windows 806 and/or the one or more derived windows 808 of ESPE 800, and to subscribing client A 1004, subscribing client B 1006, and subscribing client C 1008 and to event subscription device A 1024*a*, event subscription device B 1024*b*, and event subscription device C 1024*c*. Publishing client 1002 may further generate and include a unique embedded transaction ID in the event block object as the event block object is processed by a continuous query, as well as the unique ID that publishing device 1022 assigned to the event block object.

In an operation 912, the event block object is processed through the one or more continuous queries 804. In an operation 914, the processed event block object is output to one or more computing devices of the event subscribing devices 1024*a-c*. For example, subscribing client A 1004, subscribing client B 1006, and subscribing client C 1008 may send the received event block object to event subscription device A 1024*a*, event subscription device B 1024*b*, and event subscription device C 1024*c*, respectively.

ESPE 800 maintains the event block containership aspect of the received event blocks from when the event block is published into a source window and works its way through the directed graph defined by the one or more continuous queries 804 with the various event translations before being output to subscribers. Subscribers can correlate a group of subscribed events back to a group of published events by comparing the unique ID of the event block object that a publisher, such as publishing device 1022, attached to the event block object with the event block ID received by the subscriber.

In an operation 916, a determination is made concerning whether or not processing is stopped. If processing is not stopped, processing continues in operation 910 to continue receiving the one or more event streams containing event block objects from the, for example, one or more network devices. If processing is stopped, processing continues in an operation 918. In operation 918, the started projects are stopped. In operation 920, the ESPE is shutdown.

As noted, in some embodiments, big data is processed for an analytics project after the data is received and stored. In other embodiments, distributed applications process continuously flowing data in real-time from distributed sources by applying queries to the data before distributing the data to geographically distributed recipients. As noted, an event stream processing engine (ESPE) may continuously apply the queries to the data as it is received and determines which entities receive the processed data. This allows for large amounts of data being received and/or collected in a variety of environments to be processed and distributed in real time. For example, as shown with respect to FIG. 2, data may be collected from network devices that may include devices within the internet of things, such as devices within a home automation network. However, such data may be collected from a variety of different resources in a variety of different environments. In any such situation, embodiments of the present technology allow for real-time processing of such data.

Aspects of the current disclosure provide technical solutions to technical problems, such as computing problems that arise when an ESP device fails which results in a complete service interruption and potentially significant data loss. The data loss can be catastrophic when the streamed data is supporting mission critical operations such as those in support of an ongoing manufacturing or drilling operation. An embodiment of an ESP system achieves a rapid and seamless failover of ESPE running at the plurality of ESP devices without service interruption or data loss, thus significantly improving the reliability of an operational system that relies on the live or real-time processing of the data streams. The event publishing systems, the event subscribing systems, and each ESPE not executing at a failed ESP device are not aware of or effected by the failed ESP device. The ESP system may include thousands of event publishing systems and event subscribing systems. The ESP system keeps the failover logic and awareness within the boundaries of out-messaging network connector and out-messaging network device.

In one example embodiment, a system is provided to support a failover when event stream processing (ESP) event blocks. The system includes, but is not limited to, an out-messaging network device and a computing device. The computing device includes, but is not limited to, a processor and a computer-readable medium operably coupled to the processor. The processor is configured to execute an ESP engine (ESPE). The computer-readable medium has instructions stored thereon that, when executed by the processor, cause the computing device to support the failover. An event block object is received from the ESPE that includes a unique identifier. A first status of the computing device as active or standby is determined. When the first status is active, a second status of the computing device as newly active or not newly active is determined. Newly active is determined when the computing device is switched from a standby status to an active status. When the second status is newly active, a last published event block object identifier that uniquely identifies a last published event block object is determined. A next event block object is selected from a non-transitory computer-readable medium accessible by the computing device. The next event block object has an event block object identifier that is greater than the determined last published event block object identifier. The selected next event block object is published to an out-messaging network device. When the second status of the computing device is not newly active, the received event block object is published to the out-messaging network device. When the first status of the computing device is standby, the received event block object is stored in the non-transitory computer-readable medium.

Figure 11:
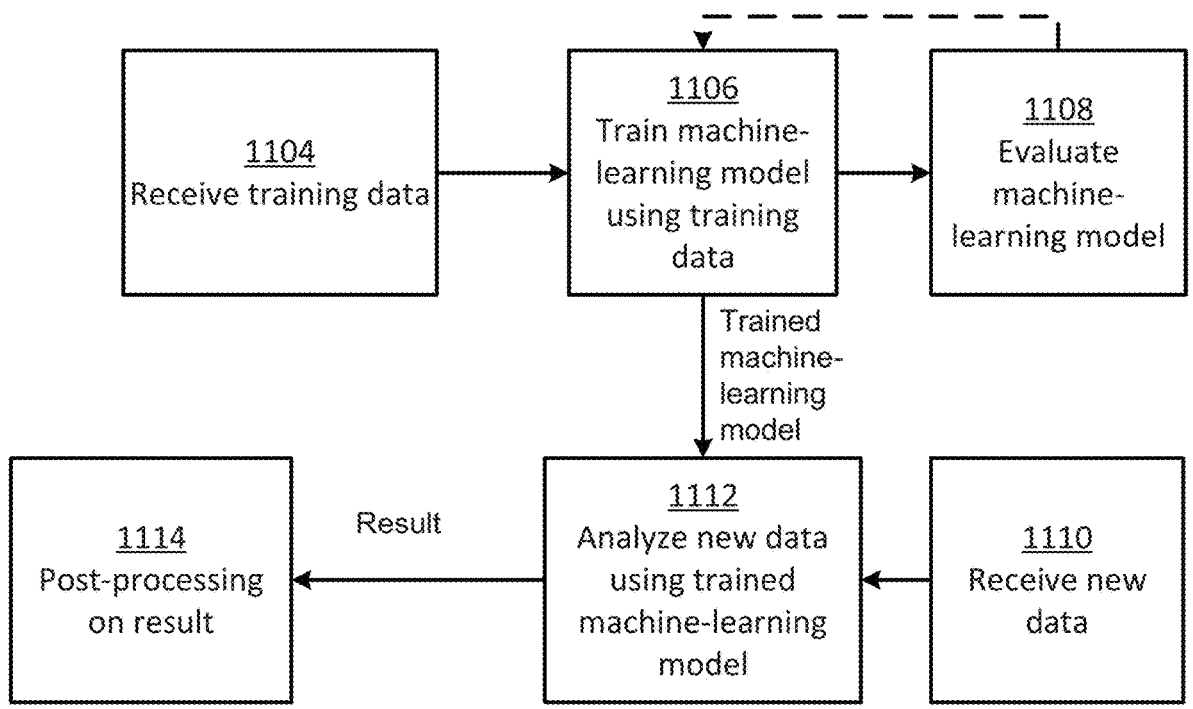
FIG. 11 illustrates a flow chart of an example of a process for generating and using a machine-learning model according to at least one embodiment of the present technology.

FIG. 11 is a flow chart of an example of a process for generating and using a machine-learning model according to some aspects. Machine learning is a branch of artificial intelligence that relates to mathematical models that can learn from, categorize, and make predictions about data. Such mathematical models, which can be referred to as machine-learning models, can classify input data among two or more classes; cluster input data among two or more groups; predict a result based on input data; identify patterns or trends in input data; identify a distribution of input data in a space; or any combination of these. Examples of machine-learning models can include (i) neural networks; (ii) decision trees, such as classification trees and regression trees; (iii) classifiers, such as Naïve bias classifiers, logistic regression classifiers, ridge regression classifiers, random forest classifiers, least absolute shrinkage and selector operator (LASSO) classifiers, and support vector machines; (iv) clusterers, such as k-means clustering, mean-shift clusterers, and spectral clusterers; (v) factorizers, such as factorization machines, principal component analyzers and kernel principal component analyzers; and (vi) ensembles or other combinations of machine-learning models. In some examples, neural networks can include deep neural networks, feed-forward neural networks, recurrent neural networks, convolutional neural networks, radial basis function (RBF) neural networks, echo state neural networks, long short-term memory neural networks, bi-directional recurrent neural networks, gated neural networks, hierarchical recurrent neural networks, stochastic neural networks, modular neural networks, spiking neural networks, dynamic neural networks, cascading neural networks, neuro-fuzzy neural networks, or any combination of these.

Different machine-learning models may be used interchangeably to perform a task. Examples of tasks that can be performed at least partially using machine-learning models include various types of scoring; bioinformatics; cheminformatics; software engineering; fraud detection; customer segmentation; generating online recommendations; adaptive websites; determining customer lifetime value; search engines; placing advertisements in real time or near real time; classifying DNA sequences; affective computing; performing natural language processing and understanding; object recognition and computer vision; robotic locomotion; playing games; optimization and metaheuristics; detecting network intrusions; medical diagnosis and monitoring; or predicting when an asset, such as a machine, will need maintenance.

Any number and combination of tools can be used to create machine-learning models. Examples of tools for creating and managing machine-learning models can include SAS® Enterprise Miner, SAS® Rapid Predictive Modeler, and SAS® Model Manager, SAS Cloud Analytic Services (CAS)®, SAS Viya® of all which are by SAS Institute Inc. of Cary, North Carolina.

Machine-learning models can be constructed through an at least partially automated (e.g., with little or no human involvement) process called training. During training, input data can be iteratively supplied to a machine-learning model to enable the machine-learning model to identify patterns related to the input data or to identify relationships between the input data and output data. With training, the machine-learning model can be transformed from an untrained state to a trained state. Input data can be split into one or more training sets and one or more validation sets, and the training process may be repeated multiple times. The splitting may follow a k-fold cross-validation rule, a leave-one-out-rule, a leave-p-out rule, or a holdout rule. An overview of training and using a machine-learning model is described below with respect to the flow chart of FIG. 11.

In block 1104, training data is received. In some examples, the training data is received from a remote database or a local database, constructed from various subsets of data, or input by a user. The training data can be used in its raw form for training a machine-learning model or pre-processed into another form, which can then be used for training the machine-learning model. For example, the raw form of the training data can be smoothed, truncated, aggregated, clustered, or otherwise manipulated into another form, which can then be used for training the machine-learning model.

In block 1106, a machine-learning model is trained using the training data. The machine-learning model can be trained in a supervised, unsupervised, or semi-supervised manner. In supervised training, each input in the training data is correlated to a desired output. This desired output may be a scalar, a vector, or a different type of data structure such as text or an image. This may enable the machine-learning model to learn a mapping between the inputs and desired outputs. In unsupervised training, the training data includes inputs, but not desired outputs, so that the machine-learning model has to find structure in the inputs on its own. In semi-supervised training, only some of the inputs in the training data are correlated to desired outputs.

In block 1108, the machine-learning model is evaluated. For example, an evaluation dataset can be obtained, for example, via user input or from a database. The evaluation dataset can include inputs correlated to desired outputs. The inputs can be provided to the machine-learning model and the outputs from the machine-learning model can be compared to the desired outputs. If the outputs from the machine-learning model closely correspond with the desired outputs, the machine-learning model may have a high degree of accuracy. For example, if 90% or more of the outputs from the machine-learning model are the same as the desired outputs in the evaluation dataset, the machine-learning model may have a high degree of accuracy. Otherwise, the machine-learning model may have a low degree of accuracy. The 90% number is an example only. A realistic and desirable accuracy percentage is dependent on the problem and the data.

In some examples, if the machine-learning model has an inadequate degree of accuracy for a particular task, the process can return to block 1106, where the machine-learning model can be further trained using additional training data or otherwise modified to improve accuracy. If the machine-learning model has an adequate degree of accuracy for the particular task, the process can continue to block 1110.

In block 1110, new data is received. In some examples, the new data is received from a remote database or a local database, constructed from various subsets of data, or input by a user. The new data may be unknown to the machine-learning model. For example, the machine-learning model may not have previously processed or analyzed the new data.

In block 1112, the trained machine-learning model is used to analyze the new data and provide a result. For example, the new data can be provided as input to the trained machine-learning model. The trained machine-learning model can analyze the new data and provide a result that includes a classification of the new data into a particular class, a clustering of the new data into a particular group, a prediction based on the new data, or any combination of these.

In block 1114, the result is post-processed. For example, the result can be added to, multiplied with, or otherwise combined with other data as part of a job. As another example, the result can be transformed from a first format, such as a time series format, into another format, such as a count series format. Any number and combination of operations can be performed on the result during post-processing.

Figure 12:
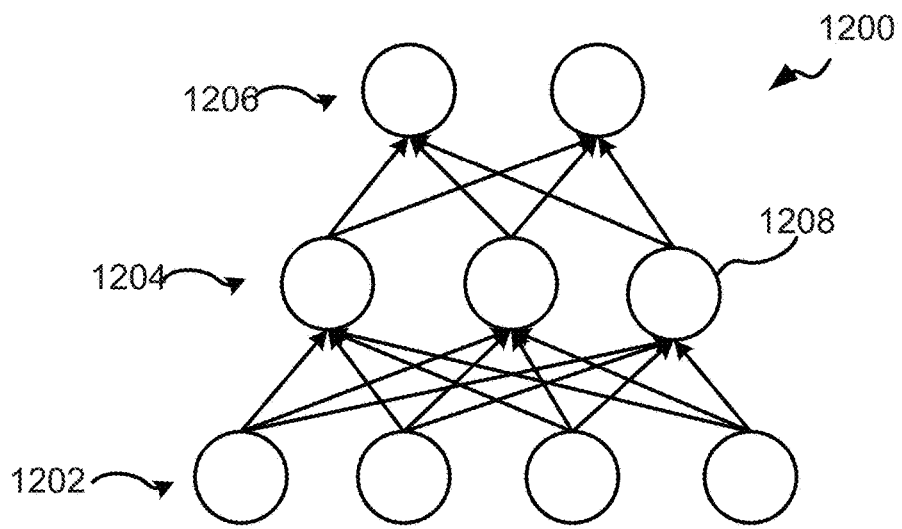
FIG. 12 illustrates an example of a machine-learning model as a neural network according to at least one embodiment of the present technology.

A more specific example of a machine-learning model is the neural network 1200 shown in FIG. 12. The neural network 1200 is represented as multiple layers of interconnected neurons, such as neuron 1208, that can exchange data between one another. The layers include an input layer 1202 for receiving input data, a hidden layer 1204, and an output layer 1206 for providing a result. The hidden layer 1204 is referred to as hidden because it may not be directly observable or have its input directly accessible during the normal functioning of the neural network 1200. Although the neural network 1200 is shown as having a specific number of layers and neurons for exemplary purposes, the neural network 1200 can have any number and combination of layers, and each layer can have any number and combination of neurons.

The neurons and connections between the neurons can have numeric weights, which can be tuned during training. For example, training data can be provided to the input layer 1202 of the neural network 1200, and the neural network 1200 can use the training data to tune one or more numeric weights of the neural network 1200. In some examples, the neural network 1200 can be trained using backpropagation. Backpropagation can include determining a gradient of a particular numeric weight based on a difference between an actual output of the neural network 1200 and a desired output of the neural network 1200. Based on the gradient, one or more numeric weights of the neural network 1200 can be updated to reduce the difference, thereby increasing the accuracy of the neural network 1200. This process can be repeated multiple times to train the neural network 1200. For example, this process can be repeated hundreds or thousands of times to train the neural network 1200.

In some examples, the neural network 1200 is a feed-forward neural network. In a feed-forward neural network, every neuron only propagates an output value to a subsequent layer of the neural network 1200. For example, data may only move one direction (forward) from one neuron to the next neuron in a feed-forward neural network.

In other examples, the neural network 1200 is a recurrent neural network. A recurrent neural network can include one or more feedback loops, allowing data to propagate in both forward and backward through the neural network 1200. This can allow for information to persist within the recurrent neural network. For example, a recurrent neural network can determine an output based at least partially on information that the recurrent neural network has seen before, giving the recurrent neural network the ability to use previous input to inform the output.

In some examples, the neural network 1200 operates by receiving a vector of numbers from one layer; transforming the vector of numbers into a new vector of numbers using a matrix of numeric weights, a nonlinearity, or both; and providing the new vector of numbers to a subsequent layer of the neural network 1200. Each subsequent layer of the neural network 1200 can repeat this process until the neural network 1200 outputs a final result at the output layer 1206. For example, the neural network 1200 can receive a vector of numbers as an input at the input layer 1202. The neural network 1200 can multiply the vector of numbers by a matrix of numeric weights to determine a weighted vector.

The matrix of numeric weights can be tuned during the training of the neural network 1200. The neural network 1200 can transform the weighted vector using a nonlinearity, such as a sigmoid tangent or the hyperbolic tangent. In some examples, the nonlinearity can include a rectified linear unit, which can be expressed using the following equation:

$$y=\max(x,0)$$

where y is the output and x is an input value from the weighted vector. The transformed output can be supplied to a subsequent layer, such as the hidden layer 1204, of the neural network 1200. The subsequent layer of the neural network 1200 can receive the transformed output, multiply the transformed output by a matrix of numeric weights and a nonlinearity, and provide the result to yet another layer of the neural network 1200. This process continues until the neural network 1200 outputs a final result at the output layer 1206.

Other examples of the present disclosure may include any number and combination of machine-learning models having any number and combination of characteristics. The machine-learning model(s) can be trained in a supervised, semi-supervised, or unsupervised manner, or any combination of these. The machine-learning model(s) can be implemented using a single computing device or multiple computing devices, such as the communications grid computing system 400 discussed above.

Implementing some examples of the present disclosure at least in part by using machine-learning models can reduce the total number of processing iterations, time, memory, electrical power, or any combination of these consumed by a computing device when analyzing data. For example, a neural network may more readily identify patterns in data than other approaches. This may enable the neural network to analyze the data using fewer processing cycles and less memory than other approaches, while obtaining a similar or greater level of accuracy.

Some machine-learning approaches may be more efficiently and speedily executed and processed with machine-learning specific processors (e.g., not a generic CPU). Such processors may also provide an energy savings when compared to generic CPUs. For example, some of these processors can include a graphical processing unit (GPU), an application-specific integrated circuit (ASIC), a field-programmable gate array (FPGA), an artificial intelligence (AI) accelerator, a neural computing core, a neural computing engine, a neural processing unit, a purpose-built chip architecture for deep learning, and/or some other machine-learning specific processor that implements a machine learning approach or one or more neural networks using semiconductor (e.g., silicon (Si), gallium arsenide (GaAs)) devices. Furthermore, these processors may also be employed in heterogeneous computing architectures with a number of and a variety of different types of cores, engines, nodes, and/or layers to achieve various energy efficiencies, processing speed improvements, data communication speed improvements, and/or data efficiency targets and improvements throughout various parts of the system when compared to a homogeneous computing architecture that employs CPUs for general purpose computing.

Clean water is helpful for maintaining healthy ecosystems and communities. Lakes, rivers, streams, and groundwater serve as wildlife habitats and recreational areas, and provide inhabitants with drinking water. However, natural and human pollutants impact the quality of water and threaten livelihoods around the globe. Pinpointing how stressors such as environmental pollutants impact water networks is a complex task, especially on a macro scale. One or more embodiments seek to address this complexity and match specific environmental stressors to downstream monitoring stations on a flow network, as well as to match stressors and monitoring stations to the negative effects of poor water quality (e.g., blue-green algae events) that may occur downstream. This approach improves upon processes that link environmental stressors to water quality monitoring stations that are near the stressors in terms of distance, but that may be uphill or upstream from a stressor and therefore not likely to be impacted.

Figure 13A:
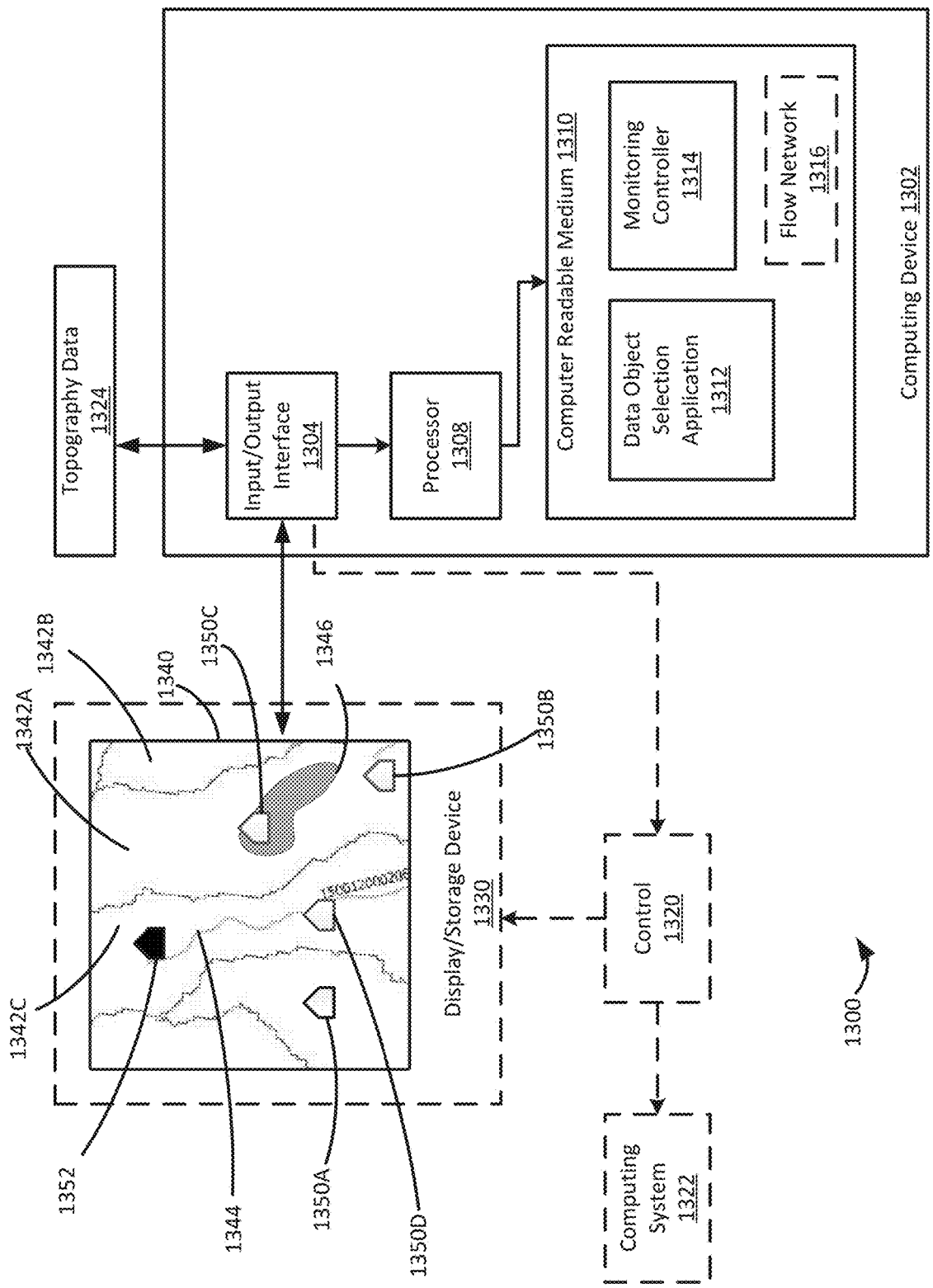
FIG. 13A illustrates a block diagram of a system for selecting related data objects according to at least one embodiment of the present technology.

FIG. 13A illustrates a block diagram of a system 1300 for selecting data objects (e.g., ones associated with monitoring stations or stressors). System 1300 includes a computing device 1302. The computing device 1302 comprises one or more input and/or output interfaces 1304 for obtaining information. The system 1300 is configured to exchange information between devices in the system (e.g., via wired and/or wireless transmission). For example, a network (not shown) can connect one or more devices of system 1300 to one or more other devices of system 1300. For instance, the computing device 1302 can obtain topography data 1324 indicating a topography 1340. For instance, the topography data 1332 can be downloaded from a remote computing system (not shown) comprising survey data (e.g., United States Geological Survey data). Topography data 1332 can be used to derive topography 1340. The topography 1340 has an area comprising land (shown in white) and water (shown in blue). Different areas of land are separated in this example by red lines to form different catchments 1342A, 1342B, and 1342C (collectively herein, "catchments 1342"). Blue lines in this topography indicate flowlines (e.g., flowline 1344). The topography 1340 can be displayed and/or stored on (e.g., on display and/or storage device 1330). For instance, additional monitoring stations 1350A, 1350B, 1350C, 1350D (collectively herein, "monitoring stations 1350") (e.g., water quality monitoring stations) can be stored in association with the topography 1340 (e.g., as data objects with location variables associated indicating a location in the topography 1340).

The computing system can use the one or more input and/or output interfaces 1304 to receive an indication of an identified data object 1352 for matching to other data objects in the topography. For instance, a user could identify (e.g., in a graphical user interface) a data object 1352 representing a stressor to the water ecosystem in the area. A stressor may physically exist on land, in water, or both. Regardless of its physical location, however, a stressor negatively impacts the quality of the water in a given topography. Therefore, in the context of this disclosure, stressors that may (or do) negatively impact the quality of the water are defined as "operating on water." For example, a stressor may be a land-based stressor such as a dairy farm or a septic tank, and/or a water-based stressor such as a tidal event. As another example, a stressor could also be a weather event). Additionally, stressors may be man-made or occur naturally in the environment. Alternatively, the identified data object 1352 is a monitoring station configurable to monitor a stressor. For instance, the identified data object 1352 could be identified when it was configured (e.g., to include it in a flow network of monitoring stations). One or more embodiments take flow direction, elevation, and topography into consideration when making matches of data objects to aspects of the topography. In some embodiments, this approach ensures that water quality being measured by a monitoring station is likely to be impacted by a matched environmental stressor.

The computing device 1302 has a computer-readable medium 1310 and a processor 1308. Computer-readable medium 1310 is an electronic holding place or storage for information so the information can be accessed by processor 1308. Computer-readable medium 1310 can include, but is not limited to, any type of random-access memory (RAM), any type of read only memory (ROM), any type of flash memory, etc. such as magnetic storage devices (e.g., hard disk, floppy disk, magnetic strips), optical disks (e.g., compact disc (CD), digital versatile disc (DVD)), smart cards, flash memory devices, etc.

Processor 1308 executes instructions (e.g., stored at the computer-readable medium 1310). The instructions can be carried out by a special purpose computer, logic circuits, or hardware circuits. In one or more embodiments, processor 1308 is implemented in hardware and/or firmware. Processor 1308 executes an instruction, meaning it performs or controls the operations called for by that instruction. The term "execution" is the process of running an application or the carrying out of the operation called for by an instruction. The instructions can be written using one or more programming language, scripting language, assembly language, etc. Processor 1308 in one or more embodiments can retrieve a set of instructions from a permanent memory device and copy the instructions in an executable form to a temporary memory device that is generally some form of RAM, for example. Processor 1308 operably couples with components of computing device 1302 (e.g., one or more input and/or output interfaces 1304 and with computer-readable medium 1310) to receive, to send, and to process information. According, a computing device described herein could also be considered a computing system.

In one or more embodiments, computer-readable medium 1310 stores instructions for execution by processor 1308. In one or more embodiments, one or more applications stored on computer-readable medium 1310 are implemented in software (e.g., computer-readable and/or computer-executable instructions) stored in computer-readable medium 1310 and accessible by processor 1308 for execution of the instructions. The one or more applications can be integrated with other analytic tools. For example, in one or more embodiments, the computer-readable medium 1310 comprises instructions for a data object selection application 1312. For instance, the application can be used by the computing system to determine a physical location for the identified data object 1352 in the topography 1340. In this example, the identified data object 1352 is located in a catchment 1342C. The data object selection application 1312 selects (e.g., from multiple data objects) one or more data objects to be related to the identified data object 1352 (e.g., monitoring stations 1350 that are downstream for monitoring a stressor). For instance, the data object selection application 1312 determines a classification for the identified data object 1352 indicating whether the identified data object 1352 operates "in" water.

In the context of the present embodiments, an object is classified as operating "in" water when the object is, at least partially, physically located in the water. For instance, consider a situation where a water-based stressor (e.g., an algae bloom) is a candidate to stress (i.e., negatively impact) the water of a water ecosystem in the area. Because the stressor is physically located in the water, the identified data object 1352 representing the stressor is classified by the data object selection application 1312 as "operating in water." In another example, consider a monitoring station configured to monitor a given stressor by monitoring the water in the water ecosystem. If the monitoring station is physically located in the water, the data object selection application 1312 would classify a data object representing the monitoring station, such as identified data object 1352, as "operating in water". The computing system can select, based on the location and the classification of the identified data object 1352, the one or more related data objects determined to be related to the identified data object 1352.

In one or more embodiments, the computer-readable medium 1310 comprises a monitoring controller 1314. For instance, based on the one or more related data objects selected, the monitoring controller 1314 can generate one or more controls for monitoring the area. For example, the one or more related data objects may comprise a monitoring station configurable to monitor the stressor associated with identified data object 1352, and the monitoring controller 1314 controls a monitoring station 1350 to monitor or report on a particular pollutant associated with that stressor. As another example, the one or more related data objects comprise one or more of an effect of the stressor to the area, and the monitoring controller 1314 controls to monitor or report on a particular effect (e.g., a downstream reported effect or a measurement of a monitoring station). As another example, the one or more related data objects may represent a cause of the stressor to the area because the stressor itself may be the result of a previous cause. For instance, consider an example where the identified data object 1352 represents a fish kill event caused by some other previously reported upstream event (e.g., an algae bloom event). In such examples, the monitoring controller 1314 could generate, based on the one or more related data objects representing the previously reported upstream event (e.g., the algae bloom event), one or more controls for monitoring or reporting on the particular previously reported cause of the fish kill event.

In one or more embodiments, the computing device 1302 can issue one or more controls 1320. As an example, consider an identified data object 1352 that represents a stressor to the area because the stressor is a candidate for causing pollution in or near the area. In this example, the computing device 1302 (e.g., using monitoring controller 1314) generates the one or more controls 1320 responsive to detecting the pollution from the identified data object 1352. For instance, responsive to detecting the pollution, the computing device 1302 can generate the one or more controls 1320 that, when actuated, cause the monitoring of a second monitoring station (e.g., monitoring station 1350D by computing system 1322). Additionally, or alternatively, the computing device 1302 can generate the one or more controls 1320 that, when actuated, monitor for the spread of the pollution at the second monitoring station (e.g., monitoring station 1350D along the flowline 1344 in the catchment 1342C).

Generating the one or more controls 1320 could comprise generating a flow network 1316 based on selecting the one or more related data objects. A flow network can define a relationship between multiple data objects in the area (e.g., upstream and downstream relationships). The one or more controls 1320 can indicate to the display and/or storage device 1330 to display in a graphical user interface one or more aspects of the flow network (e.g., a graphical user interface shown in FIGS. 22A, 22B, 23, and 24). The one or more aspects comprise one or more relationships between data objects in the flow network, measurements of data objects in the flow network (e.g., measurements of a pollutants), and predictions for data objects in the flow network (e.g., predicted effects of a stressor and its location or monitoring stations predicted to provide measurements of the impact of a stressor).

One or more applications stored on computer-readable medium 1310 can be implemented as a Web application. For example, an application can be configured to receive hypertext transport protocol (HTTP) responses and to send HTTP requests. The HTTP responses may include web pages such as hypertext markup language (HTML) documents and linked objects generated in response to the HTTP requests. Each web page may be identified by a uniform resource locator (URL) that includes the location or address of the computing device that contains the resource to be accessed in addition to the location of the resource on that computing device. The type of file or resource depends on the Internet application protocol such as the file transfer protocol, HTTP, H.323, etc. The file accessed may be a simple text file, an image file, an audio file, a video file, an executable, a common gateway interface application, a Java applet, an extensible markup language (XML) file, or any other type of file supported by HTTP.

In one or more embodiments, fewer, different, and additional components can be incorporated into computing device 1302. For instance, in one or more embodiments, there are multiple input devices or computing systems. In the same or different embodiments, there are multiple output devices or computing systems. As another example, the one or more input and/or output interfaces 1304 has more than one input interface that uses the same or different interface technology. Alternatively, or additionally, the output interface 1306 has more than one output interface that uses the same or different interface technology.

Figure 13B:
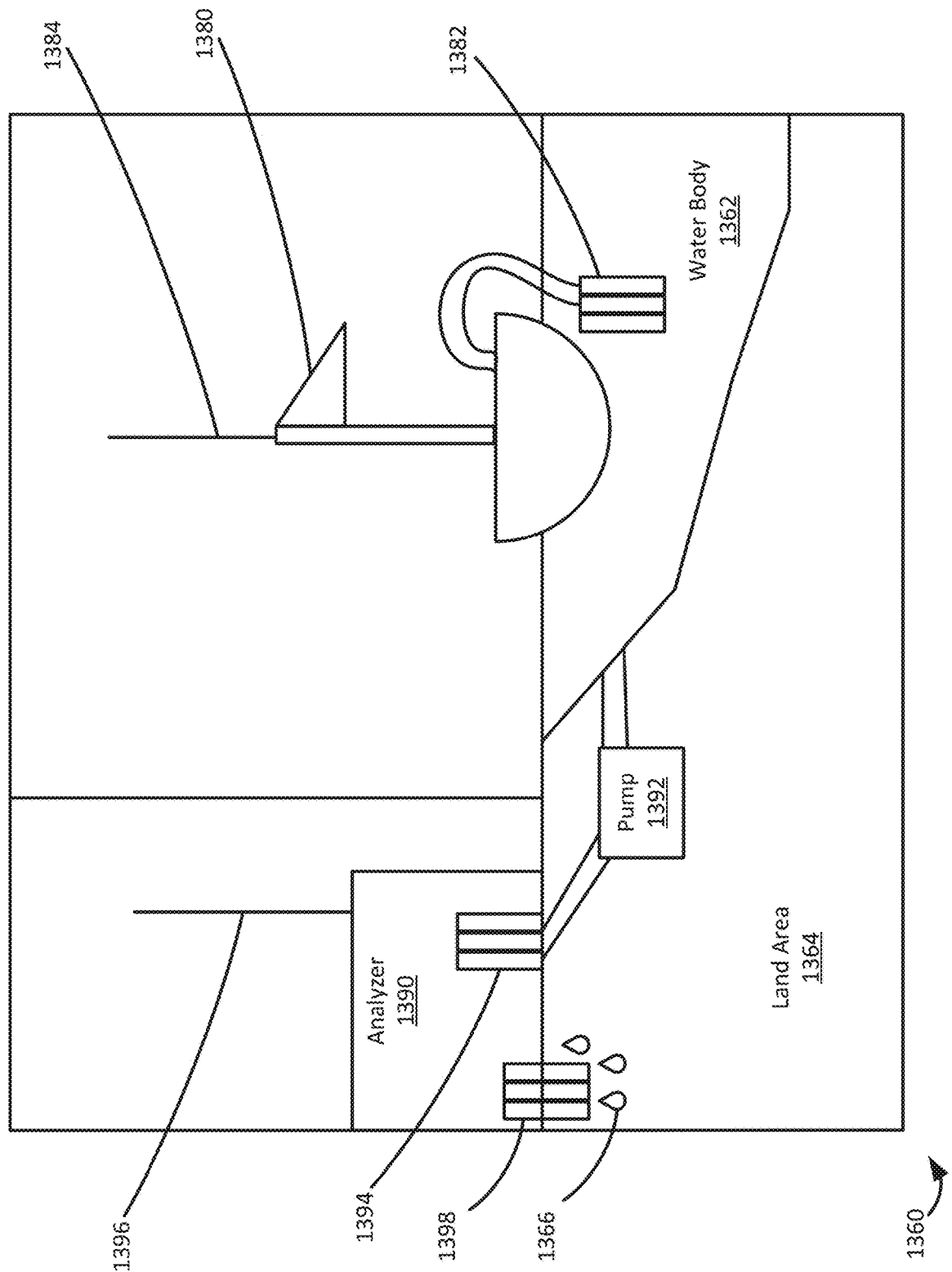
FIG. 13B illustrates example monitoring stations according to at least one embodiment of the present technology.

FIG. 13B illustrates example monitoring stations in a cross-section 1360 of an area comprising land area 1364 and water body 1362. In this example, there is a monitoring station that acts as an analyzer 1390 and monitoring station acting as a collector 1380. The monitoring stations in this example are configured to operate in water (i.e., they are physically located in a body of water), and therefore, are considered by the present embodiments as "operating in water". For instance, the collector 1380 is configurable to monitor a stressor (e.g., a stressor to water body 1362) by monitoring water in the water body 1362. In this example, the monitoring station (i.e., collecting station 1380) floats on the surface of the water body 1362 that it monitors so that the collector 1380 can collect the samples that are subsequently picked up for measurement or analysis. Alternatively, in one embodiment, the collector 1380 can have one or more sondes 1382, which is an instrument with sensors that takes environmental measurements. The sensors can measure information pertaining to water such as the temperature, dissolved oxygen, conductivity, ph, turbidity, and presence of substances such as chlorophyll and phycocyanin. The measurements can be reported (e.g., transmitted in real-time or in scheduled batches by antenna 1384). The collector 1380 in this case can float along the water or alternatively, can be moored in the water or supported by a platform in the water (not shown). In some cases, the collector 1380 is also an analyzer and is configured to transmit the results of an analysis instead of, or in addition to, the measurements it collects (e.g., the sonde 1382 detects a stressor event such as evidence of nutrients like phosphorus indicating an algae bloom stressor for the water body 1362). The sonde 1382 can have other components not specifically shown for collecting, measuring, or analyzing water samples such as filters, collection areas, components to generate a charge, transmitter circuitry, etc.

Analyzer 1390 is another example of a monitoring station that operates in water. In this example, the analyzer 1390 physically sits on land area 1364 and has multiple sondes (sonde 1394 and sonde 1398). However, sonde 1394 can collect water pumped from the water body 1362 (e.g., using pump 1392 that is, at least partially, located in the water). In this case, piping, for example, is located in the water to pump water samples to sonde 1394. Therefore, analyzer 1390 is considered according to the present embodiments to operate "in" water.

Additionally, or alternatively, the sonde 1398 collects water 1366 within the land area 1364 (e.g., rainwater flowing down into the land area 1364). Because sonde 1398 sits at least partially in the water, analyzer 1390 is considered to operate in water. Regardless of whether a sonde is or is not in a body of water, though, analyzer 1390 can analyze water samples collected and/or measured by sondes, and based on that analysis, detect a stressor event. For instance, a stressor event may be an event in which pesticides or automotive fluids, for example, have seeped, or are seeping, into the water 1366. The analyzer 1390 can use the antenna 1396 to transmit collections, measurements, analysis, or classifications performed by the analyzer 1390. In some embodiments, the analyzer 1390 itself performs operations described with respect to FIG. 13A (e.g., determining flow networks, classifying itself as one operating in water, and determining that a data object pertaining to a monitoring station is an identified or related data object). One of ordinary skill in the art will appreciate the analyzer 1390 could also simply be a device for collecting and measuring and the antenna 1396 could be used to transmit measurements to another device for analysis.

Figure 14:
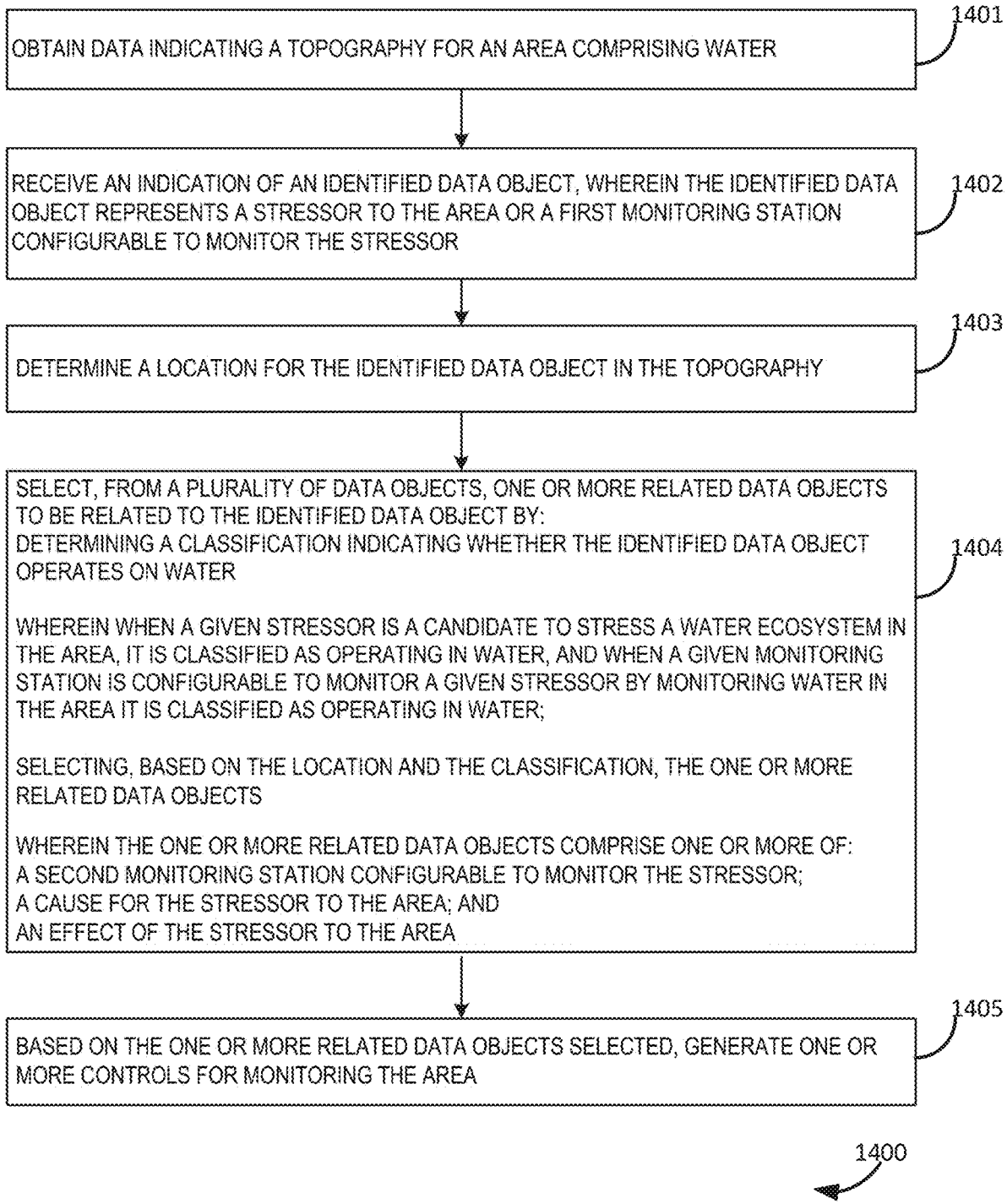
FIG. 14 illustrates a flow diagram for selecting related data objects according to at least one embodiment of the present technology.

In one or more embodiments, the system 1300 in FIG. 13A or devices in FIG. 13A or 13B (e.g., computing device 1302) implements a method as described herein (e.g., a method shown in FIGS. 14, 15A, 15B and 25). FIG. 14 illustrates a flow diagram of a method 1400 for selecting related data objects. The method 1400 comprises an operation 1401 of obtaining data indicating a topography for an area comprising water (e.g., a river, a lake, an estuary). In some embodiments, data indicating a topography for an area comprising land is also obtained.

The method 1400 comprises an operation 1402 of receiving an indication of an identified data object. The identified data object represents a stressor to the area or a first monitoring station configurable to monitor the stressor (e.g., a monitoring station shown in FIG. 13B). The method 1400 comprises an operation 1403 of determining a location for the identified data object in the topography (e.g., an x-y coordinate in topography 1340).

The method 1400 comprises an operation 1404 of selecting, from a plurality of data objects, one or more related data objects to be related to the identified data object by determining a classification indicating whether the identified data object operates in water and selecting, based on the location and the classification, the one or more related data objects. When a given land-based or water-based stressor is a candidate to stress a water ecosystem in the area, and the given stressor is at least partially physically located in the water, the given stressor is classified as operating in water. For example, water-based stressors could include one or more of blue-green algae, fish kill, red tide, population, tidal, water reuse, weather, and sanitary sewer overflows. However, when a land-based stressor is not physically located in a water body, but negatively impacts the quality of the water, is it classified as operating on water. Examples of land-based stressors could include wastewater and sewage treatment facilities, disposal facilities, and land use and land coverage (LULC) areas. Examples of LULC objects could include dairy farms, golf courses, residential areas, and industrial phosphates areas, among others.

Additionally, when a given monitoring station located at least partially in the water is configurable to monitor a given stressor by monitoring the water in the area, the given monitoring station is classified as operating in water. For instance, water quality monitoring stations (e.g., analyzer 1390) can follow the same flowline matching process as water-based stressors because the collected water samples that are analyzed also exist and operate in water. In some embodiments, it is possible that a stressor exists in water and on land. In this case, the stressor event can be duplicated with its different attributes or can be assigned to water or land. The one or more related data objects comprise one or more of: a second monitoring station configurable to monitor the stressor, a cause for the stressor to the area, and an effect of the stressor to the area.

The method 1400 comprises an operation 1405 of, based on the one or more related data objects selected, generating one or more controls for monitoring the area. For instance, controls can be generated based on a determined flow network from related data objects.

Figure 15A:
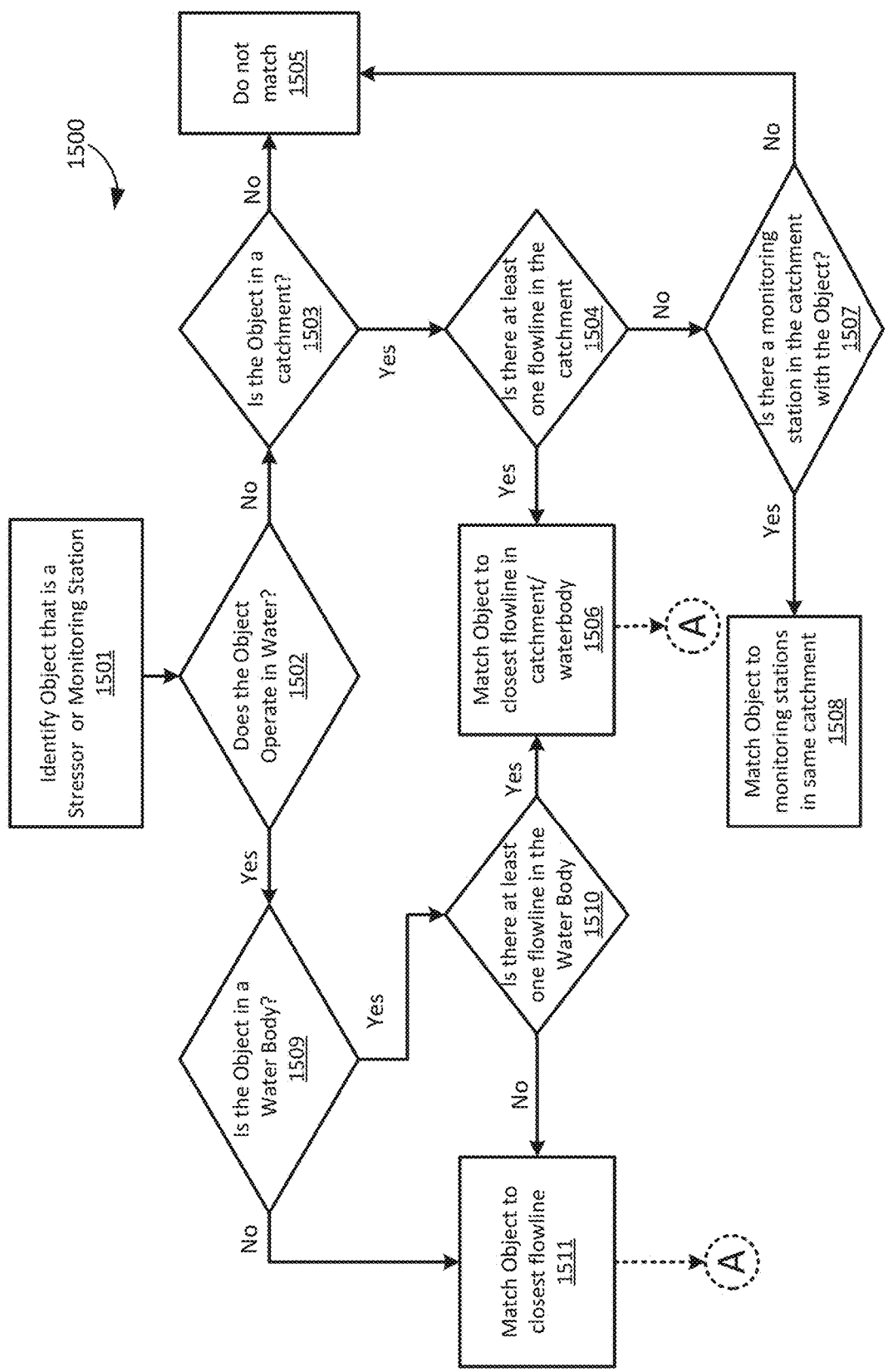
FIGS. 15A-15B illustrate a flow diagram for developing a flow network according to at least one embodiment of the present technology.
Figure 15B:
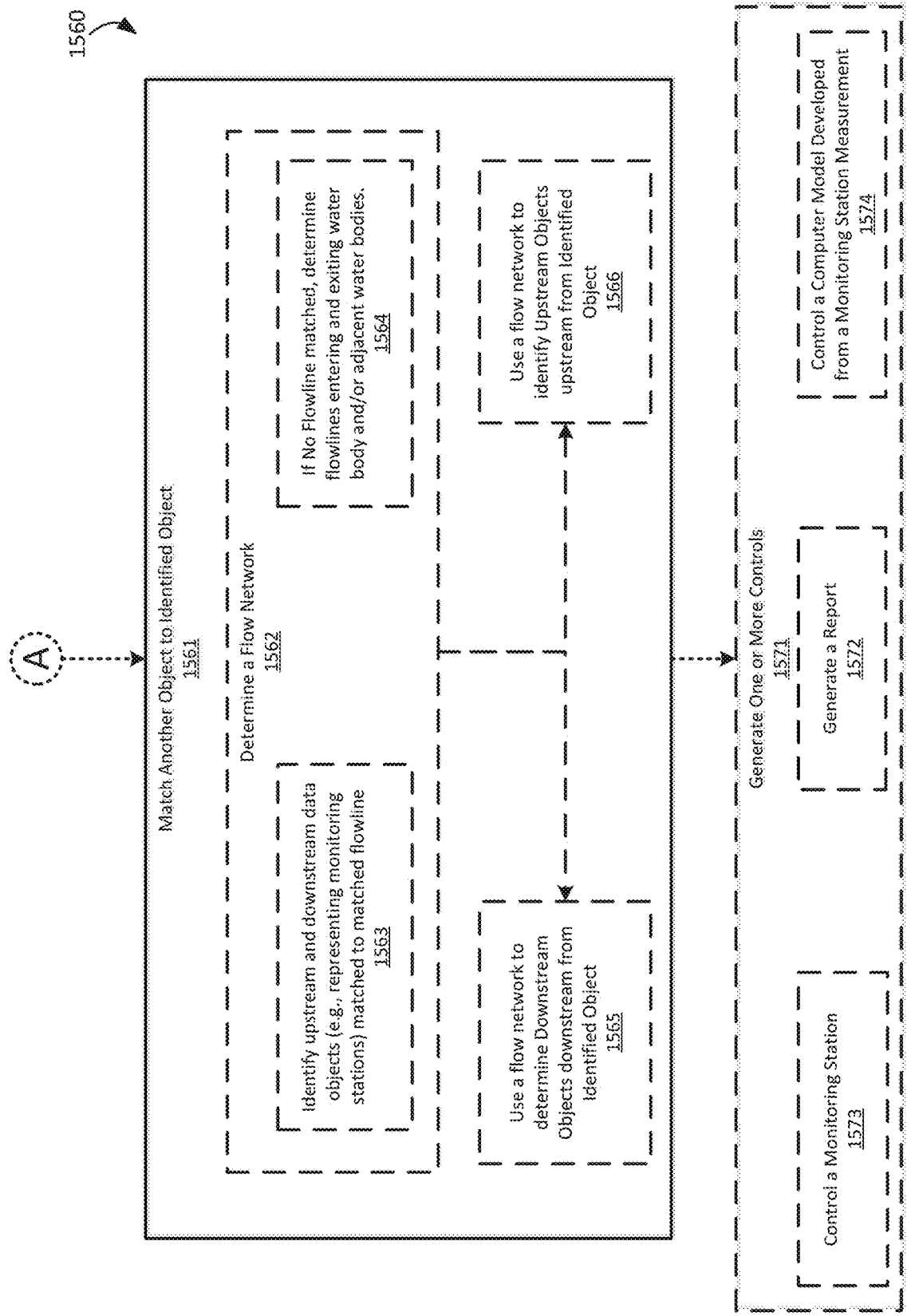

FIGS. 15A-15B illustrate a flow diagram for developing a flow network. FIG. 15A shows a portion 1500 of a flow diagram. An operation 1501 comprises identifying an object that is a stressor or monitoring station). In one or more embodiments it is determined in an operation 1502 whether the identified data object operates in water (i.e., whether the identified data object physically exists, at least partially, in the water). This can be implicitly determined (e.g., assuming all water quality monitoring stations operate in water or stressors of a certain type always operate in water or land). Alternatively, in some examples, a topography may only comprise water (e.g., in a system of lakes) or only contain land, in which case only one side of the flow diagram would be operational for a particular case.

In situations in which the topography includes land and the object does not operate in water, in an operation 1503, the computing system can determine whether the object is in a catchment. For instance, a topography can define bounds for one or more catchments. Each catchment indicates land capable of collecting or draining water based on its elevation. For instance, in some embodiments a catchment can be a land surface area that flows or drains directly into a destination such as a sink or flowline. A sink is a location classified as having no lateral flow direction. It is possible that a land-based stressor is not presently located in any catchment (e.g., a wastewater treatment plant sitting on a small island off the coast of Florida). In this case, in an operation 1505, the land-based stressor is not matched to a flowline or other data objects such as monitoring stations.

The computing system can determine that the object is in a catchment based on the topography. If the object is in a catchment, in an operation 1504, the computing system determines if there is at least one flowline in the catchment. For instance, the topography can define one or more flowlines indicating a direction of water flow over the area. In an operation 1506, if the computing system determines (e.g., based on the topography) that the identified data object is in a first catchment of one or more catchments, the computing system can associate the identified data object with a closest flowline (e.g., based on distance) in the first catchment. If the computing system determines (e.g., based on the topography), in an operation 1507 that there is not a flowline in the first catchment, the computing system determines if there are monitoring stations in the catchment with the object. If there are monitoring stations in the first catchment, in an operation 1508, the computing system can match objects to the monitoring station in the same catchment. Accordingly, if there are one or more related data objects assigned as in the first catchment (e.g., locations associated with data objects are tagged with an identifier for the first catchment), the computing system can select one or more related data objects by associating the identified data object with the one or more related data objects. If there are no monitoring stations in the catchment, in an operation 1505 the computing system can determine there is no match for the identified data object. The portion 1500 of the flow diagram references monitoring station in operations 1507 and 1508 merely for example. In other embodiments, the causes and/or the effects (i.e., impacts) of a stressor may be linked instead using this methodology.

Additionally, or alternatively, in one or more embodiments, in situations in which the topography includes water and the object operates in water (box 1502), in an operation 1509, the computing system determines if the object is in a water body. For instance, a topography can define bounds for one or more water bodies. Each water body can indicate accumulated water in the area. The water body may represent a physical environment that is actually partially empty of accumulated water or currently empty of accumulated water, but the topography may still indicate the water body based on historical data or recordation and the computing system may still determine that the object is in a water body. The topography can have other elements, or be modified to have other elements, besides catchments (e.g., buffers can be added so that objects near the edge of a water body are still classified as in the water body). In an operation 1510, if the computing system determines (e.g., based on the topography) the identified data object is in a first water body of one or more water bodies, or in a buffer associated with the first water body, the computing system can determine if there is at least one flowline in the water body. In one or more embodiments, the topography defines one or more flowlines indicating a direction of water flow over the area. In operation 1506, when there is at least one flowline, of the one or more flowlines, in the first water body, the identified data object is matched to the closest flowline (e.g., by associating the identified data object with a closest flowline that is intersecting the first water body). In an operation 1511, when there is not a flowline in the first water body, the identified data object is matched to a closest flowline outside of the water body (e.g., associate the identified data object with a closest flowline).

In one or more embodiments, the computing system can be configured to include and/or exclude certain types of flowlines for flowline matching. For example, in at least one embodiment, the computing system may be configured to select a networked flowline that is closest to an object in a catchment (i.e., in terms of distance) rather than a closer, non-networked flowline (i.e., a flowline that is isolated or that has no flow) in the catchment. This is beneficial when matching objects in a catchment to a flowline as catchment boundaries are typically generated based on how the water in a land area drains into networked flowlines (or into sinks when no networked flowlines exist in an area).

In one or more embodiments (e.g., ones in which an identified data object is matched to a flowline) additional operations can be performed to select one or more related data objects from a plurality of data objects for associating with the identified data object.

For example, in a FIG. 15B, a portion 1560 of a flow diagram is shown (e.g., it can be extensions of the flow diagram shown in FIG. 15A). The portion 1560 of the flow diagram shows an operation 1561 for matching one or more other objects to an identified object. For example, the operations 1561 could have multiple phases, such as a first phase of matching stressors and monitoring stations to a flowline, and a second phase of matching a stressor to monitoring stations along a pathway of the flow network (e.g., based on the directions to and from of flow connections and considering flowline divergence).

For example, in an optional operation 1562, a flow network is determined for matching data objects. In some examples a flow network may have been predetermined (i.e., it is not necessary to have water quality data indicating a problem to determine a flow network). For instance, in an optional operation 1563, upstream and downstream monitoring stations are matched to a flowline. In other situations, data objects can be matched to upstream or downstream data objects dynamically. For instance, a computing system may receive an indication to select upstream data objects (e.g., in response to a detected stressor or effect of stressor). This can be useful in situations in which the identified data object is a stressor or monitoring station, and a user is interested in finding causes of the stressor or measurements at a monitoring station that may be upstream.

For instance, in one example, a computing system receives an indication to select upstream data objects for associating with an identified object. The computing system can generate one or more controls for monitoring an area in response. For instance, the computing system can generate a flow network based on selecting the one or more related data objects that are a predicted cause for the stressor to the area or a measurement at a monitoring station (e.g., stressor or monitoring station represented by the identified data object) and are upstream of the identified data object. The flow network can define an estimated direction of flow of fluid between multiple data objects in the area. In some cases, the generated flow network can define an estimated direction of flow of a computer predicted effect of the stressor between multiple data objects in the area (e.g., an effect caused by a pollutant transported by water flowing along flowlines). In an optional operation 1566, the computing system can use a flow network to identify upstream objects upstream of the identified object.

Additionally, or alternatively, a computing system receives an indication to select downstream data objects. The computing system can generate one or more controls for monitoring an area in response. For instance, the computing system can generate a flow network based on selecting the one or more related data objects that are downstream of the identified data object. The one or more related data can include a second monitoring station and/or a predicted effect for the stressor to the area. In an optional operation 1565, the computing system can use a flow network to identify downstream objects downstream of the identified object.

In an optional operation 1571, a computing system can generate one or more additional controls (e.g., match a stressor to monitoring stations along a flow network). For instance, a control 1573 can be related to controlling a monitoring station. For example, the control 1573 can indicate to increase or begin measuring for certain pollutants at monitoring stations downstream of a stressor. As another example, the control 1573 can indicate to send certain measurements or analysis to help with determining a stressor upstream of the monitoring station or stressor effect downstream of the monitoring station.

In one or more embodiments, the optional operation 1571 comprises generating a control 1572 for generating a report (e.g., for monitoring the flow network or related data objects). For instance, stressors are treated in the report as the cause of poor water quality and are linked to downstream water quality monitoring stations to examine the impact of these stressors. As another example, an effect can also itself be a stressor (e.g., growth of blue green algae because of poor water quality) and the report can show a link of water quality monitoring stations to downstream blue green algae events (reverse association). The results will allow the user of the report to view upstream stressors and water quality conditions that lead to the effects of stressor events (referred to herein as "effect stressor events") so that the user may be able to predict when they will occur in the future (e.g., using computer modeling or analytics).

Figure 15C:
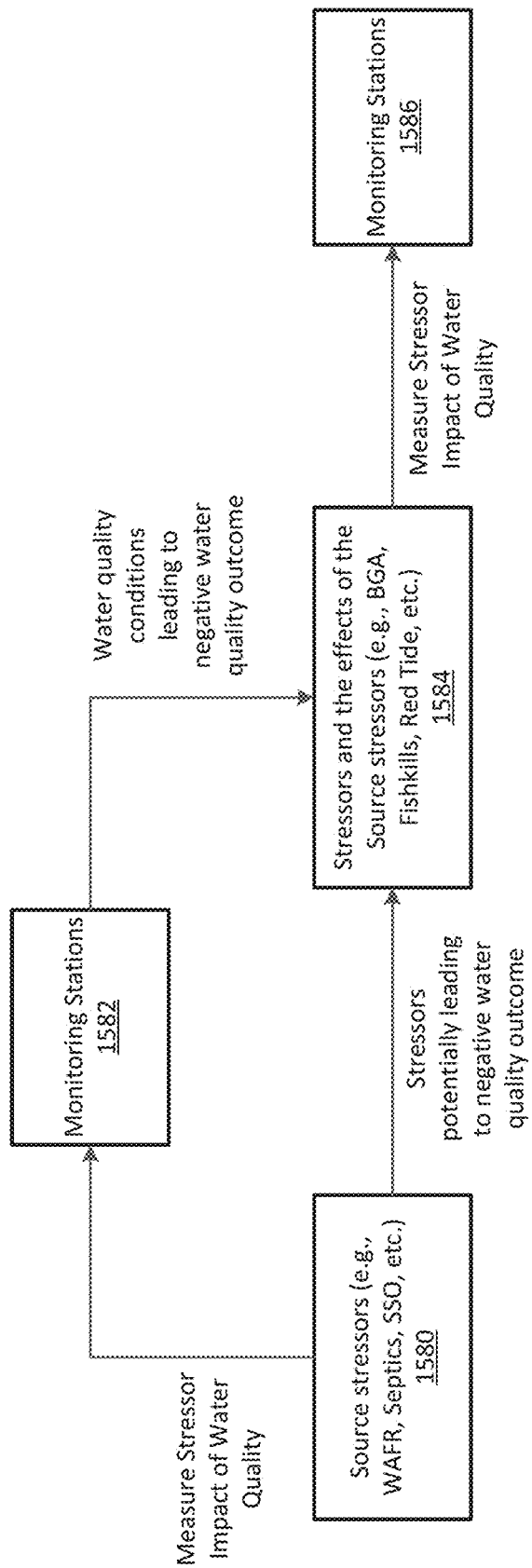
FIG. 15C illustrates a difference between a stressor event and an effect stressor event according to at least one embodiment of the present technology.

FIG. 15C illustrates a difference between a stressor event and an effect stressor event according to at least one embodiment of the present technology. As seen in FIG. 15C, source stressors 1580 comprise stressor events that may potentially negatively impact water. These stressor events are monitored by one or more downstream monitoring stations 1582 that measure the impact of the stressor on downstream water quality. The stressors events 1580, and the water quality conditions measured by the one or more monitoring stations 1582 can lead to downstream effect stressor events 1584. The impact of the stressor events 1584, in this embodiment, may also be monitored by one or more downstream monitoring stations 1586.

Returning to FIG. 15B, the optional operation 1571 also comprises, additionally or alternatively, generating a control 1574 for controlling a computer model developed from a monitoring station measurement (e.g., a computer model predicting degradation of an area in response to a measured pollutant).

Figure 16:
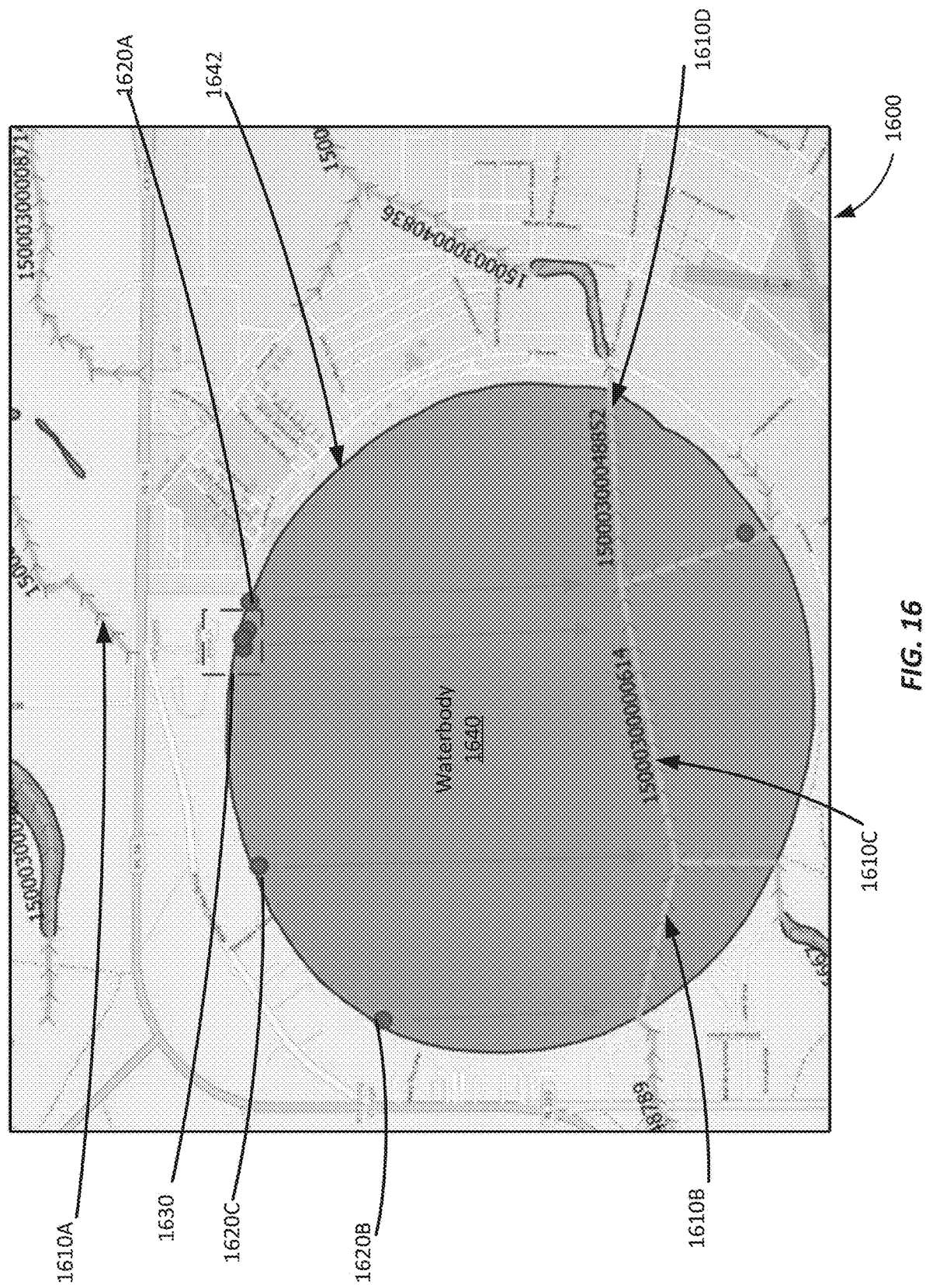
FIG. 16 illustrates an example mapping to a flowline in a water body in at least one embodiment of the present technology.

FIG. 16 illustrates an example mapping to a flowline in a water body. A map 1600 represents a topography defining flowlines 1610 indicating a direction of water flow over the area (e.g., flowlines are shown with arrows indicating a direction for the flowline). Flowlines can meet each other at intersection points. For instance, flowline 1610B meets flowline 1610C at one end and flowline 1610D meets flowline 1610C at the other end. A topography can also define bounds for one or more bounded areas (e.g., water bodies or catchments). FIG. 16 shows a water body 1640, with a bound 1642. The blue area inside the bound 1642 indicates an area of accumulated water in the area. Water bodies in the physical terrain may be only partially filled or empty, or have other fluids within the water bodies, but the topography may represent a water body expected, or recorded in the past to have, accumulated water. In this example, the computing system selects one or more related data objects for each of the stressors 1620 (e.g., reported fish kill events) and cluster 1630 of stressors. Stressors are represented in the map with a purple dot. In this example, the computing system associates, based on the location, the identified data object with a flowline in a bounded area of the multiple bounded areas. For instance, in this case, stressor 1620B is associated with flowline 1610B, stressor 1620C is associated with flowline 1610C, stressor 1620A is associated with flowline 1610D, and cluster 1630 is associated with flowline 1610C. As shown in FIG. 16, this approach may mean that a stressor is not associated with a flowline geographically closest. For instance, flowline 1610A is much closer geographically to cluster 1630 and stressor 1620A than the selected flowline which intersects with the water body 1640. However, matching to a flowline in the same water body may provide advantages for associating appropriate effects or monitoring stations downstream of the stressors as determined by the flowlines.

Figure 17:
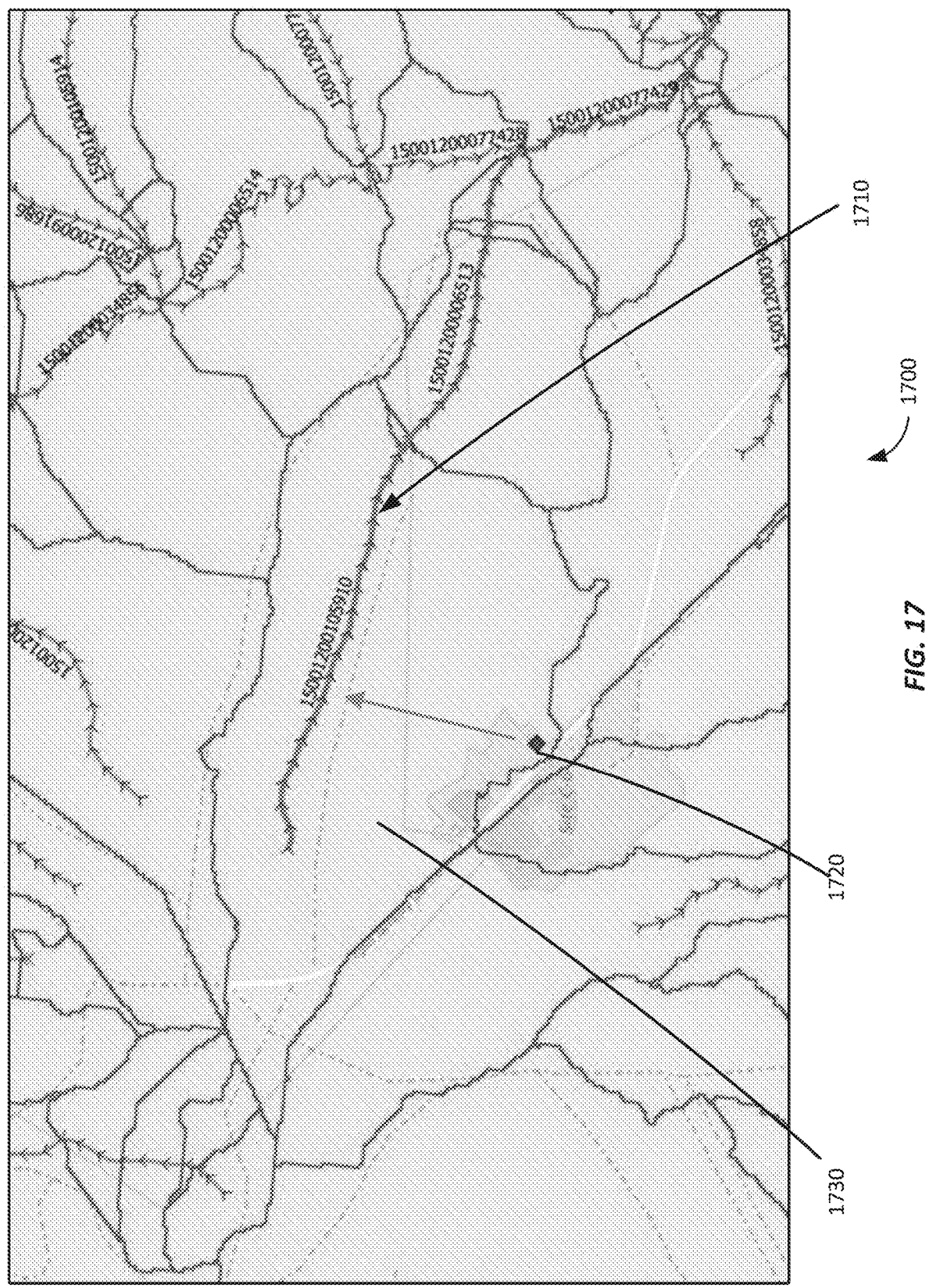
FIG. 17 illustrates an example mapping to a flowline in a catchment in at least one embodiment of the present technology.

FIG. 17 shows an example, in which the graphical representation 1700 of the topography has bounds for one or more catchments, each catchment indicating an area capable of collecting or draining water based on its elevation. The redlines are used to define the edges of different catchments. For instance, flowline 1710 is in a catchment 1730. Flowlines on land can indicate direction of surface water flow (e.g., expected direction of rainfall).

In this example, the stressor 1720 is an identified data object operating or occurring on land (e.g., a land-based stressor). The computing system can select one or more related data objects by associating, based on the location, the stressor 1720 with a flowline 1710 in a catchment 1730 which is a bounded area meeting the edges of multiple other catchments (bounded areas) in the topography. The computing system can select one or more related data objects associated with the flowline in the bounded area.

In other examples, potentiometric maps could be used as a reference data set for the direction of underground water flow as an additional consideration in some examples. For simplicity this example looked at flowlines recorded due to surface elevation.

Figure 18:
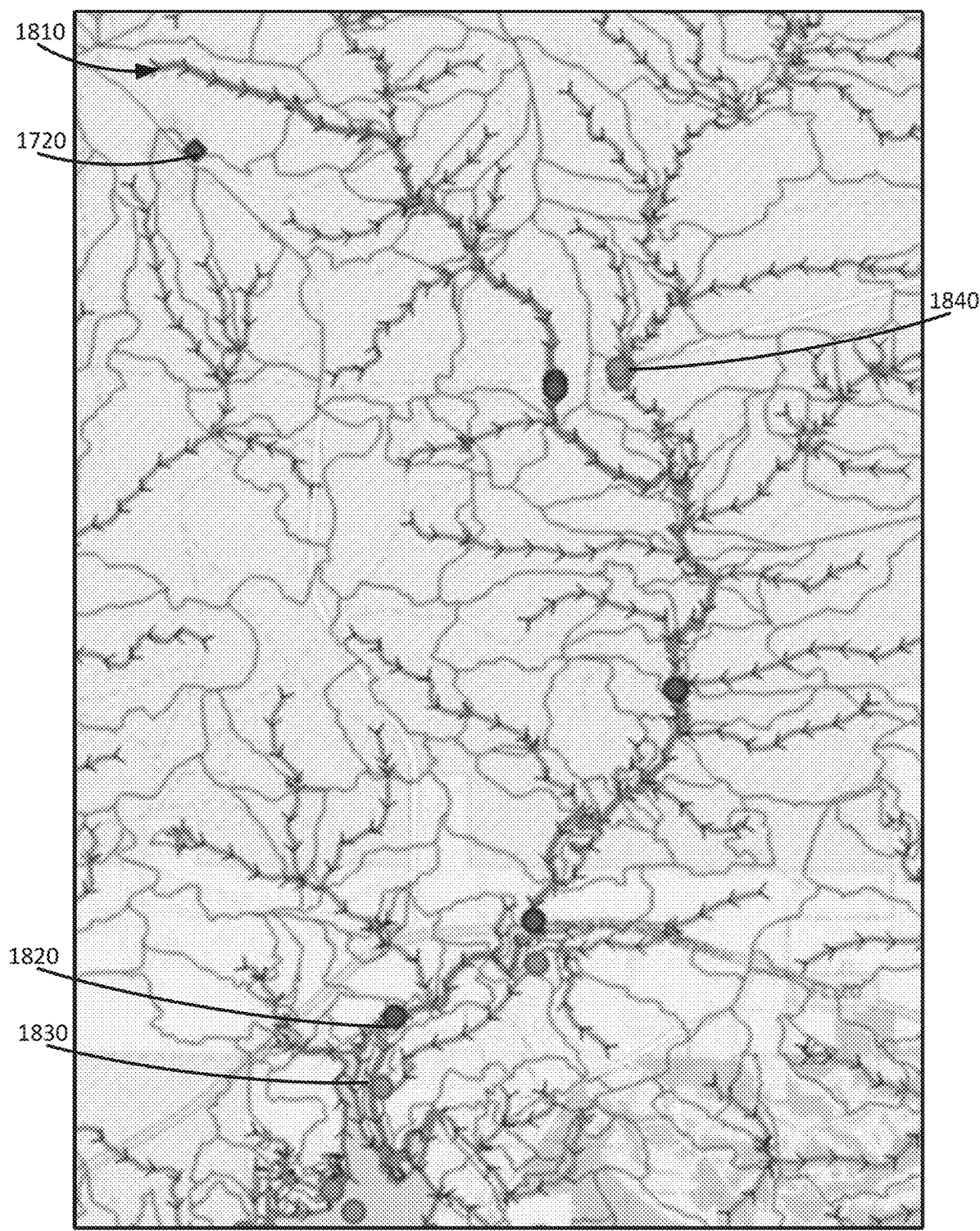
FIG. 18 illustrates an example mapping of monitoring stations in at least one embodiment of the present technology.

FIG. 18 illustrates an example mapping of monitoring stations to stressor 1720. The map images in graphical user interfaces shown herein can be taken from commercial tools. For instance, map data in one or more Figures are from OpenStreetMap.

In the graphical representation 1800 of a topography, the downstream path for this stressor 1720 is highlighted in green and begins at point 1810. In this example, monitoring stations are linked to stressors when they exist in the same hydrologic unit code layer of the U.S. Geological Survey (defining HUC8 boundaries), fall along the main flow path, and when the flowline distance of the main flowline path from the stressor to the monitoring station is 10 miles or less. Monitoring stations that get linked to the stressor 1720 are represented as red dots (e.g., monitoring station 1830). The orange dots are monitoring stations that do not get linked to the stressor because they are either upstream of the stressor (not shown), on a different flow network (e.g., monitoring station 1840), or beyond a cutoff (e.g., monitoring station 1830 is beyond the 10-mile cutoff distance). A cutoff can be customizable by a user. Additionally, or alternatively, a cutoff is dynamically or autonomously selected by a computing system (e.g., based on the type of stressor or the velocity of water flow in the flow network). Other boundaries could be used besides HUC8. For example, some states have their own identifiers for water bodies and catchments (e.g., WBID in Florida). Boundaries can be selected by a user or autonomously by a computing system (e.g., selecting a granularity to lessen orphaned monitoring stations and stressors). Additionally, users may decide to include divergent flowline pathways along with main flowline pathways in situations where flow pathways split. Main flowline pathways identify which route most of the water takes, but users may also be interested in associating an entire impact or partial impacts of an upstream object with another object on a divergent flowline pathway.

For instance, in one or more embodiments, a computing system receives an indication of a cut-off limit for selecting the one or more related data objects. The cut-off limit could be based on one or more of: geographic regions of the topography (e.g., a mileage from the stressor, or to keep analysis within the bounds of a city, county or state) and estimated attenuation of the stressor, and other limits. For instance, chemicals can have different properties in water or soil that cause them to decrease, or attenuate, over time. With biodegradation, microorganisms can breakdown contaminants so they are less toxic or nontoxic and with sorption, molecules can begin to stick to other substances so they are no longer expected to travel, with chemical transformation. Contaminants can breakdown decreasing their toxicity (e.g., radioactive decay) and pollutants can dilute or disperse into waters causing a net decrease in locations. Properties of the stressor at interest or even the terrain (e.g., a fastmoving waterflow), can be considered for setting an attenuation. This can be set by the user based on a particular project or performed autonomously by the computing system (e.g., based on a preingested or preconfigured data tables of stressor-specific attenuation limits). Regardless, based on the cut-off limit, a computing system can limit association of the identified data object to data objects in a flow network.

By using approaches described herein, monitoring stations can be selected that are more likely to measure the effect of the stressor rather than monitoring stations that just happen to be geographically closer (e.g., monitoring station 1840).

Figure 19:
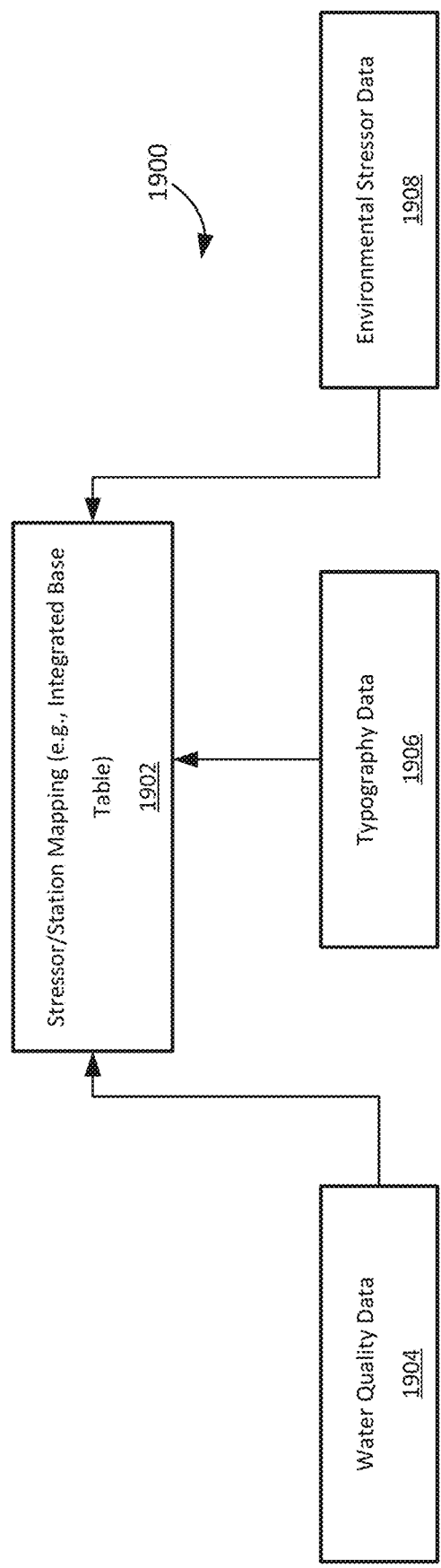
FIG. 19 illustrates example data sets for mapping in at least one embodiment of the present technology.

FIG. 19 illustrates example data sets for mapping in flow diagram 1900. One or more embodiments, join data from several sources for doing a stressor/station mapping in an operation 1902 (e.g., using an integrated base table). For example, topography data can be collected in an operation 1906 to determine terrain features such as water bodies, flowlines, catchments, etc. Water quality data can be collected in an operation 1904 to determine locations of monitoring stations (e.g., according to the topography data). Environmental stressor data 1908 can be used to determine the locations of stressor events (e.g., the causes or effects of stressors that can negatively impact water quality). Environmental stressor data could include fish kill, red tide, blue green algae, sanitary sewer overflow, weather, tidal, population, depth to water, land use land cover, and water reuse environmental stressor data to name a few.

FIGS. 20A-20D illustrate example data tables for mapping. FIG. 20A is a table 2000 of variables used in embodiments to join data from different sources (e.g., geological information and monitoring station information). U.S. Geological Survey publishes NHDPlus High Resolution (NHDPlus HR), the next generation of NHDPlus, which uses updated, high-resolution datasets to create an accessible hydrography framework in the United States. For instance, files can be downloaded indicating NHDPlus HR Flowlines, NHDPlus HR FlowlinesVAA, NHDPlus HR Waterbodies, NHDPlus HR Flow able, and NHDPlus HR Catchment files. One or more embodiments, use these files to associate environmental stressors to downstream monitoring stations. NHDPlus HR Flowlines is composed of vector line features such as canals and streams that have a reach code allowing for upstream/downstream relationships and the creation of a geometric flow network. This file also contains NHDPLUSIDs which can be used to relate to other flowlines, areas, or water bodies. NHDPlus HR FlowlinesVAA contain information on the attributes for each flowline that appears in a flow table, helping identify flow divergence and the main flow network. NHDPlus HR Waterbodies contains information pertaining to lakes, ponds, swamps, marshes, reservoirs, playas, and estuaries. NHDPlus HR Flow Table contains the directed flow of every NHDPLUSID relationship indicating how flowlines are connected from, and to, each other. NHDPlus HR Catchment contains a catchment area for either a NHDFlowline feature or a NHDPlusSink feature.

In embodiments, variables can be associated with data collected from these files. For instance, variables can be associated with flowlines 2004, flowline VAA 2006, water bodies 2008, flow table 2010 and catchments 2012, respectively in FIG. 20A. For example, column 2002 in FIG. 20A has variable names for associating with various tracked identity types (such as flowlines, water bodies, catchments, monitoring stations, and stressors identified by identity types). The remaining columns of table 2000 are marked indicating what variables are associated with which tracked aspect. As an example, a station 2014 or stressor 2016, which may be an identified or matched data object, has variables for keeping track of a geographic location (e.g., x-coordinate and y coordinate shown in table 2000). This geographic location can be used for selecting close flowlines or related data objects (e.g., ones geographically close and/or within geographic bounds based on an associated x coordinate and y coordinate). In some cases, the identified data object comprises a subset of the area. For example, if the stressor is a vegetable farm using pesticides, the entire farm may be a stressor. A computing system can determine the location for the identified data object in the topography by identifying a respective location in the typography of one or more datapoints in the subset of the area representative of the identified data object. For instance, if a monitoring station or stressor is identified by a single data point it can be considered point-based. Additionally, or alternatively, a monitoring station or stressor can be identified by multiple data points and be considered object-based (e.g., a land use/land cover (LULC) areas and onsite sewage treatment & disposal system (OSTDS) land parcels may be object-based stressors).

Flowlines 2004, water bodies 2008, and catchments 2012 may also have several geographic points associated with them and thus may have associated variables for geospatial mapping datasets (e.g., National Hydrography Dataset Plus (NHDPlus) which is a national geospatial surface water framework).

The computing system can use the identity type and the location information to determine the location of an identified object, related data objects, flowlines, water bodies, catchments, monitoring stations, stressor causes and effects. For instance, an object-based stressors may be represented as a polygon comprised of several X and Y geo coordinates. Matching an object that is represented by a polygon to a flowline may require more complex operations than matching a single point to a flowline. The polygon object can be larger and intersect with multiple flowlines, or one side may be close to one flowline while another side may be closer to a different flowline. To overcome this difficulty, different techniques can be used. For example, the centroids can be calculated and used to match to a flowline. This can be particularly useful for smaller object-based stressors (OSTDS land parcels). Additionally, or alternatively, object-based stressors can be overlayed with boundaries or zones (e.g., catchment boundaries or zones) and new polygons created based on these intersections. As previously described, catchments are areas into which surface water drains into flowlines or sinks. Catchment boundaries typically have the highest elevation such that the surface water flows downhill and drains inward from these natural boundaries. Using overlayed boundaries or zones can be particularly useful for larger stressors (LULC) that can span miles. Once new polygons are created, a computing system can calculate both the areas of these new polygons and their centroids. The computing system can match the centroids to a flowline and can use the area of the polygon to apportion the area (e.g., of an LULC type) to the matched monitoring stations.

Alternatively, in at least one embodiment, data from all new polygons can first be aggregated to the catchment level and then matched to a flowline for downstream linking. Both approaches allow for object-based stressors to be linked to more than one flowline (and potentially affect more than one flow network) if the object spans across multiple catchments.

FIG. 20B is a table 2020 of variables used to identify and establish flow networks, determine flow directions, and identify the features of flowlines as they relate to nearby monitoring stations or stressors (e.g., point or object-based stressors). Variables 2022 are associated with flowline 2024, flowlineVAA 2026, water bodies 2028, and flow table 2030 in FIG. 20B as shown in table 2020 where columns are marked indicating what variables are associated with which tracked aspect. For instance, unique identifiers can be associated with identified data objects. For example, table 2020 in FIG. 20B shows monitoring location id variable marked for stations in column 2032 and a stressor id variable marked for stressors in column 2034.

Flow table 2010 in FIG. 20A and flow table 2030 in FIG. 20B is used to determine flow connections or which flowlines feed into which flowlines. Some flowlines have "no flow", that is, they do not flow into another flowline. Alternatively, some flowlines are large and can span many miles. Occasionally a flow path will split, and water from one flowline will branch off into two flowlines. In these cases, the NHDPLUS HR FlowlineVAA data identifies which of the flow paths is the "main" path that funnels most of the water, and which is the "divergent" path that funnels less water (e.g., the main path divergence variable is checked for flowlineVAA 2026). Users may decide whether to include divergent flowline pathways or to only make associations along the main flowline pathway.

Once monitoring stations are matched to a stressor, flowlines 2024 shows a checked category for a LenthKM variable to keep track of a total summed length of each flowline in the path between the stressor and station (e.g., in kilometers). Theoretically, this path could stem from the most northern tip of a geographic area to the southern tip of that same area, which can represent hundreds of miles in distance. A computing system can use this length for performing cut-off calculations.

FIG. 20C shows a table 2060 of analytics that may be potential sources of stressors to land or water, or effects of stressor, which can be monitored by monitoring stations. For instance, description column 2062 describes different analyte types and different measures for those analytes in measure column 2064. Some analytes may be grouped together as shown in table 2070 of FIG. 20D. Other water quality monitoring stations could collect data on different analytes than shown in FIG. 20C, measure the analytes in different units, or group them differently.

Figure 21A:
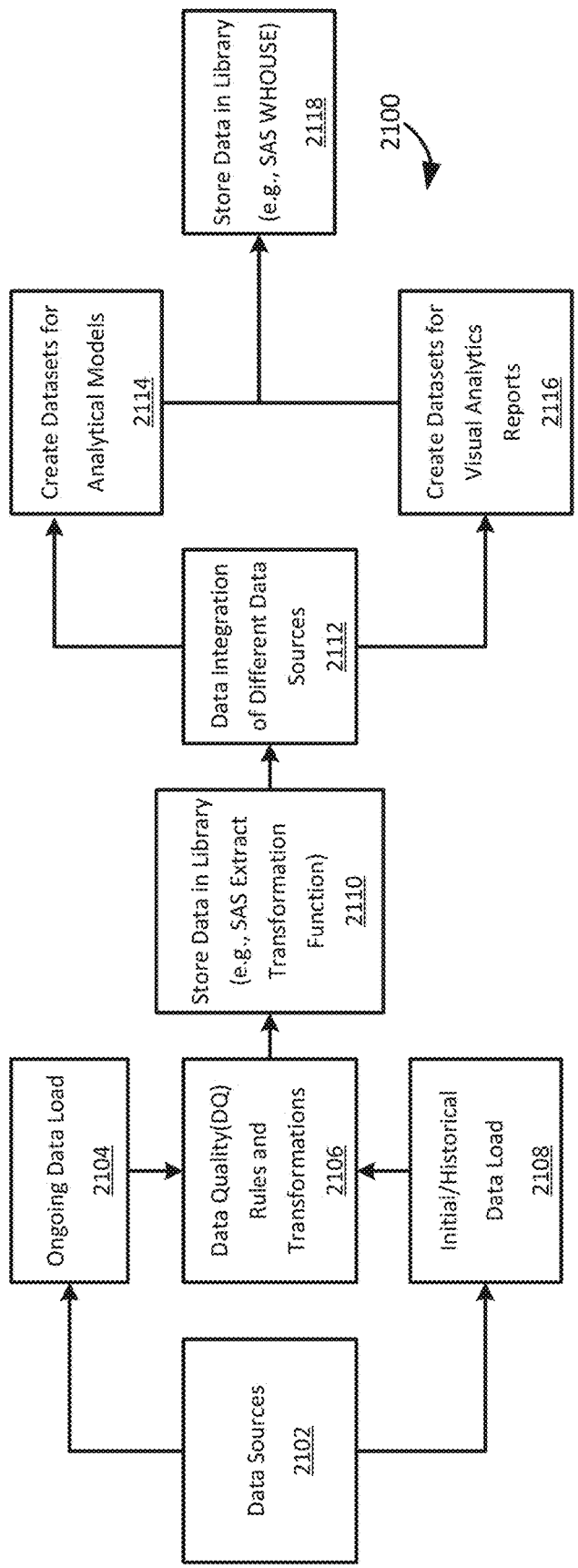
FIGS. 21A-21B illustrate example flow diagrams for displaying data reports and models for mapped objects in at least one embodiment of the present technology.
Figure 21B:
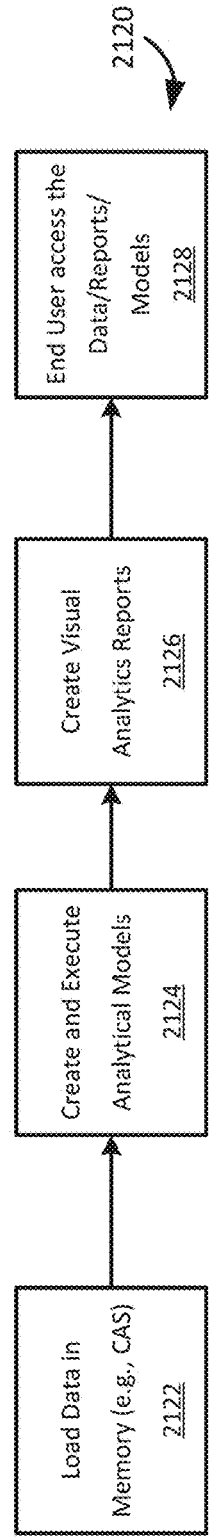

FIGS. 21A-21B illustrate example flow diagrams for displaying data reports and models for mapped objects. Method 2100 and method 2120 are an example of extract, transform, and load (ETL) process. Data integration enables the combination of different types of data in what are called ETL jobs. This is the process by which the various data are combined into a single data warehouse with multiple tables (tied to the relevant analytic objectives) that are then used to inform and conduct the analytic processes and produce the Graphical User Interface (GUI) design. For example, FIG. 21A shows a method 2100 for an ETL process. Data sources 2102 (e.g., water quality data, typograph data, and environmental stressor data discussed in reference to FIG. 19) are used, for example, for ongoing data load 2104, and initial or historical data loads 2108. Once data is loaded, data quality rules and transformations operations 2106 can be applied. For instance, data variables with >95% missing information may not be useful to future models and therefore may be excluded from analysis. As another example, variables or features can be eliminated that are not related to associating stations or stressors with flowlines or identifying flow networks or direction. In operations 2110, a computing system can store processed data in a library (e.g., using the Extract Transformation function of the SAS® Data Integration Tool). In operations 2112, a computing system can perform data integration with different data source (e.g., to merge information or derive new information such as location information within a topography). The integrated data can be used, for example, for creating datasets for analytical models in an operation 2114 or for visual analytics reports in an operation 2116. The datasets can be stored in a library in an operation 2118 (e.g., SAS® warehouse).

Figure 22A:
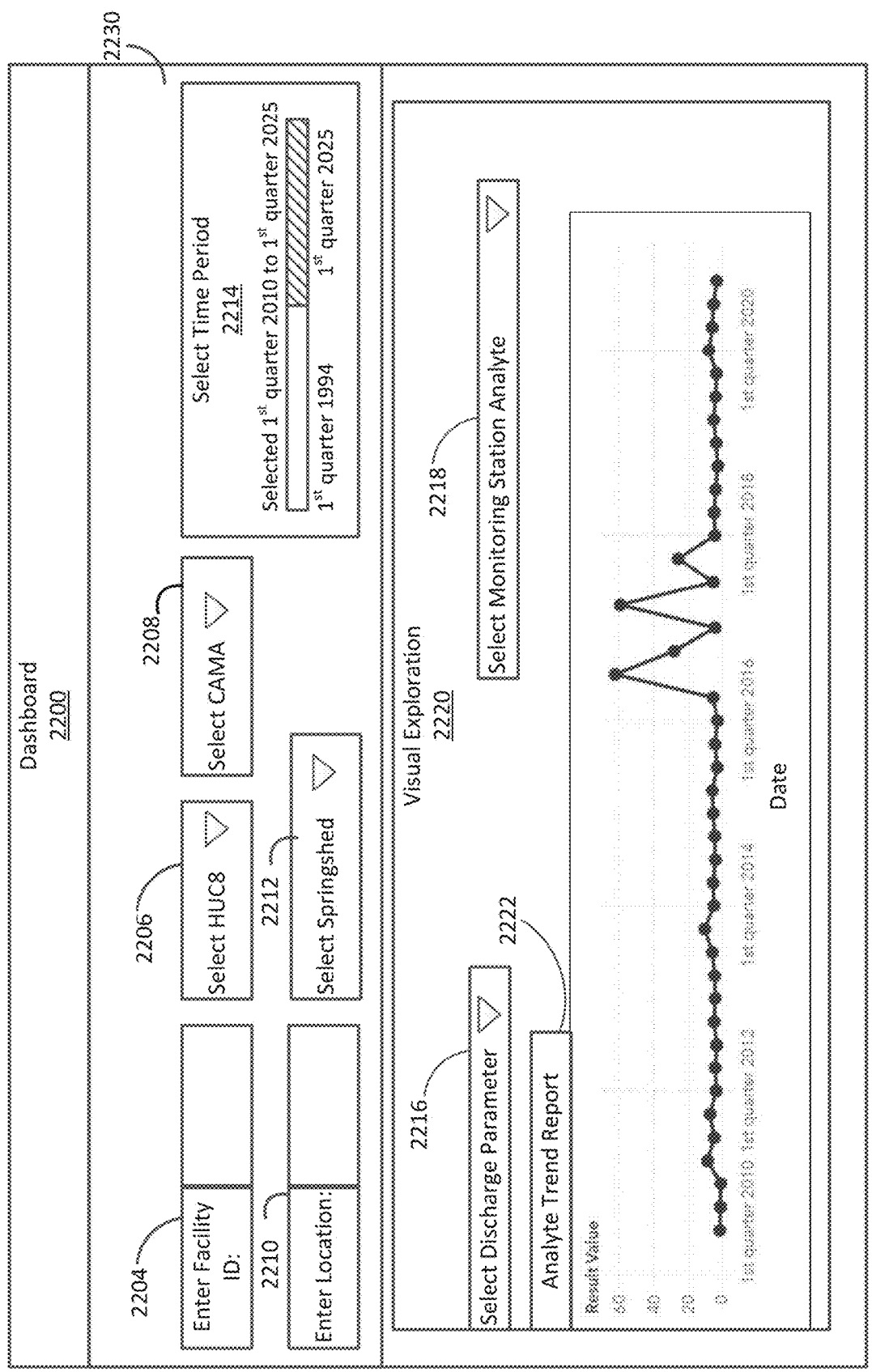
FIGS. 22A-22B illustrate example graphical user interfaces for displaying graphical representations of measurements for a stressor mapped to one or more monitoring stations in at least one embodiment of the present technology.
Figure 22B:
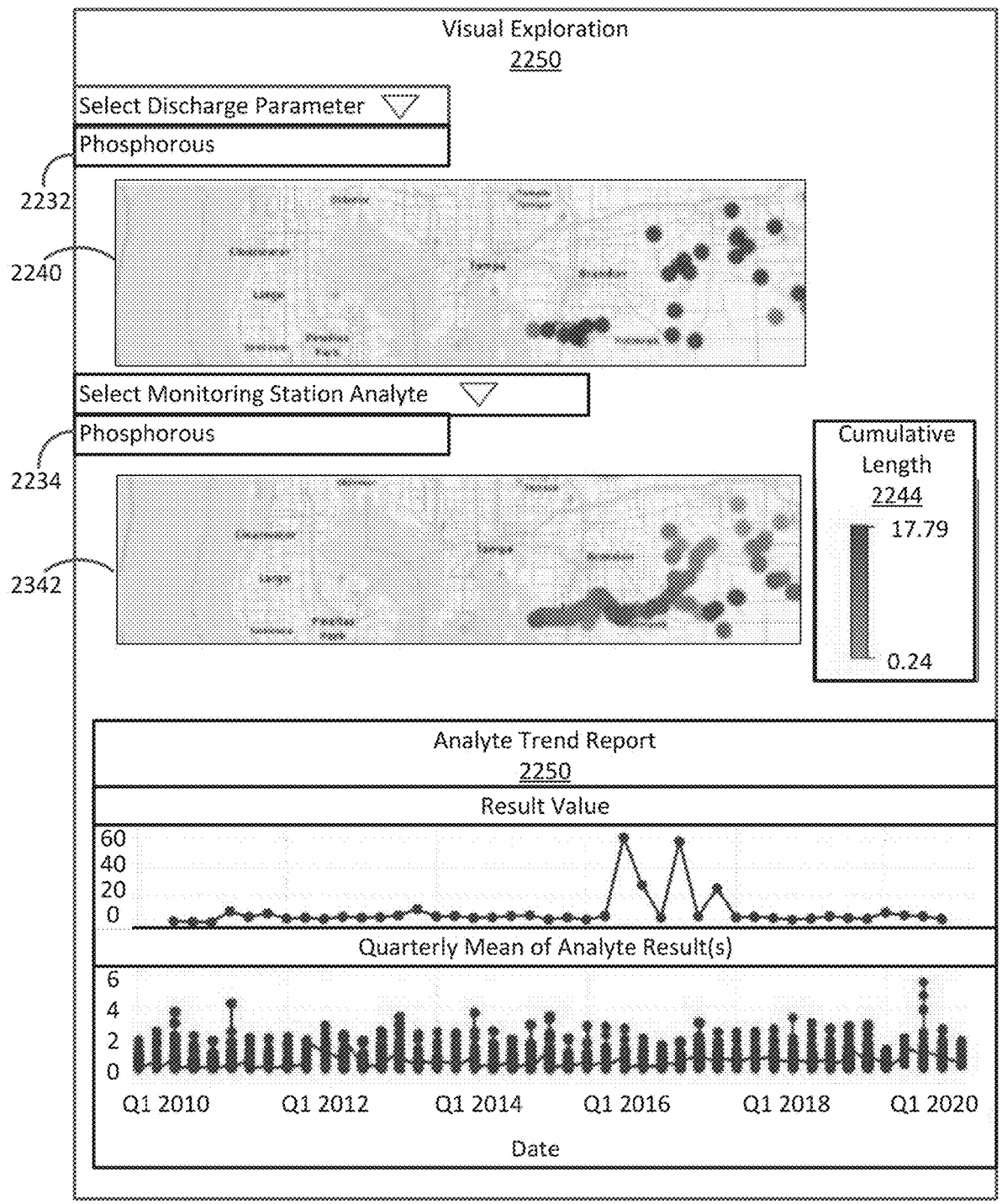

FIG. 21B shows a method 2120 for using stored data (e.g., according to method 2100). Data can be loaded into memory (e.g., a CAS memory) in an operation 2122. For instance, it can be loaded from a library location discussed in operation 2118. Data can be used to create and execute analytical models in an operation 2124, create visual analytics reports in an operation 2126 and provide end user access to the data, reports, and/or models in an operation 2128. FIGS. 22A-22B provide example user access to data, reports and/or models according to the methods in FIGS. 21A-21B.

FIGS. 22A-22B illustrate example graphical user interfaces for displaying graphical representations of measurements for a stressor mapped to one or more monitoring stations. For instance, this example allows a user to explore the relationship between wastewater treatment facility discharges and downstream monitoring stations (e.g., by aggregating analytes spatially and over time, and applying new hypothetical limits to existing discharges to see how many facilities could be affected, and to estimate the potential expected change in outfall loading). For instance, in the portion 2220 of the visual exploration tab, a user can use the drop-down box 2216 to select a discharge parameter (e.g., an analyte discharged at a wastewater facility) and an analyte for monitoring in the drop-down box 2218. For instance, if phosphorous (a common ingredient in fertilizers and sewage waste) was discharged at one site, monitoring stations may be selected to also monitor for phosphorus. Alternatively, the monitored analyte may be different. For instance, phosphorus can speed up eutrophication reducing dissolved oxygen, so dissolved oxygen may be a more important analyte to measure to a user. Every monitoring station may not measure every analyte, so this approach further narrows monitoring stations of interest.

Additional global filters 2230 allow the user to make selections in the dashboard 2200 shown in FIG. 22A for information displayed in the Visual Exploration tab (e.g., portion 2220 of the visual exploration tab). The facility information identifier textbox 2204 can be used to enter a facility identifier (e.g., a wastewater facility) to refine data. The location textbox 2210 can be used to refine or cutoff data to a particular location (e.g., a city, a county or state territory). These textboxes can utilize predictive text input, meaning it will start populating options that meet the text being entered. Other filters not specifically shown can be present. Drop-down menus can also be provided as a filter (e.g., to select boundary or zone tools such as HUC8 Selection in drop-down box 2206, CAMA Selection in drop-down box 2208, and Springshed selection in in drop-down box 2212).

The time period slide 2214 allows the user to select a date range (e.g., by quarter) for the measurements and trends for the selected analyte. Multiple report measurement tools can be used. For instance, outfall discharge data and monitoring data can be aggregated at the quarterly level and summary tables can display data at an annual level. Missing data will be filled in with the previously recorded measurement if a measurement value can be found (e.g., in the previous 31 days); otherwise, the value will be left as missing (null value). Specific analytes or analyte groups could be selected or preconfigured for inclusion in the dashboard (e.g., analytes shown in FIG. 20C, or analyte groups shown in FIG. 20D).

In analyte trend report tab 2222, measurement results for the analyte aggregated over downstream monitoring stations can be displayed to look for abnormal spikes that may indicate a stress to an environment (e.g., a stressor event may have occurred in 2016-2017). Graphs in the dashboard 2200 can be interactive. For instance, hovering over a point in the line graph of analyte trend report tab 2222 will provide a popup with the measurement for that point.

FIG. 22B shows an expanded view 2230 of the visualization tab. In this example, a discharge parameter 2232 of phosphorous is selected. The computing system receives, using a graphical user interface, the indication of an identified data object that represents a stressor to an area. A monitoring station analyte 2234 of phosphorous is selected. The computing system, responsive to these selections, displays in the graphical user interface information derived from multiple monitoring stations associated with one or more related data objects (in this case data objects determined to represent monitoring stations downstream and measuring the appropriate analyte).

The geomap 2240 displays the locations of the discharge facilities that meet the geospatial and time period selections in the global filters. The color of the dot indicates different facility types (e.g., here there were two facility types). If a user clicks on a dot, the computing system will filter the monitoring stations in geomap 2242 to show monitoring stations that are downstream from the selected facility.

The geomap 2242 displays all the monitoring stations that meet the criteria selected for the visual report. The color of the dot indicates the distance between the discharge facility and a monitoring station along the flow path when a discharge facility is chosen (e.g., by selecting one or more dots on the geomap 2240). However, when no specific facility is chosen, the color of the dot indicates the average length of the flow paths from all discharge facilities. Lighter dots indicate a shorter distance while darker dots indicate a longer distance.

In this embodiment, a cumulative length slide 2244 allows for adjusting the cumulative path lengths in kilometers for displayed monitoring stations. For instance, the user can adjust a cut-off length specifying the longest length for a flow path (e.g., 17.79 kilometers) or a beginning length specifying the shortest length for a flow path (e.g., 0.24 kilometers). An analyte trend report 2250 displays information regarding analytes monitored.

It should be noted that the cumulative length slide 2244 may not be present in some embodiments. For example, in at least one embodiment, the information provided by the cumulative length slide 2244 comprises a legend. In such embodiments, the user would not be able to adjust the cumulative path length, as above. However, the user would be able to identify, from the information in the legend, the shortest and longest flowline lengths between a given stressor to a given station in kilometers. Additionally, such a legend could also represent longer distances using darker colors and shorter distances using lighter colors, as previously described.

Figure 23:
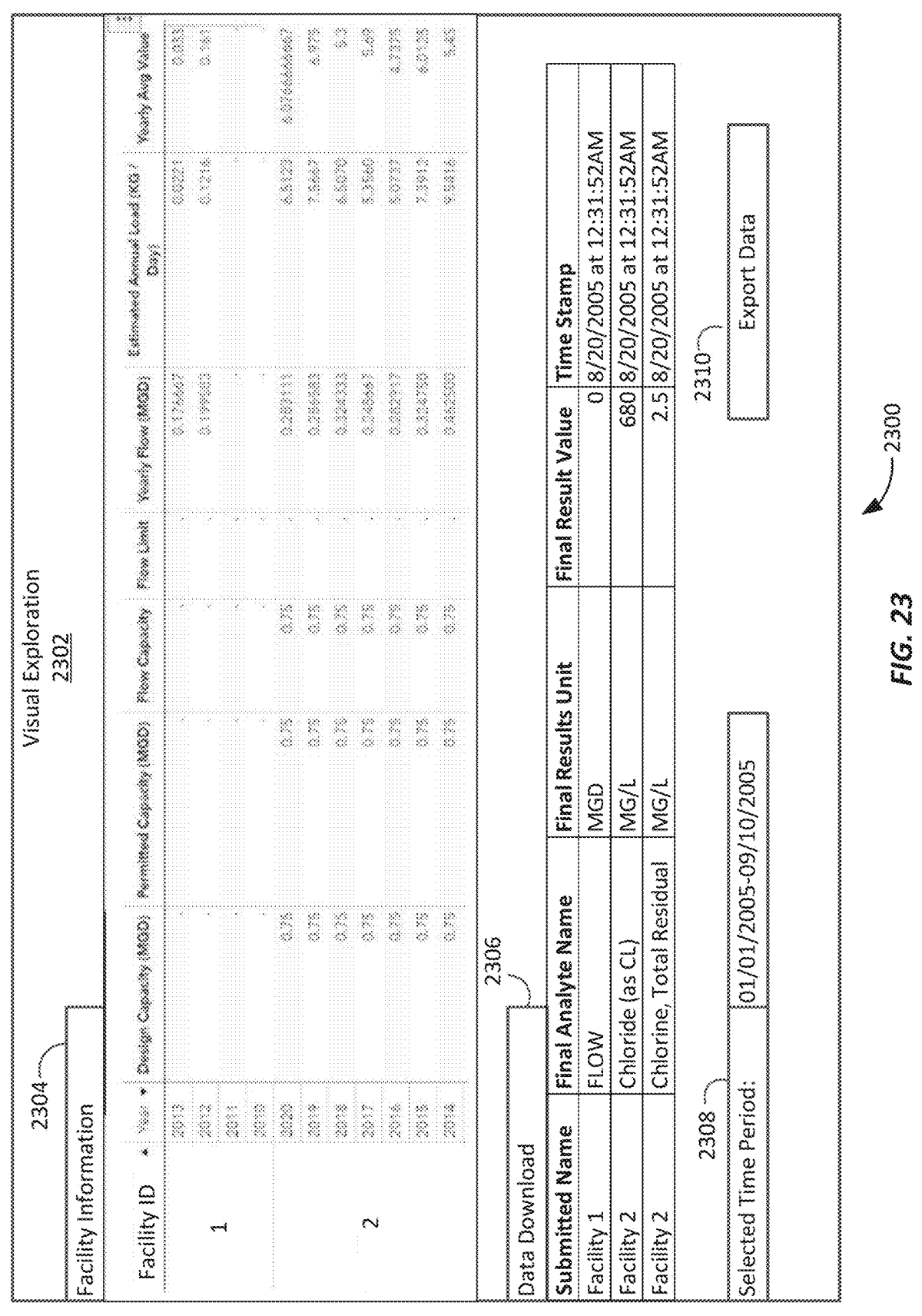

FIG. 23 illustrates an example graphical user interface 2300 for displaying graphical representations pertaining to multiple wastewater treatment facilities. Facility information 2304 displays information pertaining to different identified facilities (e.g., facility ID 1 and 2), across different years. It displays information such as how the facility was designed and permitted compared to what it is actually discharging.

Individual information on an analyte can be downloaded using data download control 2306 filter for certain time periods using filter 2308 and exported for use in reports or modeling using export control 2310.

Figure 24:
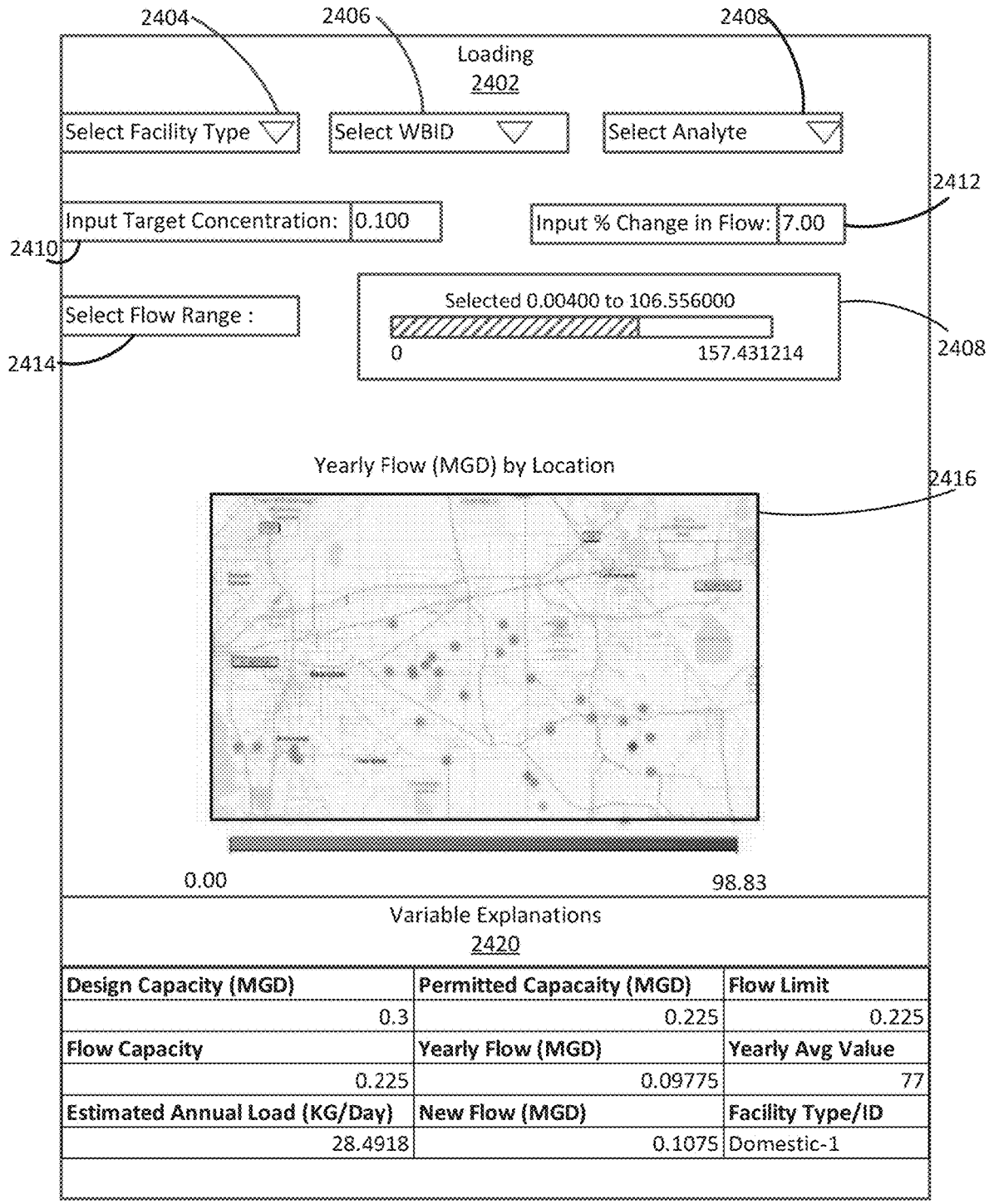
FIG. 24 illustrates an example graphical user interface for generating a report about a stressor in at least one embodiment of the present technology.

FIG. 24 illustrates an example graphical user interface 2400 for generating a report about a stressor. In one or more embodiments, a computing system can receive, according to the one or more controls, an indication of measurements of the effluent discharge. Based on the measurements, the computing system can generate one or more computer models to predict measurements in the area due to the stressor and display in a graphical user interface graphical representations of one or more of the measurements and predicted measurements from the computer model.

For instance, the load tab 2402 allows a user to explore 'what if' for outfall loading data for facilities by type and area. It includes the ability to see hypothetical effects of a regulatory changes based on actual discharges rather than permitted capacities. The user can apply a hypothetical new limit to existing discharges and/or target concentrations to explore how many facilities could be affected (grouped by facility type) and estimate of the potential decrease in outfall loading that could be expected. This potential decrease in loading is shown by converting the decrease in concentration while maintaining the historical flow and converting into a mass measurement. However, flow levels can be changed by a chosen percentage for all selected facilities if desired.

For instance, the facility type drop-down 2404 allows a user to refine information to a certain facility. Select water body identifier (WBID) drop-down list 2406 allows to refine the data to a certain water body. Analyte Selection drop-down list 2408 allows to refine the data to a certain analyte monitored. Flow Range Selection 2414 can be used by a user to limit or expand the flow range (e.g., in MGD). Target Concentration Input 2410 can be used by the user to adjust the target concentration for the selected analyte to visualize the potential impact of the increase or decrease in that concentration. Percent Change in Flow Input 2412 can be used by the user to adjust the change in flow (e.g., in MGD) by a chosen percentage to visualize the potential impact of the increase or decrease in that flow.

A geomap 2416 displays the location of the stressors that meet the criteria selected in the dashboard and tab filters. The color indicates the annual flow in MGD with darker colors representing higher flow. A Granular Loading Table (not shown) displays information about the stressor facility that meets the criteria of the filters for the dashboard and tab. The user can double click a row to drill down into annual information from that facility. For instance, the Variable Explanations tab 2420 provides the description of the variables included in the Granular Loading table. The map data for this geomap 2416 came from OpenStreetMap.

In one or more embodiments, greater distinctions can be made to the type and nature of topography aspects in associating data objects (e.g., associating a stressor and monitoring station). For instance, water bodies can be treated differently by a computing system depending on its type.

Figure 25:
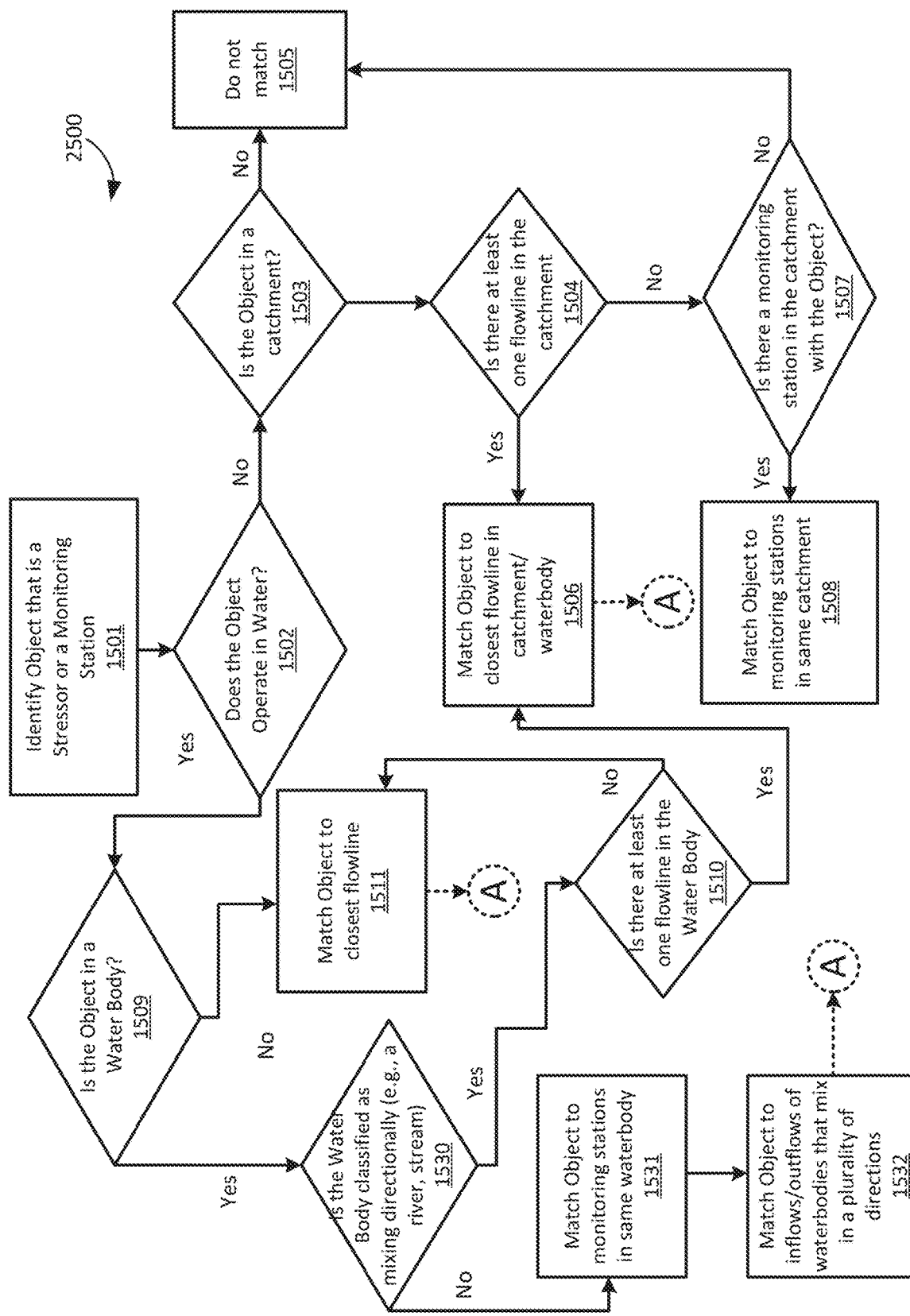
FIG. 25 illustrate a flow diagram for developing a flow network according to at least one embodiment of the present technology.

FIG. 25 illustrates a portion 2500 of flow diagram for developing a flow network. FIG. 25 is a modification of the flow diagram in FIGS. 15A-15B, and as such, contains similar operations. Therefore, only those operations of FIG. 25 that are new or appear along a path that is different from those of FIGS. 15A-15B are discussed below in more detail.

The flow diagram of FIG. 25 considers variations in water bodies related to whether water bodies should be classified as mixing directionally (e.g., a pollutant entering into a river or stream may mix in in the direction of the water flow down the stream) or in many different directions so as to be treated as if mixing near instantaneously (e.g., estuaries and lakes may have lots of different forces causing a pollutant entering in one location to travel to many different areas of the estuary or lake).

In operation 1501, an object is identified as being one of a stressor or a monitoring station. In one embodiment, the object may be identified as being a source stressor or an effect stressor. So identified, it is determined in an operation 1502 whether the identified data object operates in water. As previously described, this determination can, in some embodiments, be implicitly determined (e.g., assuming all water quality monitoring stations operate in water, or that stressors (i.e., source stressors and/or effect stressors) of a certain type always operate in water or on land). Alternatively, in some examples, a topography may only comprise water (e.g., in a system of lakes) or only contain land, in which case only one side of the flow diagram would be operational for a particular case. In this example, operation 1502 determines that the identified object operates in water.

In an operation 1509, if it is determined that an object is in a water body, additional operations can be performed to further classify the water body. In this case, in an operation 1530, it is determined whether the water body is classified as mixing directionally. For instance, a computing system may have been preconfigured, or in response to a water body classification, to group one or more water bodies in a topography. For instance, water bodies can be grouped into a first group comprising water bodies classified as mixing directionally, and other water bodies can be grouped into a second group comprising water bodies classified as mixing in a plurality of directions. Additionally, in at least one embodiment, a water body can be grouped with one or more adjacent waterbodies and treated as a single water body that mixes in a plurality of directions. One of ordinary skill in the art will appreciate water bodies could be classified into more groups (e.g., groups with oscillating or periodic directionalities such as ones with tidal properties) with associated operations to further determine how an identified object should be associated. The portion 2500 of a flow diagram in FIG. 25 uses a two-group classification merely for example.

If in the portion 2500 of the flow diagram an identified data object is determined to be in a first water body of the second group (i.e., it is assumed to not mix directionally), the computing system can match objects to monitoring stations and other stressors in the same water body in an operation 1531. For instance, the computing system can select one or more related data objects from the available data objects by associating the one or more related data objects in the first water body to the identified data objects. Additionally, in some embodiments, the computing system matches, in an operation 1532, identified objects to all flows into (i.e., inflows), and all flows out of (i.e., outflows), the first water body. Such information enables the computing system to calculate both the upstream and downstream flow paths for linking with one or more related data objects along a flow path.

If an identified data object is instead determined to be in a first water body of the first group (i.e., it is assumed to mix directionally), the computing system can determine in an operation 1510 whether there is at least one flowline in the water body. When there is at least one flowline in the first water body, in an operation 1506, the identified data object is matched to a closest flowline (e.g., by associating the identified data object with a closest flowline intersecting the first water body). When there is not a flowline in the first water body, the computing system can associate the identified data object with a closest flowline in an operation 1509. The computing system can then select one or more related data objects according to the flow diagram in FIG. 15B. For instance, the computing system can select the one or more related data objects based on an association with a flowline. Other operations in FIG. 25 can follow the same operations as described with respect to FIGS. 15A and 15B.

Figure 26A:
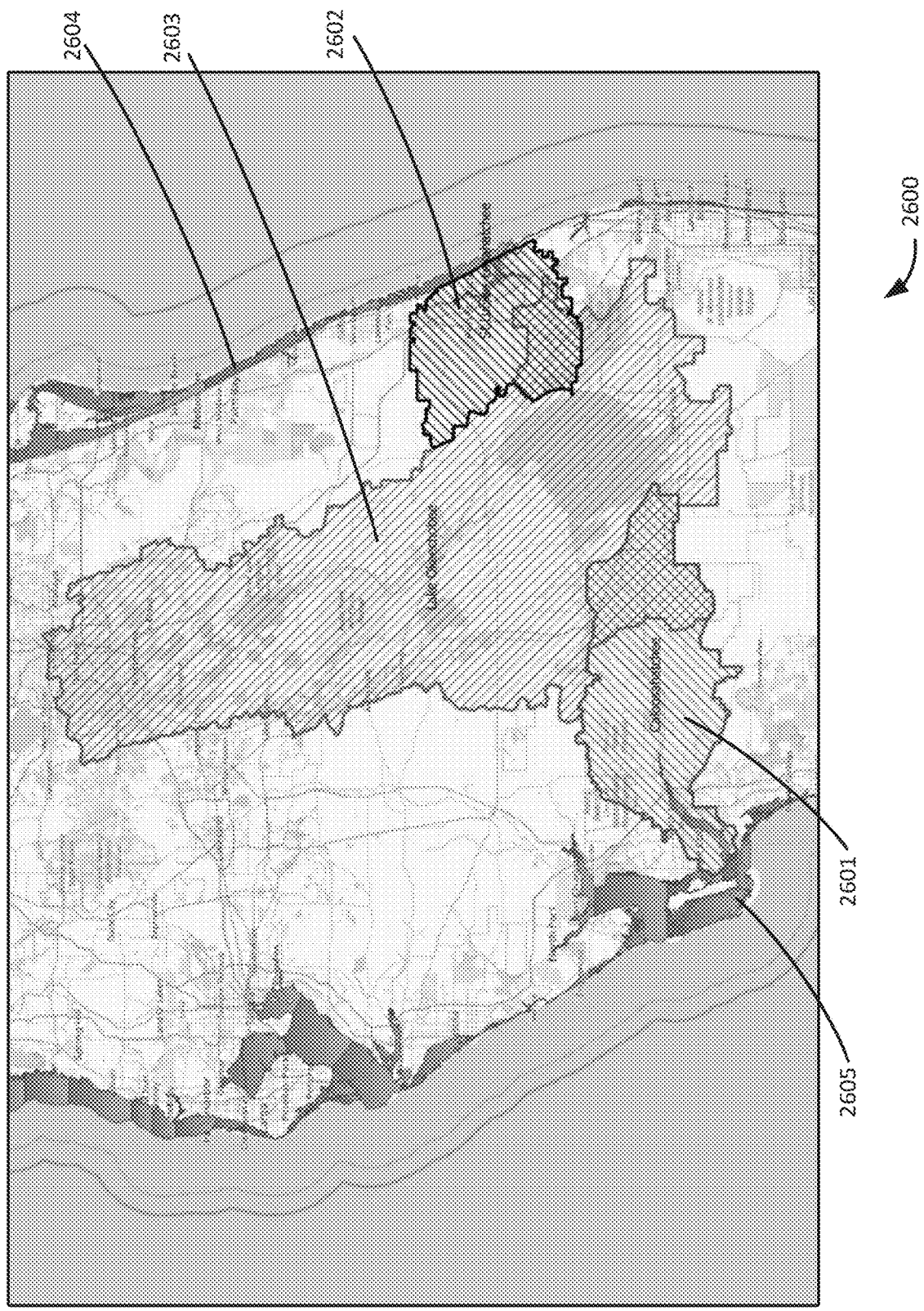
FIGS. 26A-26C illustrates an example graphical user interface for classifying different water bodies in at least one embodiment of the present technology.
Figure 26B:
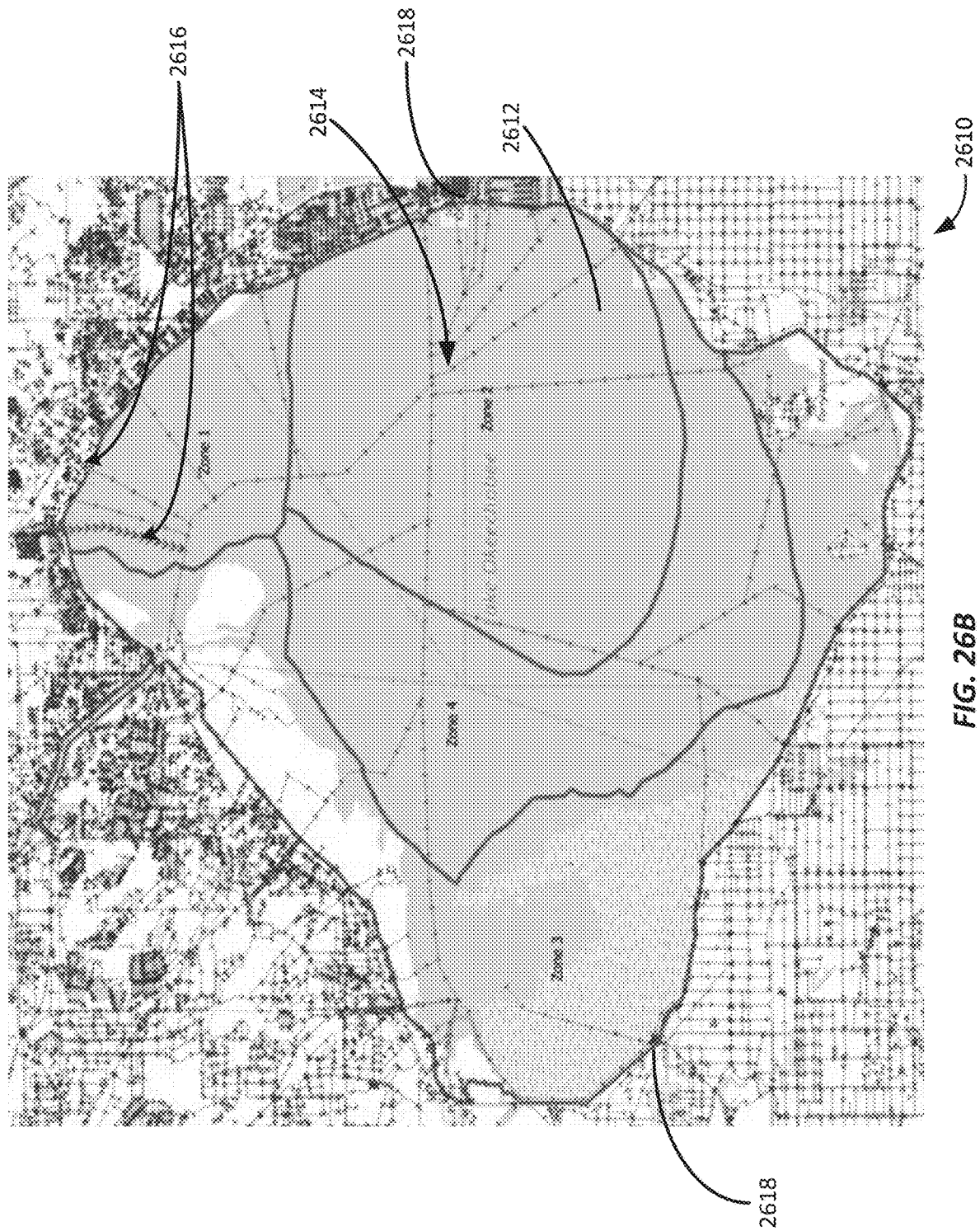
Figure 26C:
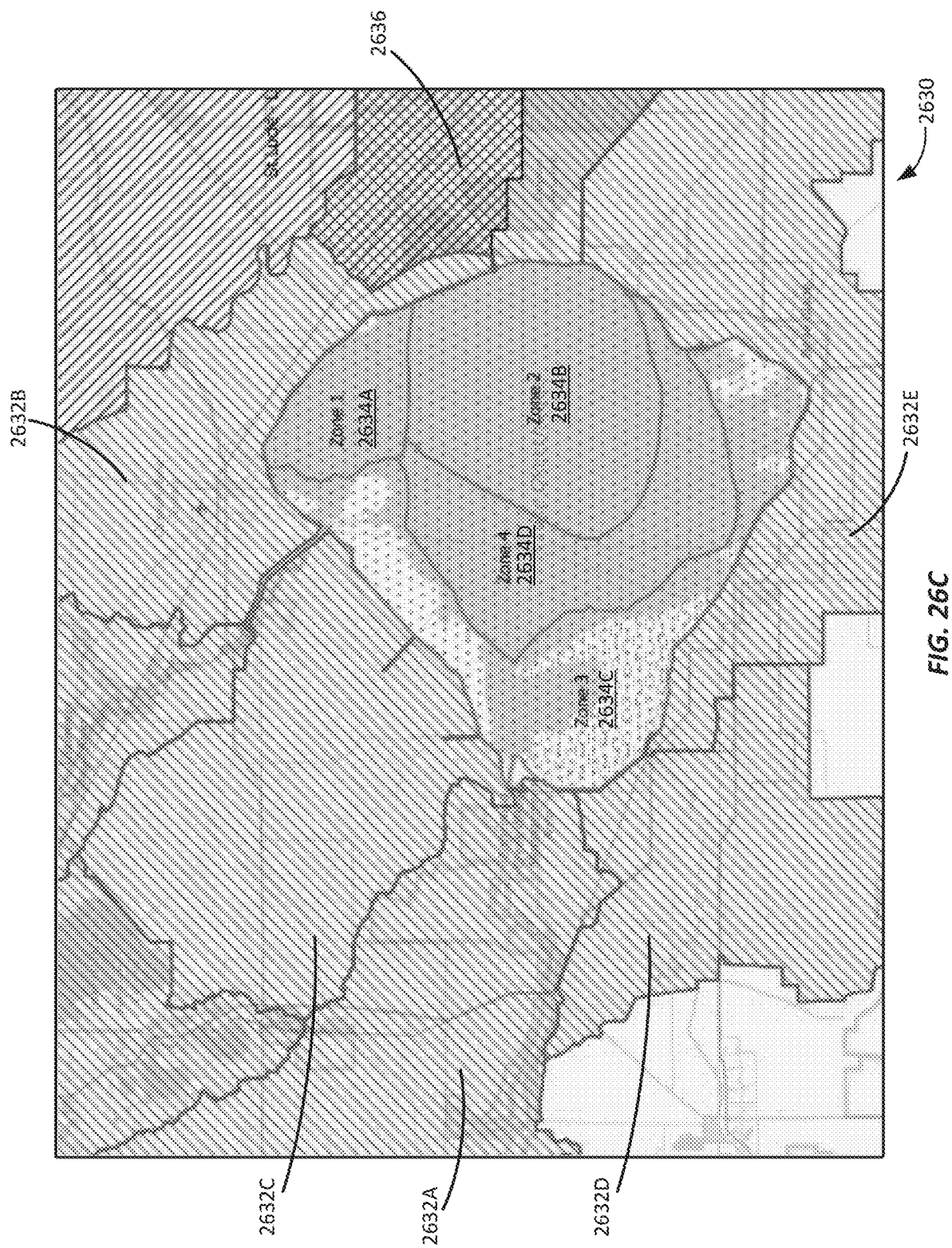

FIGS. 26A-26C illustrates an example graphical user interface classifying different water bodies. In this example in FIG. 26A, basin management action plans (BMAPs) were used to identify the boundaries within a terrain. In this example, only 3 BMAPS in Florida are shown to look at linking monitoring stations and other stressors to a Blue Green Algae (BGA) event in estuaries or Lake Okeechobee in Florida. The 3 BMAPS include Caloosahatchee BMAP 2601 (in green), St. Lucie BMAP 2602 (in black), and Lake Okeechobee BMAP 2603 (in blue). This example uses subwatersheds as boundaries within these BMAPS. Subwatersheds are shown and described in more detail with reference to FIG. 26C. The BMAP boundary for St. Lucie BMAP 2602 does not extend all the way to the coast. This means that while the landward portion of the estuary that falls within the black border would be included, the larger portion of the coastal estuary 2604 (in orange) would not be included since it does not fall inside the BMAP boundary. The same applies for the Caloosahatchee BMAP 2601, where the larger portion of the estuary 2605 (in orange) toward the Gulf is not included in the Caloosahatchee BMAP 2601 boundary. Additionally, this example uses coastal flowlines as terminal paths as a cut-off described in more detail with respect to FIGS. 28A-28B.

FIG. 26B shows a portion 2610 of the Lake Okeechobee BMAP 2603 with a lake area 2612 (in blue). For this lake area 2612, all flowlines shown in purple (e.g., flowline 2614), other than inflows shown in orange (e.g., inflows 2616) and outflows shown in red (e.g., outflows 2618) were ignored. As defined herein, an outflow is a flowline that begins inside of a body of water (e.g., lake area 2612 and terminates outside of that body of water. However, an inflow is defined herein as a flowline that begins outside of the body of water (e.g., lake area 2612) and terminates inside of that body of water. In some embodiments, e.g., where a lake is large, zones of instantaneous mixing can be identified, and the lake can be partitioned into two or more zone polygons accordingly.

In one or more embodiments, a topography can indicate bounds for one or more water bodies and one or more catchments. The computing system can generate multiple regions in a given bounded area of the multiple bounded areas (e.g., the zones in FIG. 26C). This is particularly useful in a situation where there are known areas/zones of instantaneous mixing in a water body.

In FIG. 26C, the BMAP for Lake Okeechobee is broken into subwatershed areas in pink (e.g., subwatershed areas 2632) and Lake Okeechobee is shown represents as a bounded water body in blue. Objects can be divided into regions of instantaneous mixing based on supplemental topographical data. For instance, in this example Lake Okeechobee is shown split into 4 zones (zones 2634A, 2634B, 2634C, 2634D). A computing system can determine the location of identified data object is in a first region of the multiple regions. The computing system can select the one or more related data objects from the plurality of data objects by: associating, based on the location, the identified data object with the inflows and outflows in the first region of the multiple bounded areas; and selecting the one or more related data objects that also exist in the first region. For example, all monitoring stations in Zone 2 can be linked with all Blue Green Algae events in Zone 2. In other words, zones can be treated as separate water bodies for analysis and inflows and outflows (e.g., flowlines 2616 and 2614 shown in red and orange in FIG. 26B, respectively) in individual zones considered for upstream and downstream linking.

If a monitoring station and/or stressor event occurs in an area of overlap (e.g., overlap area 2636 where the pink Lake Okeechobee subwatershed and the Black St. Lucie BMAP overlap), that data object can be contained in the St. Lucie data with all upstream/downstream associations that exist within the thick, black border, as well as in the Lake Okeechobee subwatershed data with upstream/downstream associations that exist within the thick, pink border.

Each zone in Lake Okeechobee was linked in a flow network with any and all subwatersheds that it connects to. For example, Zone-1 2634A is linked only to the Subwatershed 2632B and Zone-3 is linked to 5 subwatersheds (2634A-E) it is adjacent to. Where there are gaps between the Lake Okeechobee zone polygons and the subwatershed boundaries, the computing system extended the zone polygons outward to meet the subwatershed boundaries. In other words, buffers can be created to account for an entire land or water area.

Figure 27:
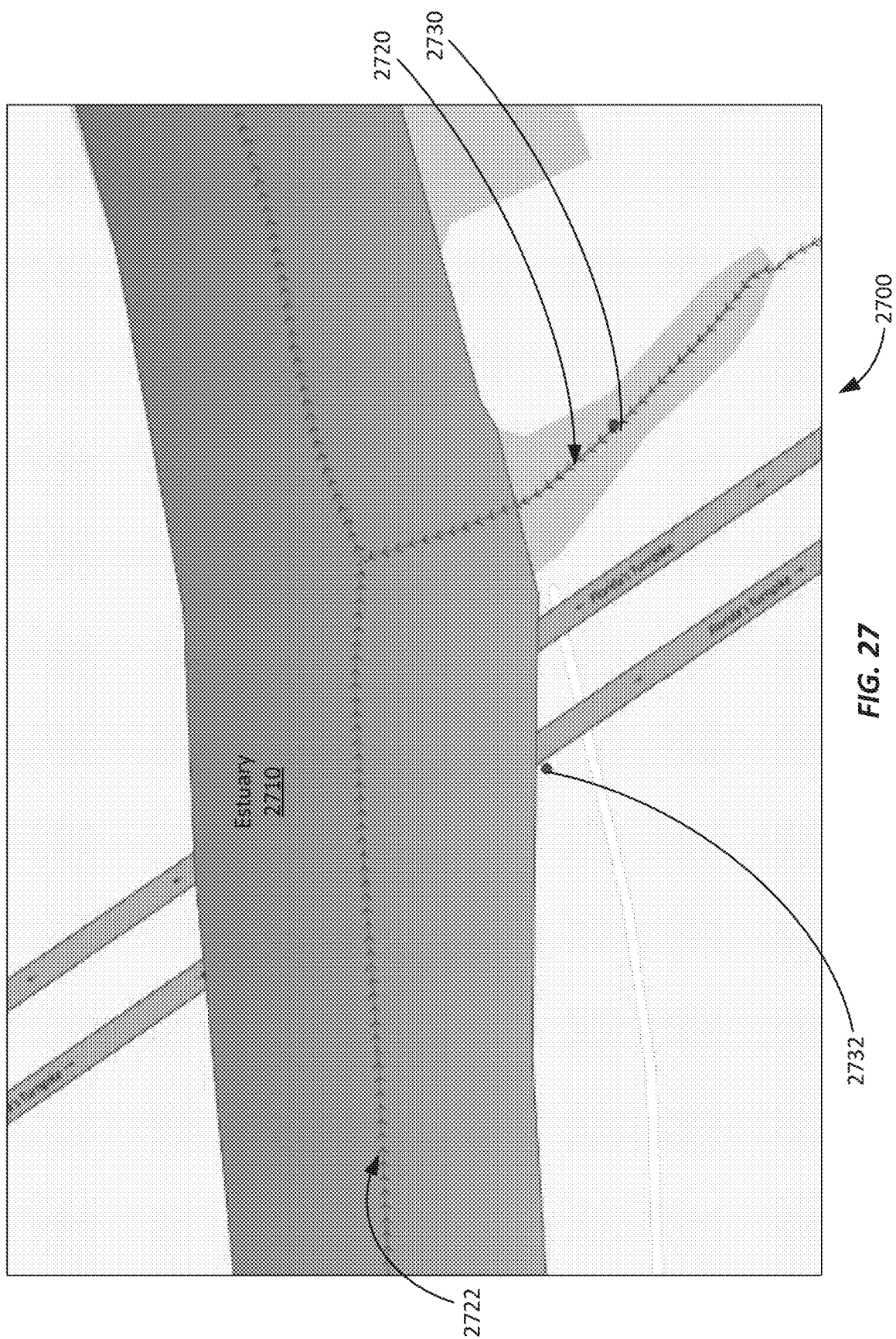
FIG. 27 illustrates an example graphical user interface for mapping a monitoring station near an estuary to the estuary using a buffer in at least one embodiment of the present technology.

FIG. 27 illustrates an example graphical user interface for mapping a monitoring station and/or stressor using buffers. In this example, point 2730 and point 2732 could each represent a monitoring station, a stressor cause, and/or a stressor effect. A 100-meter buffer was given for the estuary 2710 shown in orange on the map 2700. This buffer allows point 2732 and point 2730 to be associated with estuary 2710 and all inflows into and outflows out of estuary 2710. Buffers can be particularly useful for accounting for situations in which geographical coordinates of an event, data object, land or water boundary, may be reported or projected slightly incorrectly.

Figure 28B:
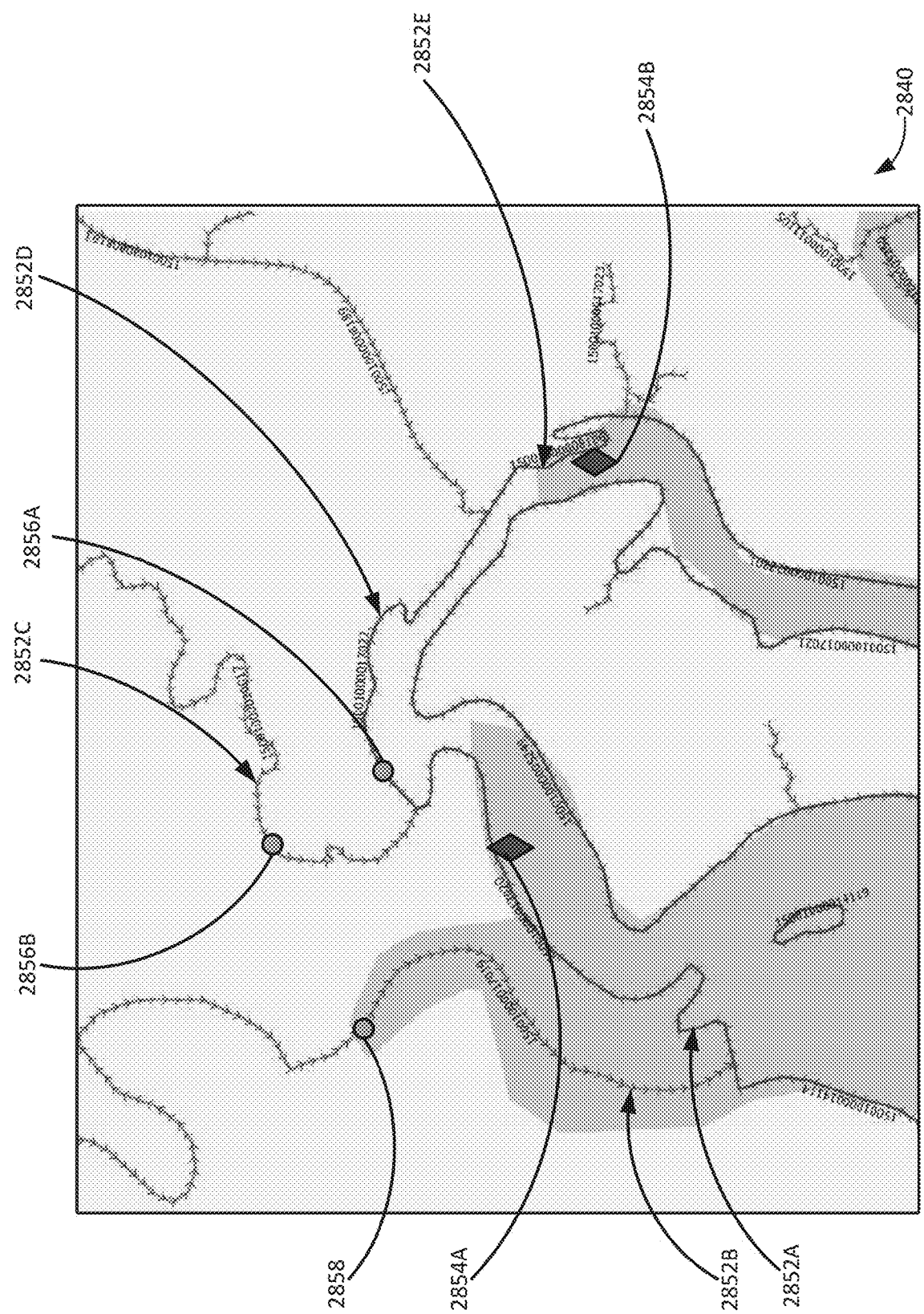

FIGS. 28A-28B illustrate an example for determining a flow network near a coastline. FIG. 28A shows a table 2800 of different types of flowlines in the NHDPlus HR dataset for Florida. Particular types of flowlines could be excluded or treated differently based on the feature type shown in feature type column 2802. For instance, flowlines of type "coastline" could be excluded or treated as terminal flowlines for flow networks. If coastlines are considered a terminal path to the ocean, inland flowlines can flow into costal flowlines (and into estuaries), but the path will stop there and not continue along the coast into additional flowlines. To do this, the computing system could match all costal flowlines to the "from" connection on the flow table and remove these records. This takes away the "To" connection to these flowlines. However, this will leave the costal flowlines in the "To" connections in the flow table to capture the flow that is flowing out into a coast/ocean location. In other words, once a flow path flows into a coastal flowline, the flow path ends, and mixing with the ocean is assumed. Additionally, coastal flowlines will still be in the flowline shape file, meaning that stressor events, monitoring stations, and stressors can all still be matched to this coastal flowline if it is the closest flowline, but this flowline would not be considered upstream of any other flowline (it is only considered to be downstream).

FIG. 28B illustrates an example topography with coastal flowlines. In this example, coastal flowlines are depicted in red. Non-coastal flowlines are green. Monitoring stations and/or stressors are located at orange dots and stressor effects are located at purple diamonds.

Monitoring stations and stressors can be linked according to the coastal nature of the flowlines. For instance, if an effect was reported in a coastal location (e.g., a BGA event occurs on the coast), it will get linked to the coastal flowline (and any monitoring station/stressor that is also matched to that same coastal flowline). If a non-coastal flowline flows into the coastal flowline associated with the BGA, the computing system will match the BGA event to all upstream non-coastal flowlines along the flow path. The BGA event will be tied to all monitoring stations/stressors that occur along this flow path into the coast/ocean. If, however, only another coastal flowline flows into this BGA coastal flowline, the computing system will not match the BGA event to the upstream coastal flowline as the water is unlikely to flow down the coastline in this manner. Essentially, coastal flowlines can be treated by the computing system as terminal paths such that a coastal flowline will not be recorded in a flow network as flowing into another coastal flowline.

According to this example, flowline 2852B (15001000017019) would flow into flowline 2852A (15001000017020), but the path would stop here as the computing system would remove the connection from flowline 2852A (15001000017020) to flowline 2852D (15001000017022). Likewise, flowline 2852C (15001000020017) would flow into 2852D (15001000017022) but would not keep going into flowline 2852E (15001000008186) according to the flow network developed by the computing system. Accordingly, if there was a BGA event 2854A occurring, a monitoring station 2858 would be linked to it, but not stressor 2856B or stressor 2856A. If the BGA event 2854B occurred, stressor 2856B and stressor 2856A would be linked to it, but not monitoring station 2858.

In one or more embodiments, a topography defines divergent flowlines comprising (e.g., a first flowline indicating a direction of fluid flow over the area, and a second flowline that diverges from the first flowline). For instance, there could be some outflows from estuaries that loop around and eventually link back up with either the same estuary or another estuary.

Figure 29:
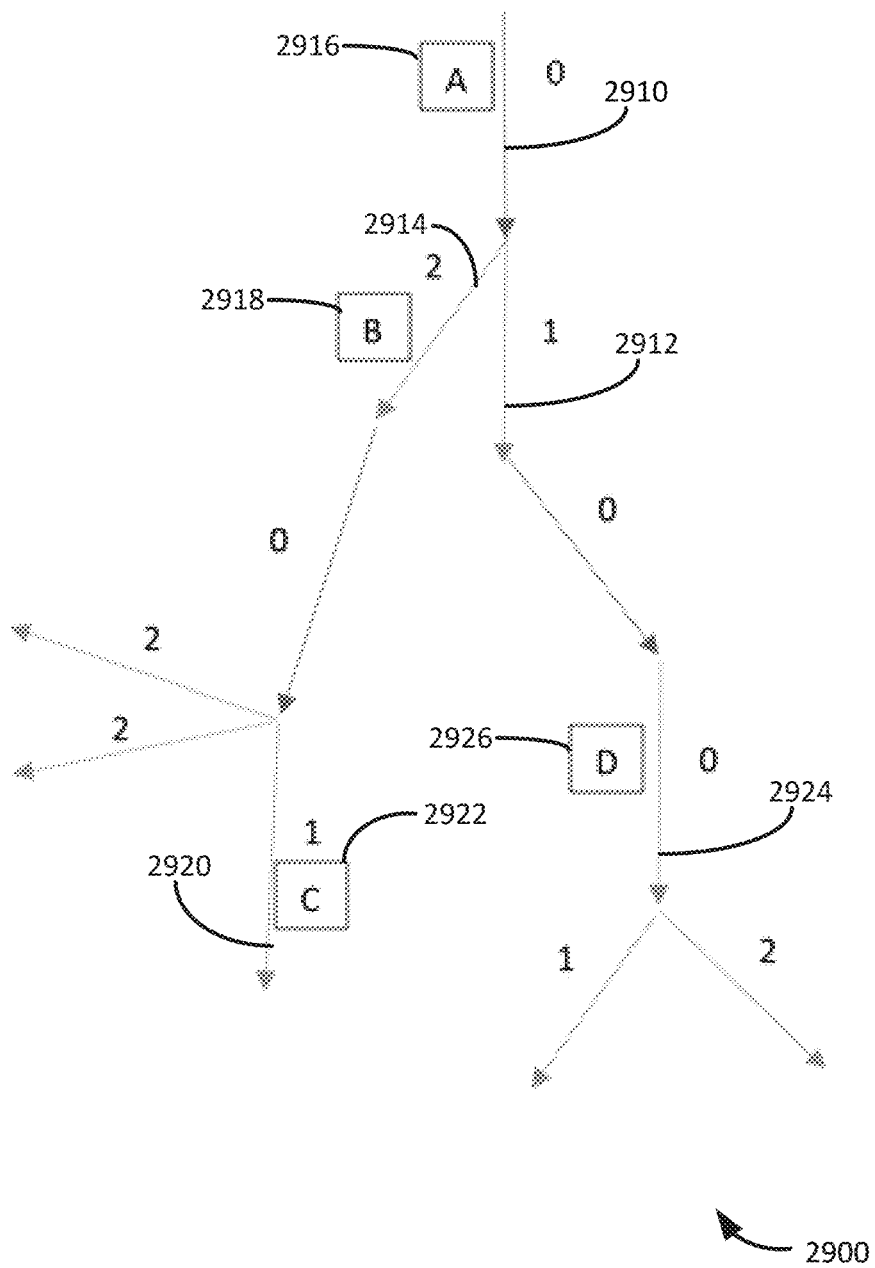
FIG. 29 illustrates an example graphical user interface for determining a flow network with divergent flowlines in at least one embodiment of the present technology.

FIG. 29 illustrates an example for determining a flow network with divergent flowlines. Occasionally, a flow path will split, and water from one flowline will branch off into two or more flowlines. This example illustrates how some embodiments use the NHDPlus HR FlowlineVAA data to identify which of the flow path is the "main" path (e.g., that path that funnels most of the water from a source), and which of the flow paths are "divergent" paths (e.g., paths that funnel less water than the main path).

As seen in the embodiment of FIG. 29, water that flows along a single flowline (shown as blue lines) has a divergence value of 0. In some cases, however, the water of a given flowline can diverge to form two or more flowlines. When this happens, one of the flowlines is determined to be the main downstream path (shown as green lines) and has a divergence value of 1, while the other flowlines (shown as orange lines) are considered to be "divergent flowlines" and have a divergence of 2. In some embodiments, a computing system can use only the main flowlines and exclude divergent flowlines. If divergent flowlines are excluded from the flow table, then a stressor event (e.g., blue green algae event) occurring on a divergent flowline would not be tied to upstream monitoring stations/stressors and would only be associated with the monitoring stations/stressors that are also linked to the same divergent flowline. This means that there would be no upstream linking for any divergent flowline. However, a divergent flowline may still have a downstream main flowline (the divergent flowline flows into the next downstream flowline), and the stressor events occurring on this downstream main flowline can be linked upstream to any monitoring stations or stressors that get matched to the original divergent flowline. But the upstream pathway would stop at the original divergent flowline and not go any further.

As an example, flowline 2910 flows into main flowline 2912 and also into a divergent flowline 2914. The computing system can exclude divergent flowlines such as divergent flowline 2914 from the analysis and remove the connection between flowline 2910 and divergent flowline 2914 in the flow table. This means that an object, such as Object B 2918 associated with divergent flowline 2914, could be matched to flowline 2914 if it is the closest flowline based on the nearest neighbor flowline matching business rules. All events matched to this divergent flowline would be linked together. However, if the computing system was asked to look upstream of this divergent flowline, it would not find a link in the flow table (as it has been removed) and therefore would not link Object B 2918 to upstream Object A 2916, which is an object associated with flowline 2910. However, Object C 2922, which is matched to flowline 2920 is on a main downstream flowline from Object B 2918 and would therefore be associated with Object B 2918 when divergent flowlines are excluded. However, both Object B 2918 and Object C 2922 would not be associated with Object A 2910. Only Object D 2926, which is on the main downstream flowline 2924 from flowline 2910 would be associated with Object A 2916 in this embodiment.

Additionally, or alternatively, a computing system can select one or more related data objects from the plurality of data objects by associating, based on the location, the identified data object with divergent flowlines as well (e.g., both main flowline 2912 and divergent flowline 2914 could be associated with flowline 2910). In this example, if divergent flowlines are included, then Object B 2918, Object C 2922, and Object D 2926 would all be associated with Object A 2916. In this way, the computing system can select a selected flowline from the divergent flowlines and select the one or more related data objects associated with the selected flowline (e.g., link a stressor event to upstream stressors/stations in flowline 2910). In one or more embodiments, a computing system can provide user settings for selecting the matching criteria (e.g., toggling on and off divergent path connections from a dashboard like dashboard 2202 in FIG. 22A). For instance, computing systems can retain information about whether a matched flowline is a main path or divergent path for users to set filters in their output.

In some embodiments, stressor values (e.g., measurements recorded) can be split to account for divergent paths (e.g., if a wastewater treatment facility had an outgoing flow of 100 MGD and four distributaries, the outgoing flow could be split across each path resulting in 25 MGD of flow per path or weighted based on the proportion of water splitting off into each flowline).

Figure 30A:
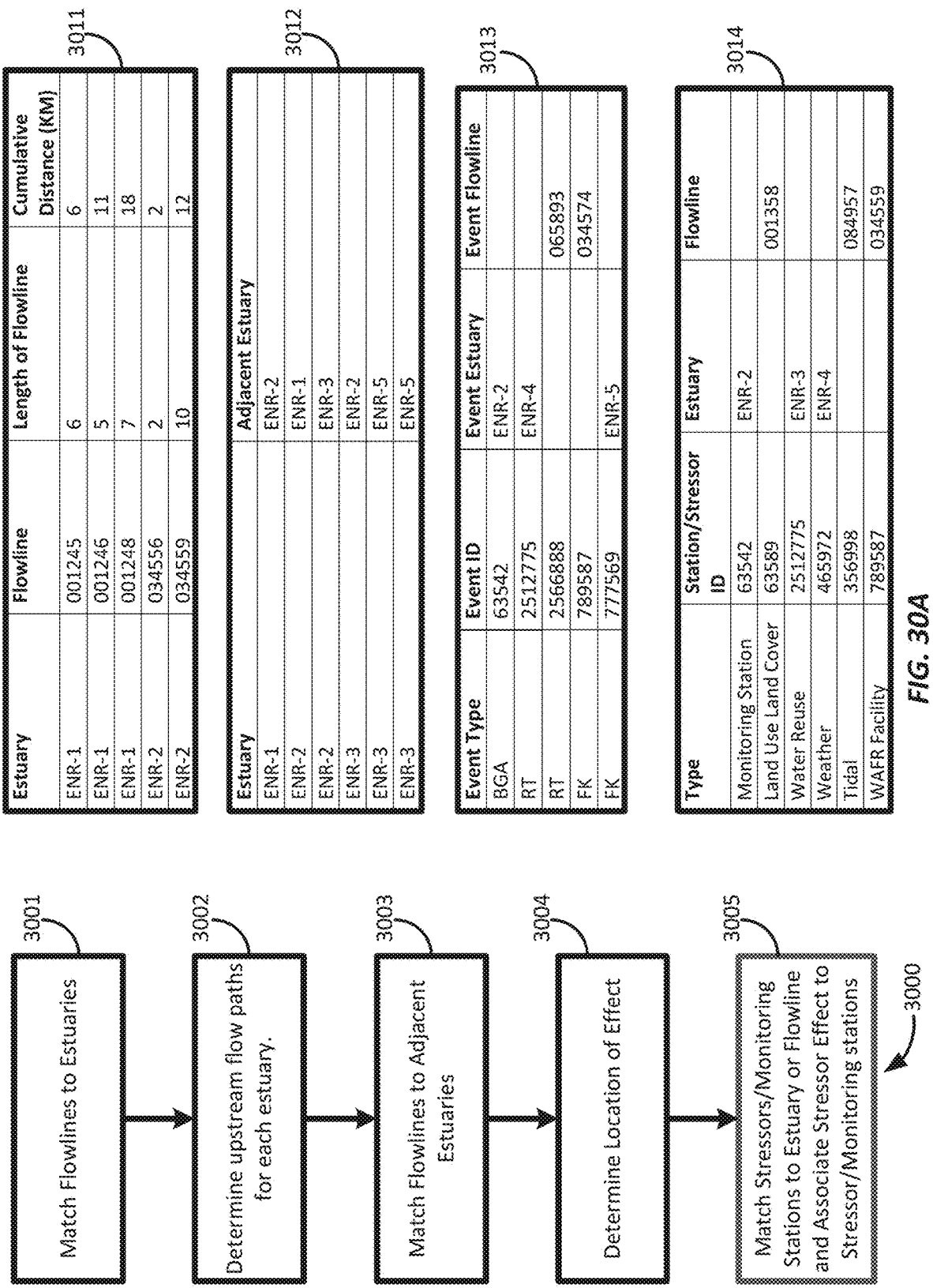

FIGS. 30A-30B shows an example of generation of data tables for associating effects of stressors with monitoring stations and stressors. In this example, a topography with polygons for estuaries or estuary zones (E1-E4) was used based on Numeric Nutrient Criteria (NNC) dataset. A National Hydrologic Dataset Plus High Resolution (NHDPlus HR) data set was used to identify flowlines, flow direction, water bodies, and catchments. In this example, the NHDPlus HR flow table provided unidirectional information about flowlines. However, bidirectionality was assumed between adjacent estuaries.

A method 3000 shows a method of generating the data table for associating effects of stressors with monitoring stations and stressors. In an optional operation 3001 of method 3000, flowlines were matched to estuaries by finding flowlines that intersected with the estuaries. A flowline will be considered "leading into" an estuary when it's "From Node" is outside of an estuary and it's "To Node" intersects with or is inside of an estuary boundary. A flowline will be considered "leading out" of an estuary when it's "From Node" is inside or intersects with an estuary boundary and it's "To Node" is not inside any estuary. A flowline is considered within an estuary when the "From Node" is inside an estuary and the "To Node" is also inside any estuary. If a "From Node" is outside of an estuary and the "To Node" is also outside of an estuary, then a flowline can be considered outside of the estuary even if part of the flowline intersects the estuary.

In an operation 3002 of method 3000, upstream flow paths were determined for each estuary by taking all flowlines that "lead into" an estuary ("From Node" is outside of an estuary and it's "To Node" intersects with or is inside of an estuary boundary) and mapping out all to-from connections from those flowlines within the determined cutoff distance/boundary. In this example, a subwatershed boundary was used. The computing system examined divergent flowlines. Data table 3011 shows flowlines associated with the estuary along its upstream path, the length of the flowline, and the cumulative distance from the estuary to the flowline along the shortest path. Since flowlines converge and diverge, it is possible for an estuary to be mapped to the same flowline along different flow paths when divergent flowlines are included. In this example, estuary flowline associations were selected with the smallest cumulative distance (i.e., the association with the shortest path). Estuaries can have multiple inflows and can therefore have multiple upstream paths. All flowlines along all upstream paths from an estuary can be included.

In an operation 3003 of method 3000, the computing system matches estuaries to adjacent estuaries (e.g., estuaries that share a boundary line according to the topography information). Data table 3012 shows estuaries matched to adjacent estuaries.

In an operation 3004 of method 3000, the computing system determines a location of a stressor effect. In this example, sample data indicating blue green algae (BGA), red tide (RT), and fish kill (FK) events were simulated to occur inside or outside of estuaries (i.e., effects of stressors). If the event occurs in an estuary, the computing system matched it to an estuary. If the event occurs outside of an estuary, the computing system matched it to a flowline (e.g., match it to the closest flowline that intersects that body of water—otherwise, match it to the closest flowline in geographic distance). Data table 3013 shows an example of matched events matched to either estuaries or flowlines.

It should be noted here that although this example methodology is described in the context of an estuary, the present embodiments are not so limited. Those of ordinary skill in the art should readily appreciate that the methodology described herein may apply to any body of water where mixing in a plurality of directions is assumed.

In an operation 3005 of method 3000, the computing system matched stressors and/or monitoring stations to a flowline or estuary for associating a stressor effect with the cause stressors and/or monitoring stations. For instance, the computing system determines if the stressors of interest and the monitoring stations occur inside or outside of an estuary. If the stressor or monitoring station exists in an estuary, the computing system matched it to an estuary. If the monitoring station or water-based stressor exists within a body of water, the computing system matches it to the closest flowline that intersects that body of water—otherwise, the computing system matches it to the closest flowline by distance. If the land-based stressor exists within a catchment, match it to the closest flowline within the catchment. If the land-based stressor exists in a catchment without a flowline, the computing system will match that stressor to any effect stressor (e.g., BGA, RT, and FK) events that occur inside the same catchment.

Once the effect stressors, cause stressors, and monitoring stations have been matched to either an estuary or to a flowline, the computing system can link the effect stressors to the appropriate stressors and/or monitoring stations. For effect stressor events that occur inside estuaries, the computing system can link or associate these events to all stressors and monitoring stations inside of the same estuary, adjacent estuaries, upstream paths from the estuary, and upstream paths from the adjacent estuaries. In this example effect stressor events in an estuary will be tied to all cause stressors/monitoring stations in an estuary and adjacent estuaries no matter the distance between these objects, but in other examples cut-offs could be used or smaller zones. For effect stressor events that occur outside of estuaries, each event will be matched to a flowline and linked to all cause stressors and monitoring stations inside the same subwatershed that fall along all upstream paths from this flowline. FIG. 30B shows an example of a data table 3040 with example effects of stressors linked to monitoring stations and stressors according to embodiments herein. In this example, the effect stressors are blue green algae (BGA), red tide (RT) and fish kill (FT) events denoted in an event type column 3042. Each of the event types can have a unique identifier (e.g., shown in an event id column 3044) to distinguish between different events of the same type (e.g., multiple blue green algae events in the same topography). The causes can be linked (i.e., associated) to a water body or flowline. For instance, RT event 2566888 is linked to flowlines in an event flowline 3046 and BGA and FK events 63542 and 777569, respectively, are linked to estuary water bodies in an event estuary column 3048. Using these links, the computing system can match these cause stressors to the events in a type column 3050 (monitoring stations and cause stressors). Each station or stressor can also be uniquely identified in a station/stress id column 3052. The associations of those stations or stressors to a flowline or estuary can be shown in station/stressor flowline column 3054 and station/stressor estuary column 3056 respectively. Accordingly, embodiments herein are useful for appropriately identifying potential upstream stressors and monitoring stations in response to the effect of a stressor (e.g., for controlling the effect of the stressor or providing visualizations to a user). For example, if a BGA bloom occurs in one estuary, the computing system can associate it with all monitoring stations within that estuary, and with all upstream monitoring stations (within the determined boundary and/or flow distance cutoff) along the flow paths into the estuary. Additionally, the computing system can associate the BGA bloom with all monitoring stations in adjacent estuaries, and (optionally) associate the BGA bloom with all upstream monitoring stations (within the determined boundary and/or flow distance cutoff) from each adjacent estuary as well.

Figure 31:
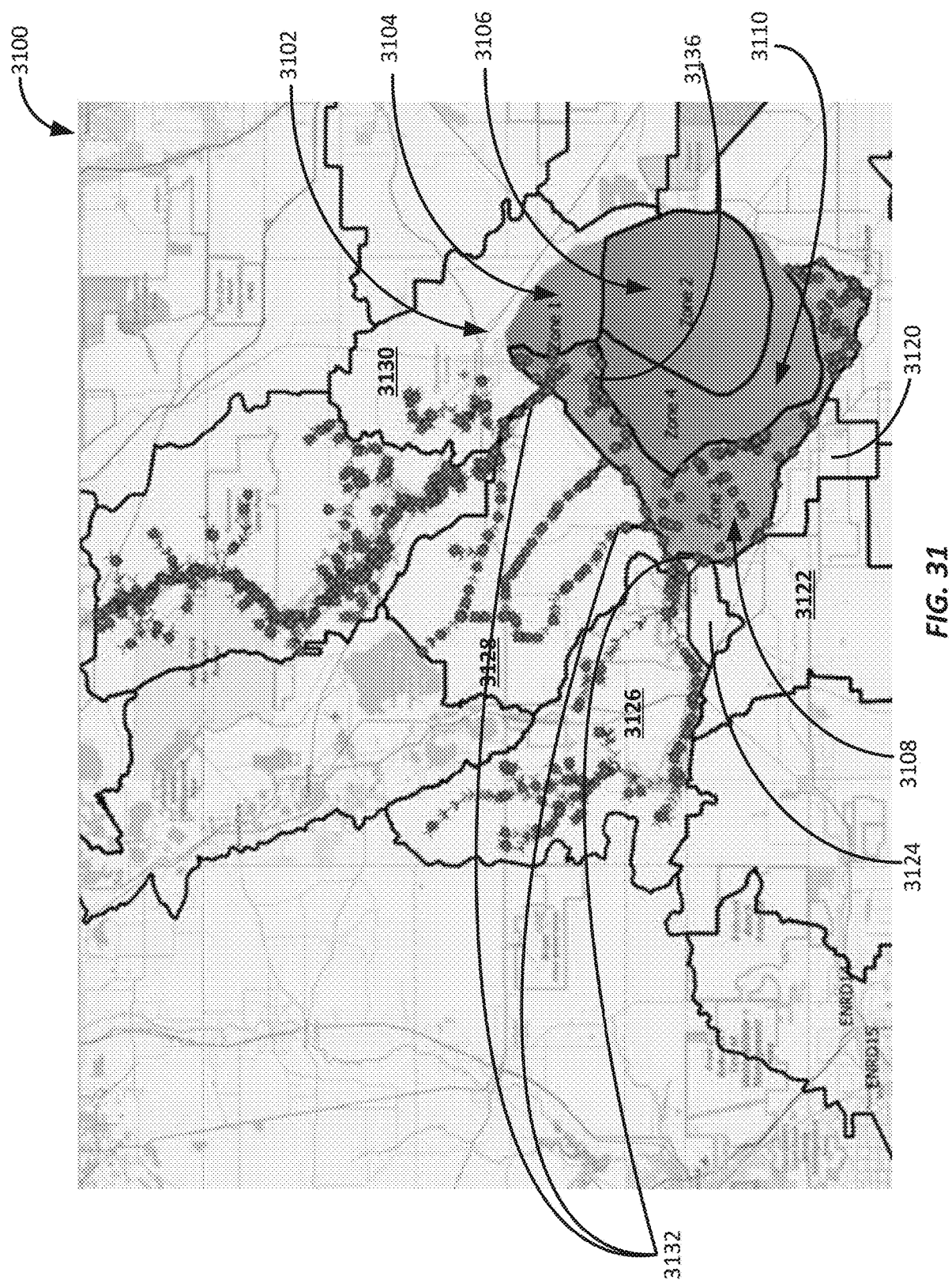
FIG. 31 illustrates an example graphical user interface for showing how an effect stressor located in a body of water partitioned into multiple zones with mixing in a plurality of directions assumed for each zone is associated with monitoring stations according to one embodiment of the present technology.

FIG. 31 illustrates a portion 3100 of a graphical user interface displaying an example of large body of water 3102 partitioned into four zones—Zone-1 3104, Zone-2 3106, Zone-3 3108, and Zone-4 3110. Mixing in a plurality of directions is assumed in each zone (but not in adjacent zones). Zone-3 3108 exists in five (5) different subwatershed boundaries (cutoff boundaries) 3120, 3122, 3126, 3128, and 3130. Note that in some embodiments, subwatersheds can overlap. For example, area 3124 indicates an area that is in both subwatershed 3122 and subwatershed 3126. Therefore, area 3124 indicates an area where subwatershed 3122 and subwatershed 3126 overlap. Inflows into Zone-3 3108 (e.g., inflows 3132) are identified, and all upstream flowlines from these inflows (within the subwatershed boundaries) are also identified (green arrowed lines). A BGA event 3136 (blue diamond) that is located in Zone-3 3108 will be linked to all monitoring stations (indicated in FIG. 31 using solid red dots) that exist in Zone-3 3108, as well as all monitoring stations matched to flowlines along the upstream paths that lead into Zone-3 3108. This process can be used for linking any upstream and downstream objects of interest.

In one example, water bodies (such as estuaries) could be treated differently. For instance, estuaries can be isolated by removing all flowlines in estuaries. These removed flowlines will be excluded from the upstream and downstream networking process. The computing system will match all stressors and monitoring stations in an estuary together but exclude estuaries from any upstream or downstream associations. Additionally, the computing system can be configured to include adjacent bodies of water during linking, or alternatively, to exclude them.

Regardless of how flow networks are formed, a computing system can associate objects and determine relationships such as a "source" when referring to the upstream object of interest (source) and the "destination" when referring to a downstream object of interest. These relationships can help with controlling monitoring stations for monitoring for linked sources or effects of a stressor and can help identify relationships between sources and effects for controlling effects.

What is claimed is:

1. A computer-program product tangibly embodied in a non-transitory machine-readable storage medium, the computer-program product including instructions operable to cause a computing system to:
   obtain topography data for an area comprising water;
   derive a topography from the topography data for the area comprising water, wherein the topography defines bounds for one or more catchments, each catchment indicating land capable of collecting or draining water based on an elevation of the catchment;
   receive an indication of an identified data object, wherein the identified data object represents a stressor to the area or a first monitoring station configurable to monitor the stressor, and wherein the stressor negatively impacts a quality of the water in the area;
   determine a location for the identified data object in the topography;
   select, from a plurality of data objects, one or more related data objects to be related to the identified data object by:
      determining a classification indicating whether the identified data object operates in water, wherein when a given stressor is a candidate to stress a water ecosystem in the area, it is classified as operating in water, and when a given monitoring station is configurable to monitor a given stressor by monitoring water in the area it is classified as operating in water;
      selecting, based on the location and the classification, the one or more related data objects; and
   based on the one or more related data objects selected, generate one or more user interface controls for monitoring the area, wherein the one or more user interface controls comprise selectable objects displayed on a graphical user interface that, when actuated, control a function of one or more monitoring stations configured to monitor the stressor, and wherein the instructions are operable to cause the computing system to generate the one or more user interface controls by generating a flow network based on selecting the one or more related data objects, wherein the flow network graphically represents a direction of water flow over the area through one or more flowlines and defines a relationship between multiple data objects in the area; and
   wherein the one or more related data objects comprise one or more of:
      a second monitoring station configurable to monitor the stressor;
      a cause for the stressor to the area; and
      an effect of the stressor on the area.

2. The computer-program product of claim 1, wherein the topography further defines the one or more flowlines indicating the direction of water flow over the area; and
   wherein the instructions are operable to cause the computing system to select the one or more related data objects from the plurality of data objects by:
      determining, based on the topography, that the identified data object represents a land-based stressor and is in a first catchment of the one or more catchments;
      wherein when there is at least one flowline, of the one or more flowlines, in the first catchment, associating the identified data object with a geographically closest flowline in the first catchment; and
      wherein when there is not a flowline in the first catchment and the one or more related data objects are assigned as in the first catchment, associating the identified data object with the one or more related data objects.

3. The computer-program product of claim 1,
   wherein the topography further defines bounds for one or more water bodies, each water body indicating accumulated water in the area;
   wherein the topography further defines the one or more flowlines indicating the direction of water flow over the area; and wherein the instructions are operable to cause the computing system to select the one or more related data objects from the plurality of data objects by:
determining, based on the topography, that the identified data object is in a first water body of the one or more water bodies, or in a buffer associated with the first water body;
wherein when there is at least one flowline, of the one or more flowlines, in the first water body, associating the identified data object with a geographically closest flowline that is intersecting the first water body;
wherein when there is not a flowline in the first water body, associating the identified data object with the geographically closest flowline; and
wherein the one or more related data objects are associated with a flowline associated with the identified data object.

4. The computer-program product of claim 1,
wherein the topography further defines bounds for one or more water bodies, each water body indicating accumulated water in the area;
wherein the topography further defines the one or more flowlines indicating a direction of water flow over the area; and
wherein the instructions are operable to cause the computing system to:
group the one or more water bodies into a first group comprising water bodies classified as mixing directionally, and a second group comprising water bodies classified as mixing in a plurality of directions; and
select the one or more related data objects from the plurality of data objects by:
determining the identified data object is in a first water body of the second group;
associating the one or more related data objects assigned as in the first water body; and
associating the identified data object with inflows into and outflows out of the first water body of the second group.

5. The computer-program product of claim 4,
wherein the first group comprises one or more of a river or stream in the area; and
wherein the second group comprises one or more of a lake or an estuary in the area.

6. The computer-program product of claim 1,
wherein the topography further defines bounds for one or more water bodies, each water body indicating accumulated water in the area;
wherein the topography further defines the one or more flowlines indicating a direction of water flow over the area; and
wherein the instructions are operable to cause the computing system to:
group the one or more water bodies into a first group comprising water bodies classified as mixing directionally, and a second group comprising water bodies classified as mixing in a plurality of directions;
select the one or more related data objects from the plurality of data objects by:
determining the identified data object is in a first water body of the first group;
wherein when there is at least one flowline, of the one or more flowlines, in the first water body, associating the identified data object with a geographically closest flowline intersecting the first water body;
wherein when there is not a flowline in the first water body, associating the identified data object with the geographically closest flowline; and
wherein the one or more related data objects are associated with a flowline associated with the identified data object.

7. The computer-program product of claim 1,
wherein the topography further defines:
the one or more flowlines indicating a direction of water flow over the area; and
bounds for multiple bounded areas, wherein the bounds for the multiple bounded areas comprise bounds for one or more water bodies, each water body indicating accumulated water in the area; and
wherein the instructions are operable to cause the computing system to select the one or more related data objects from the plurality of data objects by:
associating, based on the location, the identified data object with a flowline in a bounded area of the multiple bounded areas; and
selecting the one or more related data objects associated with the flowline in the bounded area.

8. The computer-program product of claim 1,
wherein the topography further defines:
the one or more flowlines indicating a direction of water flow over the area; and
bounds for multiple bounded areas, wherein the bounds for the multiple bounded areas comprise bounds for one or more water bodies, each water body indicating accumulated water in the area; and
wherein the instructions are operable to cause the computing system to:
generate multiple regions in a given bounded area of the multiple bounded areas;
determine the location for the identified data object is in a first region of the multiple regions; and
select the one or more related data objects from the plurality of data objects by:
associating, based on the location, the identified data object with a flowline in the first region of the multiple bounded areas; and
selecting the one or more related data objects associated with the flowline in the first region.

9. The computer-program product of claim 1, wherein the instructions are further operable to cause the computing system to generate the one or more user interface controls by displaying in the graphical user interface one or more aspects of the flow network, wherein the one or more aspects comprise one or more of relationships between data objects in the flow network, measurements of data objects in the flow network, and predictions for data objects in the flow network.

10. The computer-program product of claim 1, wherein the instructions are further operable to cause the computing system to generate the one or more user interface controls by:
receiving an indication to select upstream data objects;
wherein the one or more related data objects are a computer predicted cause for the stressor to the area and are upstream of the identified data object; and
wherein the flow network defines an estimated direction of flow of a predicted effect of the stressor between multiple data objects in the area.

11. The computer-program product of claim 1, wherein the instructions are further operable to cause the computing system to generate the one or more user interface controls by:

receiving an indication to select downstream data objects;
wherein the one or more related data objects are downstream of the identified data object and comprise one or more of the second monitoring station and a computer predicted effect for the stressor to the area; and
wherein the flow network defines an estimated direction of flow of fluid between multiple data objects in the area.

12. The computer-program product of claim 1, wherein the instructions are operable to cause the computing system to select the one or more related data objects by:
receiving an indication of a cut-off limit for selecting the one or more related data objects, wherein the cut-off limit is based on one or more of: geographic regions of the topography and estimated attenuation of the stressor; and
based on the cut-off limit, limiting association of the identified data object to the one or more related data objects in a flow network.

13. The computer-program product of claim 1,
wherein the identified data object or the one or more related data objects comprise a given monitoring station;
wherein the instructions are operable to cause the computing system to:
receive, according to the one or more user interface controls, an indication of measurements from the given monitoring station monitoring the stressor;
based on the measurements, generate one or more computer models to predict measurements in the area due to the stressor; and
display in the graphical user interface graphical representations of one or more of the measurements from the given monitoring station and predicted measurements from the computer model.

14. The computer-program product of claim 1, wherein the instructions are operable to cause the computing system to:
receive, using the graphical user interface, the indication of the identified data object that represents a stressor to the area; and
responsive to the indication of the identified data object, display in the graphical user interface information derived from multiple monitoring stations associated with the one or more related data objects.

15. The computer-program product of claim 1,
wherein the indication of the identified data object comprises an identity type and a geographic location for the identified data object in the topography; and
wherein the instructions are operable to cause the computing system to determine the location for the identified data object based on the indication of the identified data object.

16. The computer-program product of claim 1,
wherein the identified data object is the first monitoring station configurable to monitor the stressor; and
wherein the instructions are operable to cause the computing system to:
determine that the identified data object comprises a subset of the area; and
determine the location for the identified data object in the topography by identifying a respective location in the topography of one or more datapoints in the subset of the area representative of the identified data object.

17. The computer-program product of claim 1,
wherein the topography further defines divergent flowlines comprising:
a first flowline indicating a primary direction of fluid flow over the area at a flowline connection junction; and
one or more divergent flowlines that diverge from the first flowline at the flowline connection junction; and
wherein the instructions are operable to cause the computing system to select the one or more related data objects from the plurality of data objects by:
associating, based on the location, the identified data object with one or more divergent flowlines;
select a selected flowline from the one or more divergent flowlines; and
select the one or more related data objects associated with the selected flowline.

18. The computer-program product of claim 1,
wherein the identified data object represents the stressor to the area because it is a candidate for causing pollution in or near the area; and
wherein the instructions are operable to cause the computing system to generate the one or more user interface controls by:
detecting the pollution from the identified data object; and
responsive to detecting the pollution, generating the one or more user interface controls to indicate to monitor the second monitoring station or monitor for the spread of the pollution at the second monitoring station.

19. The computer-program product of claim 1,
wherein the identified data object is the first monitoring station;
wherein the first monitoring station is configured to monitor the stressor by collecting, measuring, or analyzing water samples; and
wherein the determining a classification comprises classifying the first monitoring station as operating on water.

20. A computer-implemented method comprising:
obtaining topography data for an area comprising water;
deriving a topography from the topography data for the area comprising water, wherein the topography defines bounds for one or more catchments, each catchment indicating land capable of collecting or draining water based on an elevation of the catchment;
receiving an indication of an identified data object, wherein the identified data object represents a stressor to the area or a first monitoring station configurable to monitor the stressor and wherein the stressor negatively impacts a quality of the water in the area;
determining a location for the identified data object in the topography;
selecting, from a plurality of data objects, one or more related data objects to be related to the identified data object by:
determining a classification indicating whether the identified data object operates in water, wherein when a given stressor is a candidate to stress a water ecosystem in the area, it is classified as operating in water, and when a given monitoring station is configurable to monitor a given stressor by monitoring water in the area it is classified as operating in water;
selecting, based on the location and the classification, the one or more related data objects; and
based on the one or more related data objects selected, generating one or more user interface controls for monitoring the area, wherein the one or more user interface controls comprise selectable objects displayed on a graphical user interface that, when actuated, control a function of one or more monitoring stations configured to monitor the stressor, and wherein generating the one or more user interface controls comprises generating a flow network based on selecting the one or more related data objects, wherein the flow network graphically represents a flow of the water in the area through one or more flowlines and defines a relationship between multiple data objects in the area; and wherein the one or more related data objects comprise one or more of:
- a second monitoring station configurable to monitor the stressor;
- a cause for the stressor to the area; and
- an effect of the stressor to the area.

21. The computer-implemented method of claim 20,
wherein the topography further defines the one or more flowlines indicating the direction of water flow over the area; and
wherein the selecting the one or more related data objects from the plurality of data objects comprises:
determining, based on the topography, the identified data object is in a first catchment of the one or more catchments;
wherein when there is at least one flowline, of the one or more flowlines, in the first catchment, associating the identified data object with a geographically closest flowline in the first catchment; and
wherein when there is not a flowline in the first catchment and the one or more related data objects are assigned as in the first catchment, associating the identified data object with the one or more related data objects.

22. The computer-implemented method of claim 20,
wherein the topography further defines bounds for one or more water bodies, each water body indicating accumulated water in the area;
wherein the topography further defines the one or more flowlines indicating the direction of water flow over the area;
wherein the selecting the one or more related data objects from the plurality of data objects comprises:
determining, based on the topography, the identified data object is in a first water body of the one or more water bodies, or in a buffer associated with the first water body;
wherein when there is at least one flowline, of the one or more flowlines, in the first water body, associating the identified data object with a geographically closest flowline that is intersecting the first water body;
wherein when there is not a flowline in the first water body, associating the identified data object with the geographically closest flowline; and
wherein the one or more related data objects are associated with a flowline associated with the identified data object.

23. The computer-implemented method of claim 20,
wherein the topography further defines bounds for one or more water bodies, each water body indicating accumulated water in the area;
wherein the topography further defines the one or more flowlines indicating the direction of water flow over the area; and
wherein the computer-implemented method further comprises grouping the one or more water bodies into a first group comprising water bodies classified as mixing directionally, and a second group comprising water bodies classified as mixing in a plurality of directions; and
wherein the selecting the one or more related data objects from the plurality of data objects comprises:
determining the identified data object is in a first water body of the second group;
associating the one or more related data objects assigned as in the first water body; and
associating the identified data object with the one or more flowlines flowing into and out of the first water body.

24. The computer-implemented method of claim 20,
wherein the topography further defines bounds for one or more water bodies, each water body indicating accumulated water in the area;
wherein the topography further defines the one or more flowlines indicating the direction of water flow over the area; and
wherein the computer-implemented method further comprises grouping the one or more water bodies into a first group comprising water bodies classified as mixing directionally, and a second group comprising water bodies classified as mixing in a plurality of directions; and
wherein the selecting the one or more related data objects from the plurality of data objects comprises:
determining the identified data object is in a first water body of the first group;
wherein when there is at least one flowline, of the one or more flowlines, in the first water body, associating the identified data object with a geographically closest flowline intersecting the first water body;
wherein when there is not a flowline in the first water body, associating the identified data object with the geographically closest flowline; and
wherein the one or more related data objects are associated with a flowline associated with the identified data object.

25. The computer-implemented method of claim 20,
wherein the topography further defines:
the one or more flowlines indicating the direction of water flow over the area; and
bounds for multiple bounded areas, wherein the bounds for the multiple bounded areas comprise bounds for one or more water bodies, each water body indicating accumulated water in the area; and
wherein the selecting the one or more related data objects from the plurality of data objects comprises:
associating, based on the location, the identified data object with a flowline in a bounded area of the multiple bounded areas; and
selecting the one or more related data objects associated with the flowline in the bounded area.

26. The computer-implemented method of claim 20,
wherein the topography further defines:
the one or more flowlines indicating the direction of water flow over the area; and
bounds for multiple bounded areas, wherein the bounds for the multiple bounded areas comprise bounds for one or more water bodies, each water body indicating accumulated water in the area; and
wherein the computer-implemented method further comprises generating multiple regions in a given bounded area of the multiple bounded areas;

wherein the determining the location for the identified data object comprises determining the location for the identified data object is in a first region of the multiple regions; and wherein the selecting the one or more related data objects from the plurality of data objects comprises:

associating, based on the location, the identified data object with a flowline in the first region of the multiple bounded areas; and selecting the one or more related data objects associated with the flowline in the first region.

27. The computer-implemented method of claim 20, wherein the generating the one or more user interface controls comprises displaying in the graphical user interface one or more aspects of the flow network, wherein the one or more aspects comprise one or more of relationships between data objects in the flow network, measurements of data objects in the flow network, and predictions for data objects in the flow network.

28. The computer-implemented method of claim 20, wherein the generating the one or more user interface controls comprises:

receiving an indication to select upstream data objects;

wherein the one or more related data objects are a computer predicted cause for the stressor to the area and are upstream of the identified data object; and wherein the flow network defines an estimated direction of flow of a predicted effect of the stressor between multiple data objects in the area.

29. The computer-implemented method of claim 20, wherein the generating the one or more user interface controls comprises:

receiving an indication to select downstream data objects;

wherein the one or more related data objects are downstream of the identified data object and comprise one or more of the second monitoring station and a computer predicted effect for the stressor to the area; and wherein the flow network defines an estimated direction of flow of fluid between multiple data objects in the area.

30. A computing device comprising a processor and a memory, the memory containing instructions executable by the processor wherein the computing device is configured to:

obtain topography data for an area comprising water;

derive a topography from the topography data for the area comprising water, wherein the topography defines bounds for one or more catchments, each catchment indicating land capable of collecting or draining water based on an elevation of the catchment;

receive an indication of an identified data object, wherein the identified data object represents a stressor to the area or a first monitoring station configurable to monitor the stressor and wherein the stressor, wherein the stressor negatively impacts a quality of the water in the area;

determine a location for the identified data object in the topography;

select, from a plurality of data objects, one or more related data objects to be related to the identified data object by:

determining a classification indicating whether the identified data object operates in water, wherein when a given stressor is a candidate to stress a water ecosystem in the area, it is classified as operating in water, and when a given monitoring station is configurable to monitor a given stressor by monitoring water in the area it is classified as operating in water;

selecting, based on the location and the classification, the one or more related data objects; and based on the one or more related data objects selected, generate one or more user interface controls for monitoring the area, wherein the one or more user interface controls comprise selectable objects displayed on a graphical user interface that, when actuated, control a function of one or more monitoring stations configured to monitor the stressor, and wherein the instructions are executable by the processor whereby the computing device is further configured to generate the one or more user interface controls by generating a flow network based on selecting the one or more related data objects, wherein the flow network graphically represents a flow of the water in the area through one or more flowlines and defines a relationship between multiple data objects in the area; and wherein the one or more related data objects comprise one or more of:

a second monitoring station configurable to monitor the stressor;

a cause for the stressor to the area; and an effect of the stressor to the area.

* * * * *

UNITED STATES PATENT AND TRADEMARK OFFICE
CERTIFICATE OF CORRECTION

PATENT NO. : 12,196,737 B2  Page 1 of 2
APPLICATION NO. : 17/945428
DATED : January 14, 2025
INVENTOR(S) : Philip David Griffith et al.

It is certified that error appears in the above-identified patent and that said Letters Patent is hereby corrected as shown below:

In the Specification

In Column 2, Line 33, delete "that when" and insert -- that, when --, therefor.

In Column 3, Line 46, delete "model accord-" and insert -- model, accord- --, therefor.

In Column 3, Line 49, delete "network according" and insert -- network, according --, therefor.

In Column 3, Line 52, delete "objects according" and insert -- objects, according --, therefor.

In Column 3, Line 54, delete "stations accord-" and insert -- stations, accord- --, therefor.

In Column 3, Line 57, delete "object according" and insert -- objects, according --, therefor.

In Column 3, Line 60, delete "network according" and insert -- network, according --, therefor.

In Column 3, Line 63, delete "event according" and insert -- event, according --, therefor.

In Column 4, Line 26, delete "illustrate" and insert -- illustrates --, therefor.

In Column 4, Line 29, delete "illustrates" and insert -- illustrate --, therefor.

In Column 4, Line 42, delete "illustrates" and insert -- illustrate --, therefor.

In Column 6, Line 9, delete "dvices, and" and insert -- devices and --, therefor.

In Column 6, Line 47, delete "storing, containing" and insert -- storing, or containing --, therefor.

In Column 7, Line 10, delete "records, and" and insert -- records and --, therefor.

Signed and Sealed this
Twenty-second Day of April, 2025

Coke Morgan Stewart
*Acting Director of the United States Patent and Trademark Office*

CERTIFICATE OF CORRECTION (continued)
U.S. Pat. No. 12,196,737 B2

In Column 7, Line 23, delete "ROLAP OR MOLAP" and insert -- ROLAP or MOLAP --, therefor.

In Column 7, Line 34, delete "device", therefor.

In Column 12, Line 7, delete "bytes" and insert -- bites --, therefor.

In Column 12, Line 7, delete "data, and is" and insert -- data, and the physical layer is --, therefor.

In Column 12, Line 12, delete "communication, and" and insert -- communication and --, therefor.

In Column 12, Line 51, delete "users, and" and insert -- users and --, therefor.

In Column 15, Line 19, delete "fail and" and insert -- fail, and --, therefor.

In Column 16, Line 30, delete "predertmined, or" and insert -- predetermined or --, therefor.

In Column 18, Line 65, delete "However in" and insert -- However, in --, therefor.

In Column 22, Lines 38-39, delete "drop down" and insert -- drop-down --, therefor.

In Column 38, Line 8, delete "blue green" and insert -- blue-green --, therefor.

In Column 38, Line 10, delete "blue green" and insert -- blue-green --, therefor.

In Column 40, Lines 38-39, delete "blue green" and insert -- blue-green --, therefor.

In Column 41, Line 21, delete "y coordinate" and insert -- y-coordinate --, therefor.

In Column 47, Lines 31-32, delete "Blue Green" and insert -- Blue-Green --, therefor.

In Column 48, Line 20, delete "Blue Green" and insert -- Blue-Green --, therefor.

In Column 50, Line 12, delete "blue green" and insert -- blue-green --, therefor.

In Column 51, Line 66, delete "blue green" and insert -- blue-green --, therefor.

In Column 52, Line 53, delete "blue green" and insert --blue-green --, therefor.

In Column 52, Line 58, delete "blue green" and insert -- blue-green --, therefor.